US006506772B1

(12) United States Patent
Brodbeck et al.

(10) Patent No.: US 6,506,772 B1
(45) Date of Patent: Jan. 14, 2003

(54) SUBSTITUTED [1,2,4]TRIAZOLO[1,5A] PYRIDINE DERIVATIVES WITH ACTIVITY AS ADENOSINE RECEPTOR LIGANDS

(75) Inventors: Bernd Brodbeck, Steinen-Hoellstein (DE); Matthias Heinrich Nettekoven, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/998,323

(22) Filed: Nov. 30, 2001

(30) Foreign Application Priority Data

Dec. 15, 2000 (EP) .............................. 00127567

(51) Int. Cl.⁷ ..................... A61K 31/435; C07D 471/04
(52) U.S. Cl. ................. 514/303; 514/183; 514/210; 514/213; 514/228.5; 514/233.2; 514/253; 514/293; 540/481; 540/597; 544/61; 544/127; 544/362; 546/87; 546/119; 546/120
(58) Field of Search ............ 546/87, 119, 120; 540/481, 597; 544/127, 61, 362; 514/303, 183, 210, 213, 228.5, 233.2, 253, 293

(56) References Cited

U.S. PATENT DOCUMENTS 5,356,894 A    10/1994   Zeneca
6,355,653 B1    3/2002   Hoffmann-La Roche

FOREIGN PATENT DOCUMENTS

| WO | WO 94/14812 A | 7/1994 |
| WO | WO 99/43678 A | 9/1999 |
| WO | WO 01/17999 A | 3/2001 |

OTHER PUBLICATIONS

Poulsen et al., *Bioorganic & Med. Chem.*, vol. 6, pp. 619–641 (1998).
Muller et al., *Bioorganic & Med. Chem.*, vol. 6, pp. 707–719 (1998).
Kim et al., *J. Med. Chem.*, vol. 41, pp. 2835–2845 (1998).
Li et al., *J. Med. Chem.*, vol. 41, pp. 3186–3201 (1998).
Baraldi et al., *J. Med. Chem.*, vol. 41, pp. 2126–2133 (1998).
Li et al., *J. Med. Chem.*, vol. 42, pp. 706–721 (1999).
Baraldi et al., *J. Med. Chem.*, vol. 39, pp. 1164–1171 (1996).
Colotta et al., *Arch. Pharm. Med. Chem.*, vol. 332, pp. 39–41 (1999).
Dionisotti et al., *Br. J. Pharmacol.*, vol. 121, pp. 353–360 (1997).

Primary Examiner—Bernard Dentz
(74) Attorney, Agent, or Firm—George W. Johnston; Patricia S. Rocha-Tramaloni; Arthur D. Dawson

(57) ABSTRACT

Substituted [1,2,4]triazolo[1,5a]pyridine derivatives and pharmaceutically active salts thereof with activity as adenosine receptor ligands are disclosed. These compounds are useful for treatment of diseases responsive to modulation of the adenosine receptor.

53 Claims, No Drawings

SUBSTITUTED [1,2,4]TRIAZOLO[1,5A] PYRIDINE DERIVATIVES WITH ACTIVITY AS ADENOSINE RECEPTOR LIGANDS

FIELD OF INVENTION

The present invention is generally related to substituted [1,2,4]triazolo[1,5a]pyridine derivatives and more particularly to particular [1,2,4]triazolo[1,5a]pyridine compounds with activity as adenosine receptor ligands.

BACKGROUND

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the Al receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply versus demand within the tissue. The actions of both subtypes is to increase the amount of available oxygen to tissue and to protect cells against damage caused by a short-term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is also a neuromodulator, possessing global importance in the modulation of molecular mechanisms underlying many aspects of physiological brain function by mediating central inhibitory effects. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$-antagonists have therapeutic potential in the treatment of various forms of dementia, for example in Alzheimer's disease and are useful as neuroprotective agents. Adenosine $A_2$-receptor antagonists inhibit the release of dopamine from central synaptic terminals and reduce locomotor activity and consequently improve Parkinsonian symptoms. The central activities of adenosine are also implicated in the molecular mechanism underlying sedation, hypnosis, schizophrenia, anxiety, pain, respiration, depression and substance abuse. Drugs acting at adenosine receptors therefore have also therapeutic potential as sedatives, muscle relaxants, antipsychotics, anxiolytics, analgesics, respiratory stimulants and antidepressants.

An important role for adenosine in the cardiovascular system is as a cardioprotective agent. Levels of endogenous adenosine increase in response to ischaemia and hypoxia, and protect cardiac tissue during and after trauma (preconditioning). Adenosine agonists thus have potential as cardioprotective agents.

Adenosine modulates many aspects of renal function, including renin release, glomerular filtration rate and renal blood flow. Compounds, which antagonise the renal affects of adenosine, have potential as renal protective agents. Furthermore, adenosine $A_3$ and/or $A_{2B}$ antagonists may be useful in the treatment of asthma and other allergic responses.

Numerous documents describe the current knowledge on adenosine receptors, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., (1999), 332, 39–41.

SUMMARY

The present invention is a compound of the formula

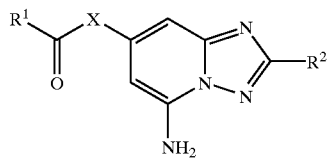

wherein
- $R^1$ is unsubstituted lower alkoxy, cycloalkyl or aryl, or lower alkoxy, cycloalkyl or aryl substituted by halogen or lower alkoxy, or is —NR'R", wherein R' and R" are independently from each other hydrogen, lower alkyl, lower alkenyl, lower alkinyl, unsubstituted —(CR$_2$)$_n$-aryl, or —(CR$_2$)$_n$-aryl, substituted by one to three substituents, selected from the group, consisting of halogen or lower alkoxy, or are —(CH$_2$)$_{n+1}$NR$^a{}_2$, —(CH$_2$)$_n$-pyridinyl, —(CH$_2$)$_n$-indanyl, —(CH$_2$)$_n$-cycloalkyl, —(CH$_2$)$_n$—O-lower alkyl, —(CH$_2$)$_n$—C(O)—NR$^b{}_2$, —(CH$_2$)$_n$—CF$_3$, or R' and R" are together with the N atom to which they are attached unsubstituted pyrrolidin-1-yl, piperidin-1-yl, 3,4-dihydro-1H-isoquinolin-2-yl, morpholinyl, azatidin-1-yl, 3,6-dihydro-2H-pyridin-1-yl, thiomorpholinyl, 2,5-dihydro-pyrrol-1-yl, thiazolidin-3-yl, piperazinyl, azocan-1-yl, azepan-1-yl, octahydroquinolin-1-yl, octahydroquinolin-2-yl, 1,3,4,9-tetrahydro-b-carbolin-2-yl, or pyrrolidin-1-yl, piperidin-1-yl, 3,4-dihydro-1H-isoquinolin-2-yl, morpholinyl, azatidin-1-yl, 3,6-dihydro-2H-pyridin-1-yl, thiomorpholinyl, 2,5-dihydro-pyrrol-1-yl, thiazolidin-3-yl, piperazinyl, azocan-1-yl, azepan-1-yl, octahydroquinolin-1-yl, octahydroquinolin-2-yl, 1,3,4,9-tetrahydro-b-carbolin-2-yl, substituted by one to three substituents selected from the group consisting of lower alkyl, phenyl, benzyl, pyridyl, —C(O)—NR$^c{}_2$, —(CH$_2$)$_n$—O-lower alkyl or —NR$^d$—(C(O)-lower alkyl;
- $R_2$ is unsubstituted aryl or a 5 or 6 membered heteroaryl group substituted by lower alkyl, halogen, hydroxy or lower alkoxy;
- X is a bond or —N(R$^e$)CH$_2$—;
- R, R$^a$, R$^b$, R$^c$, R$^d$, R$^e$ are independently hydrogen or lower alkyl;
- n is 0, 1, 2, 3, 4, 5 or 6;

or a pharmaceutically acceptable salt thereof.

It has surprisingly been found that the compounds of formula I are adenosine receptor ligands.

Objects of the present invention are compounds of formula I and their pharmaceutically acceptable salts per se and as pharmaceutically active substances, their manufacture, pharmaceutical compositions based on a compound in accordance with the invention and their production as well as the use of compounds of formula I in the control or prevention of illnesses based on the modulation of the adenosine system, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardioprotective agents. The most preferred indications in accordance with the present invention are those, which are based on the $A_{2A}$ receptor antagonistic activity and which include disorders of the central nervous system, for example the treatment or prevention of certain depressive disorders, neuroprotection and Parkinson's disease.

DETAILED DESCRIPTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

As used herein, the term "lower alkenyl" denotes an unsaturated straight- or branched-chain, containing 2 to 6 carbon atoms and at least one double bond, for example, ethylen, propylen, isopropylen, n-butylen, i-butylen, 2-butylen, t-butylen and the like. Preferred lower alkenyl groups are groups with 2–4 carbon atoms.

As used herein, the term "lower alkinyl" denotes an unsaturated straight- or branched-chain, containing from 2 to 6 carbon atoms and containing at least one triple bond.

The term "cycloalkyl" denotes a saturated carbocyclic group, containing 3–8 carbon atoms.

The term "halogen" denotes chlorine, iodine, fluorine and bromine.

The term "lower alkoxy" denotes a group wherein the alkyl residue is as defined above, and which is attached via an oxygen atom.

The term "5 or 6 membered heteroaryl group" denotes, but is not limited to, for example furanyl, thiophenyl, pyrrolyl, thiazolyl or pyridinyl and the like.

The term "aryl" denotes phenyl or naphthyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Generally speaking, the most preferred are compounds of formula 1 wherein X is a bond. Compounds wherein X is a bond, $R^1$ is NR'R", R', R" and $R^2$ are as above are also preferred.

Additional preferred compounds are compounds of formula 1 wherein X is a bond, $R^1$ is NR'R", R' and R" are independently from each other hydrogen, lower alkyl, lower alkenyl, lower alkinyl, —(CH$_2$)$_n$—C(O)—N(CH$_3$)$_2$, —(CH$_2$)$_n$—OCH$_3$, —(CH$_2$)$_n$-cycloalkyl or —(CH$_2$)$_n$-pyridin-2-yl and $R_2$ is unsubstituted furyl or thiophenyl, or furyl or thiophenyl substituted by halogen or lower alkyl. Representative of these preferred compounds are compounds including:

- 5-amino-2-(5-bromo-furan-2-yl)-[1,2,4]triazolo[1,5-a]pyridine-7-carboxylic acid diethylamide,
- 5-amino-2-(5-methyl-thiophen-2-yl)-[1,2,4]triazolo[1,5-a]pyridine-7-carboxylic acid cyclohexyl-ethyl-amide,
- 5-amino-2-(5-methyl-furan-2-yl)-[1,2,4]triazolo[1,5-a]pyridine-7-carboxylic acid cyclohexyl-methyl-amide,
- 5-amino-2-furan-2-yl-[1,2,4]triazolo[1,5-a]pyridine-7-carboxylic acid butylamide,
- (5-amino-2-furan-2-yl-[1,2,4]triazolo[1,5-a]pyridin-7-yl)-pyrrolidin-1-yl-methanone
- 5-amino-2-(5-chloro-furan-2-yl)-[1,2,4]triazolo[1,5-a]pyridine-7-carboxylic acid methyl-propyl-amide,
- 5-amino-2-(5-chloro-furan-2-yl)-[1,2,4]triazolo[1,5-a]pyridine-7-carboxylic acid ethyl-isopropyl-amide, 5-amino-2-(5-bromo-furan-2-yl)-[1,2,4]triazolo[1,5-a]
pyridine-7-carboxylic acid ethyl-methyl-amide, 5-amino-2-(5-bromo-furan-2-yl)-[1,2,4]triazolo[1,5-a]
pyridine-7-carboxylic acid methyl-prop-2-ynyl-amide, 5-amino-2-(5-bromo-furan-2-yl)-[1,2,4]triazolo[1,5-a]
pyridine-7-carboxylic acid allyl-methyl-amide, 5-amino-2-(5-bromo-furan-2-yl)-[1,2,4]triazolo[1,5-a]
pyridine-7-carboxylic acid methyl-propyl-amide, 5-amino-2-(5-bromo-furan-2-yl)-[1,2,4]triazolo[1,5-a]
pyridine-7-carboxylic acid isopropyl-methyl-amide, 5-amino-2-(5-bromo-furan-2-yl)-[1,2,4]triazolo[1,5-a]
pyridine-7-carboxylic acid butyl-methyl-amide, 5-amino-2-(5-bromo-furan-2-yl)-[1,2,4]triazolo[1,5-a]
pyridine-7-carboxylic acid ethyl-isopropyl-amide, 5-amino-2-(5-bromo-furan-2-yl)-[1,2,4]triazolo[1,5-a]
pyridine-7-carboxylic acid diallylamide, 5-amino-2-(5-bromo-furan-2-yl)-[1,2,4]triazolo[1,5-a]
pyridine-7-carboxylic acid diisopropylamide, 5-amino-2-(5-bromo-furan-2-yl)-[1,2,4]triazolo[1,5-a]
pyridine-7-carboxylic acid butyl-ethyl-amide, 5-amino-2-(5-bromo-furan-2-yl)-[1,2,4]triazolo[1,5-a]
pyridine-7-carboxylic acid methyl-pentyl-amide, 5-amino-2-(5-bromo-furan-2-yl)-[1,2,4]triazolo[1,5-a]
pyridine-7-carboxylic acid (2-dimethylamino-ethyl)-methyl-amide, 5-amino-2-(5-bromo-furan-2-yl)-[1,2,4]triazolo[1,5-a]
pyridine-7-carboxylic acid cyclopropylmethyl-propyl-amide, 5-amino-2-(5-bromo-furan-2-yl)-[1,2,4]triazolo[1,5-a]
pyridine-7-carboxylic acid methyl-(2-pyridin-2-yl-ethyl)-amide, 5-amino-2-(5-bromo-furan-2-yl)-[1,2,4]triazolo[1,5-a]
pyridine-7-carboxylic acid dipropylamide, 5-amino-2-(5-bromo-furan-2-yl)-[1,2,4]triazolo[1,5-a]
pyridine-7-carboxylic acid cyclohexyl-methyl-amide, 5-amino-2-(5-bromo-furan-2-yl)-[1,2,4]triazolo[1,5-a]
pyridine-7-carboxylic acid allyl-cyclopentyl-amide, 5-amino-2-(5-bromo-furan-2-yl)-[1,2,4]triazolo[1,5-a]
pyridine-7-carboxylic acid cyclohexyl-ethyl-amide, 5-amino-2-(5-bromo-furan-2-yl)-[1,2,4]triazolo[1,5-a]
pyridine-7-carboxylic acid diisobutylamide, 5-amino-2-(5-bromo-furan-2-yl)-[1,2,4]triazolo[1,5-a]
pyridine-7-carboxylic acid ethyl-(2-pyridin-2-yl-ethyl)-amide, 1-[5-amino-2-(5-bromo-furan-2-yl)-[1,2,4]triazolo[1,5-a]
pyridine-7-carbonyl]-piperidine-3-carboxylic acid diethylamide, 5-amino-2-(5-bromo-furan-2-yl)-[1,2,4]triazolo[1,5-a]
pyridine-7-carboxylic acid dimethylcarbamoylmethyl-methyl-amide, 5-amino-2-(5-bromo-furan-2-yl)-[1,2,4]triazolo[1,5-a]
pyridine-7-carboxylic acid (2-methoxy-ethyl)-methyl-amide and 5-amino-2-(5-bromo-furan-2-yl)-[1,2,4]triazolo[1,5-a]
pyridine-7-carboxylic acid ethyl-(2-methoxy-ethyl)-amide.

Other preferred compounds are compounds of formula 1 wherein X is a bond, $R^1$ is NR'R" and wherein one of R' and R" is hydrogen and the other is lower alkyl and $R^2$ is unsubstituted furyl or thiophenyl, or furyl or thiophenyl substituted by halogen or lower alkyl Exemplary of this preferred compound is 5-Amino-2-furan-2-yl-[1,2,4]triazolo[1,5-a]pyridine-7-carboxylic acid butylamide.

Another preferred compound is a compound of formula 1 wherein X is a bond, $R^1$ is NR'R" or both R' and R" are lower alkyl and $R^2$ is unsubstituted furyl or thiophenyl, or furyl or thiophenyl substituted by halogen or lower alkyl. Exemplary of this preferred compound is 5-Amino-2-(5-bromo-furan-2-yl)-[1,2,4]triazolo[1,5-a]pyridine-7-carboxylic acid diethylamide;

5-Amino-2-(5-chloro-furan-2-yl)-[1,2,4]triazolo[1,5-a]
pyridine-7-carboxylic acid methyl-propyl-amide;

5-Amino-2-(5-chloro-furan-2-yl)-[1,2,4]triazolo[1,5-a]
pyridine-7-carboxylic acid ethyl-isopropyl-amide;

5-Amino-2-(5-bromo-furan-2-yl)-[1,2,4]triazolo[1,5-a]
pyridine-7-carboxylic acid ethyl-methyl-amide;

5-Amino-2-furan-2-yl-[1,2,4]triazolo[1,5-a]pyridine-7-carboxylic acid diethylamide 5-Amino-2-(5-bromo-furan-2-yl)-[1,2,4]triazolo[1,5-a]
pyridine-7-carboxylic acid isopropyl-methyl-amide;

5-Amino-2-(5-bromo-furan-2-yl)-[1,2,4]triazolo[1,5-a]
pyridine-7-carboxylic acid butyl-methyl-amide;

5-Amino-2-(5-bromo-furan-2-yl)-[1,2,4]triazolo[1,5-a]
pyridine-7-carboxylic acid ethyl-isopropyl-amide;

5-Amino-2-(5-bromo-furan-2-yl)-[1,2,4]triazolo[1,5-a]
pyridine-7-carboxylic acid diisopropylamide;

5-Amino-2-(5-bromo-furan-2-yl)-[1,2,4]triazolo[1,5-a]
pyridine-7-carboxylic acid butyl-ethyl-amide;

5-Amino-2-(5-bromo-furan-2-yl)-[1,2,4]triazolo[1,5-a]
pyridine-7-carboxylic acid methyl-pentyl-amide;

5-Amino-2-(5-bromo-furan-2-yl)-[1,2,4]triazolo[1,5-a]
pyridine-7-carboxylic acid dipropylamide; and 5-Amino-2-(5-bromo-furan-2-yl)-[1,2,4]triazolo[1,5-a]
pyridine-7-carboxylic acid diisobutylamide.

Yet more preferred compounds include the compound of formula 1 wherein X is a bond, $R^1$ is NR'R", one of R' and R" is —(CH$_2$)$_n$-cycloalkyl and the other is hydrogen, or one of R' and R" is —(CH$_2$)$_n$-cycloalkyl and the other is lower alkyl, or both R' and R" are —(CH$_2$)$_n$-cycloalkyl and wherein n is 0, 1, 2, 3, 4, 5 or 6, and $R^2$ is unsubstituted furyl or thiophenyl, or furyl or thiophenyl substituted by halogen or lower alkyl. Further preferred compounds according to formula 1 are compounds wherein X is a bond, $R^1$ is NR'R", $R^2$ is unsubstituted furyl or thiophenyl, or furyl or thiophenyl substituted by halogen or lower alkyl and wherein one of R' and R" lower alkyl and the other is lower alkinyl. Yet other preferred compounds of formula 1 are found when X is a bond, $R^1$ is NR'R", $R^2$ is unsubstituted furyl or thiophenyl, or furyl or thiophenyl substituted by halogen or lower alkyl, and wherein one of R' and R" lower alkyl and the other is lower alkenyl, or one is —(CH$_2$)$_n$-cycloalkyl and the other is lower alkenyl, or both R' and R" are lower alkenyl, and wherein n is 0, 1, 2, 3, 4, 5 or 6. Further preferred compounds according to formula 1 are found when X is a bond, $R^1$ is NR'R", $R^2$ is unsubstituted furyl or thiophenyl, or furyl or thiophenyl substituted by halogen or lower alkyl, and wherein one of R' and R" lower alkyl and the other is lower alkenyl, or one of R' and R" is —(CH$_2$)$_n$-cycloalkyl and the other is lower alkenyl, and wherein one of R' and R" —(CH$_2$)$_n$-pyridinyl and the other is lower alkyl, and wherein n is 0, 1, 2, 3, 4, 5 or 6. Another preferred compound of formula 1 is wherein X is a bond, $R^1$ is NR'R", $R^2$ is unsubstituted furyl or thiophenyl, or furyl or thiophenyl substituted by halogen or lower alkyl, and wherein one of R' and R" lower alkyl and the other is lower alkenyl, or one is —(CH$_2$)$_n$-cycloalkyl and the other is lower alkenyl, or wherein one of R' and R" is —(CH$_2$)$_n$—OCH$_3$ and the other is lower alkyl, and n is 0, 1, 2, 3, 4, 5 or 6.

Other preferred compounds of formula 1 are wherein X is a bond, $R^1$ is NR'R", $R^2$ is as above, and one of R' and R" is —$(CH_2)_n$—N—$(CH_3)_2$ and the other is lower alkyl, and wherein n is 0, 1, 2, 3, 4, 5 or 6. Additional preferred compounds of formula 1 are where X is a bond, $R^1$ is NR'R", $R^2$ is as above and one of R' and R" is —NR—C(O)—N—$(CH_3)_2$ and the other is lower alkyl, and wherein n is 0, 1, 2, 3, 4, 5 or 6.

Additional preferred compounds of formula 1 are seen when X is a bond, $R^1$ is NR'R", wherein R' and R" are independently from each other hydrogen, lower alkyl, lower alkenyl, lower alkinyl, and $R^2$ is thiazol-2-yl. Further preferred compounds of formula 1 are seen when X is a bond, $R^1$ is NR'R", $R^2$ is thiazol-2-yl and wherein one of R' and R" is hydrogen and the other is lower alkyl. Yet more preferred compounds of formula 1 when X is a bond, $R^1$ is NR'R", $R^2$ is thiazol-2-yl are compounds having R' and R" are lower alkyl. Additional preferred compounds of formula 1 wherein X is a bond, $R^1$ is NR'R", $R^2$ is thiazol-2-yl are formed when one of R' and R" is lower alkyl and the other is lower alkenyl. Yet more preferred compounds of formula 1 when X is a bond $R^1$ is NR'R", $R^2$ is thiazol-2-yl are formed when wherein one of R' and R" is lower alkyl and the other is lower alkinyl. Yet further preferred compounds of formula 1 are formed when X is a bond $R^1$ is NR'R", $R^2$ is thiazol-2-yl, wherein one of R' and R" is —$(CH_2)_n$-pyridinyl and the other is lower alkyl and wherein n is 0, 1, 2, 3, 4, 5 or 6. Other preferred compounds of formula 1 when X is a bond $R^1$ is NR'R", $R^2$ is thiazol-2-yl are seen when wherein R' and R" are both —$(CH_2)_n$-aryl and wherein n is 0, 1, 2, 3, 4, 5 or 6.

Yet more preferred compounds of formula 1 are formed when X is a bond $R^1$ is NR'R", and R' and R" are together with the N atom to which they are attached form unsubstituted pyrrolidinyl, piperidinyl, morpholinyl, 3,6-dihydro-2H-pyridin-1-yl, 2,5-dihydro-pyrrol-1-yl, azocan-1-yl; or pyrrolidinyl, piperidinyl, morpholinyl, 3,6-dihydro-2H-pyridin-1-yl, 2,5-dihydro-pyrrol-1-yl, azocan-1-yl, substituted by lower alkyl, lower alkoxy, —C(O)NH$_2$, —C(O)N(CH$_3$)$_2$, or —N(CH$_3$)—C(O)—CH$_3$ and $R^2$ is unsubstituted furyl or furyl substituted by halogen. Further preferred compounds of formula 1 when X is a bond and $R^1$ is NR'R" are formed when NR'R" form unsubsituted pyrrolidinyl, piperidinyl, or morpholinyl and $R^2$ is unsubstituted furyl or furyl substituted by halogen. Yet more compounds of formula 1 where X is a bond and $R^1$ is NR'R" are formed when —NR'R" form substituted pyrrolidinyl, piperidinyl, morpholinyl, 3,6-dihydro-2H-pyridin-1-yl, 2,5-dihydro-pyrrol-1-yl, or azocan-1-yl; substituted by lower alkyl, lower alkoxy, —C(O)NH$_2$, —C(O)N(CH$_3$)$_2$, or —N(CH$_3$)—C(O)—CH$_3$ and $R^2$ is unsubstituted furyl or furyl substituted by halogen. Additional compounds of formula 1 where X is a bond and $R^1$ is NR'R" are formed when NR'R" form substituted pyrrolidinyl, piperidinyl, morpholinyl, 3,6-dihydro-2H-pyridin-1-yl, 2,5-dihydro-pyrrol-1-yl, or azocan-1-yl; substituted by lower alkyl, lower alkoxy, —C(O)NH$_2$, —C(O)N(CH$_3$)$_2$, or —N(CH$_3$)—C(O)—CH$_3$ and $R^2$ is unsubstituted furyl or furyl substituted by halogen.

Further preferred compounds of formula 1 are formed when X is a bond, $R^1$ is —NR'R" and R' and R" are together with the N atom to which they are attached form unsubstituted pyrrolidinyl, piperidinyl, octahydroquinolin-1-yl, 2,5-dihydro-pyrrol-1-yl, thiazolidinyl, thiazolyl, azepan-1-yl or azocan-1-yl and $R^2$ is thiazolyl. Other preferred compounds of formula 1 are formed when X is a bond and wherein $R^1$ is —NR'R" and R' and R" are together with the N atom to which they are attached form substituted pyrrolidinyl, piperidinyl, octahydroquinolin-1-yl, 2,5-dihydro-pyrrol-1-yl, thiazolidinyl, thiazolyl, azepan-1-yl or azocan-1-yl, wherein said substituents are lower alkyl, and $R^2$ is thiazolyl. Yet other preferred compounds of formula 1 include compounds wherein $R^1$ is —NR'R" and R' and R" together with the N atom to which they are attached form unsubstituted pyrrolidin-1-yl, azepan-1-yl, piperidin-1-yl, or azocan-1-yl, or substituted pyrrolidin-1-yl, azepan-1-yl, piperidin-1-yl, or azocan-1-yl, and wherein said substituents are lower alkyl or lower alkoxy, and $R^2$ is pyridyl. Additional preferred compounds of formula 1 are formed when X is a bond, $R^1$ is —NR'R" and R' and R" together with the N atom to which they are attached form unsubstituted substituted pyrrolidin-1-yl, azepan-1-yl, piperidin-1-yl, or azocan-1-yl and $R^2$ is pyridyl. Yet more preferred compounds of formula I include compounds where X is a bond, $R^1$ is —NR'R" and R' and R" together with the N atom to which they are attached form substituted pyrrolidin-1-yl, azepan-1-yl, piperidin-1-yl, or azocan-1-yl, and wherein said substituents are lower alkyl or lower alkoxy and $R^2$ is pyridyl.

Other preferred compounds of formula 1 are compounds wherein X is a bond, wherein $R^1$ is —NR'R" and R' and R" are independently from each other lower alkenyl, lower alkyl, —$(CH_2)_n$-cycloalkyl, —$(CH_2)_n$-pyridinyl or —$(CH_2)_n$-phenyl and $R^2$ is pyridyl.

Compound of formula I, wherein $R^1$ is —NR'R" and R' and R" are independently from each other lower alkyl, lower alkenyl, lower alkinyl, —$(CH_2)_n$-phenyl or —$(CH_2)_n$-pyridinyl and $R^2$ is thiazolyl are further preferred.

Such compounds are 5-amino-2-thiazol-2-yl-[1,2,4]triazolo[1,5-a]pyridine-7-carboxylic acid butylamide, 5-amino-2-thiazol-2-yl-[1,2,4]triazolo[1,5-a]pyridine-7-carboxylic acid diethylamide, 5-amino-2-thiazol-2-yl-[1,2,4]triazolo[1,5-a]pyridine-7-carboxylic acid ethyl-methyl-amide, 5-amino-2-thiazol-2-yl-[1,2,4]triazolo[1,5-a]pyridine-7-carboxylic acid methyl-prop-2-ynyl-amide, 5-amino-2-thiazol-2-yl-[1,2,4]triazolo[1,5-a]pyridine-7-carboxylic acid allyl-methyl-amide, 5-amino-2-thiazol-2-yl-[1,2,4]triazolo[1,5-a]pyridine-7-carboxylic acid methyl-propyl-amide, 5-amino-2-thiazol-2-yl-[1,2,4]triazolo[1,5-a]pyridine-7-carboxylic acid isopropyl-methyl-amide, 5-amino-2-thiazol-2-yl-[1,2,4]triazolo[1,5-a]pyridine-7-carboxylic acid butyl-methyl-amide, 5-amino-2-thiazol-2-yl-[1,2,4]triazolo[1,5-a]pyridine-7-carboxylic acid ethyl-pyridin-4-ylmethyl-amide, 5-amino-2-thiazol-2-yl-[1,2,4]triazolo[1,5-a]pyridine-7-carboxylic acid dibenzylamide, 5-amino-2-thiazol-2-yl-[1,2,4]triazolo[1,5-a]pyridine-7-carboxylic acid ethylamide, 5-amino-2-thiazol-2-yl-[1,2,4]triazolo[1,5-a]pyridine-7-carboxylic acid dipropylamide or 5-amino-2-thiazol-2-yl-[1,2,4]triazolo[1,5-a]pyridine-7-carboxylic acid diisobutylamide.

Preferred are compounds of formula I, wherein $R^1$ is —NR'R" and R' and R" are together with the N atom to which they are attached pyrrolidinyl, piperidinyl, morpholinyl, 3,6-dihydro-2H-pyridin-1-yl, 2,5-dihydro-pyrrol-1-yl, azocan-1-yl, and wherein the rings may be unsubstituted or substituted by lower alkyl, lower alkoxy, —C(O)NH$_2$, —C(O)N(CH$_3$)$_2$, —N(CH$_3$)—C(O)—CH$_3$ and $R^2$ is furyl unsubstituted or substituted by halogen.

Examples of such compounds are
[5-amino-2-(5-bromo-furan-2-yl)-[1,2,4]triazolo[1,5-a] pyridin-7-yl]-pyrrolidin-1-yl-methanone,
[5-amino-2-(5-bromo-furan-2-yl)-[1,2,4]triazolo[1,5-a] pyridin-7-yl]-piperidin-1-yl-methanone,
(5-amino-2-furan-2-yl-[1,2,4]triazolo[1,5-a]pyridin-7-yl)-pyrrolidin-1-yl-methanone,
(5-amino-2-furan-2-yl-[1,2,4]triazolo[1,5-a]pyridin-7-yl)-piperidin-1-yl-methanone,
(5-amino-2-furan-2-yl-[1,2,4]triazolo[1,5-a]pyridin-7-yl)-morpholin-4-yl-methanone,
[5-amino-2-(5-chloro-furan-2-yl)-[1,2,4]triazolo[1,5-a] pyridin-7-yl]-(3,6-dihydro-2-H-pyridin-1-yl)-methanone,
[5-amino-2-(5-chloro-furan-2-yl)-[1,2,4]triazolo[1,5-a] pyridin-7-yl]-(2-methyl-pyrrolidin-1-yl)-methanone,
[5-amino-2-(5-bromo-furan-2-yl)-[1,2,4]triazolo[1,5-a] pyridin-7-yl]-(2,5-dihydro-pyrrol-1-yl)-methanone,
[5-amino-2-(5-bromo-furan-2-yl)-[1,2,4]triazolo[1,5-a] pyridin-7-yl]-(2-methyl-pyrrolidin-1-yl)-methanone,
[5-amino-2-(5-bromo-furan-2-yl)-[1,2,4]triazolo[1,5-a] pyridin-7-yl]-(2,5-dihydro-pyrrol-1-yl)-methanone,
[5-amino-2-(5-bromo-furan-2-yl)-[1,2,4]triazolo[1,5-a] pyridin-7-yl]-(2,5-pyrrolidin-1-yl)-methanone,
[5-amino-2-(5-bromo-furan-2-yl)-[1,2,4]triazolo[1,5-a] pyridin-7-yl]-(2,6-morpholin-4-yl)-methanone,
[5-amino-2-(5-bromo-furan-2-yl)-[1,2,4]triazolo[1,5-a] pyridin-7-yl]-(2-methyl-piperidin-1-yl)-methanone,
[5-amino-2-(5-bromo-furan-2-yl)-[1,2,4]triazolo[1,5-a] pyridin-7-yl]-(4-methyl-piperidin-1-yl)-methanone,
[5-amino-2-(5-bromo-furan-2-yl)-[1,2,4]triazolo[1,5-a] pyridin-7-yl]-azocan-1-yl-methanone,
[5-amino-2-(5-bromo-furan-2-yl)-[1,2,4]triazolo[1,5-a] pyridin-7-yl]-(3,5-dimetyl-piperidin-1-yl)-methanone,
[5-amino-2-(5-bromo-furan-2-yl)-[1,2,4]triazolo[1,5-a] pyridin-7-yl]-[(2R,5R)-trans-2,5-dimethyl-pyrrolidin-1-yl]-methanone,
[5-amino-2-(5-bromo-furan-2-yl)-[1,2,4]triazolo[1,5-a] pyridin-7-yl]-(cis-2,6-dimethyl-morpholin-4-yl)-methanone,
[5-amino-2-(5-bromo-furan-2-yl)-[1,2,4]triazolo[1,5-a] pyridin-7-yl]-(S-2-methoxymethyl-pyrrolidin-1-yl)-methanone,
[5-amino-2-(5-bromo-furan-2-yl)-[1,2,4]triazolo[1,5-a] pyridin-7-yl]-(R-2-methoxymethyl-pyrrolidin-1-yl)-methanone,
1-[5-amino-2-(5-bromo-furan-2-yl)-[1,2,4]triazolo[1,5-a] pyridine-7-carbonyl]-L-pyrrolidine-2-carboxylic acid amide,
1-[5-amino-2-(5-bromo-furan-2-yl)-[1,2,4]triazolo[1,5-a] pyridine-7-carbonyl]-D-pyrrolidine-2-carboxylic acid amide,
1-[5-amino-2-(5-bromo-furan-2-yl)-[1,2,4]triazolo[1,5-a] pyridine-7-carbonyl]-pyrrolidine-2-carboxylic acid dimethylamide,
N-{1-[5-amino-2-(5-bromo-furan-2-yl)-[1,2,4]triazolo[1, 5-a]pyridine-7-carbonyl]-pyrrolidin-3-yl}-N-methyl-acetamide,
[5-amino-2-(5-bromo-furan-2-yl)-[1,2,4]triazolo[1,5-a] pyridin-7-yl]-(5-ethyl-2-methyl-piperidin-1-yl)-methanone or
1-[5-amino-2-(5-bromo-furan-2-yl)-[1,2,4]triazolo[1,5-a] pyridine-7-carbonyl]-piperidine-3-carboxylic acid amide.

Compounds of formula I, wherein $R^1$ is —NR'R" and R' and R" are together with the N atom to which they are attached pyrrolidinyl, piperidinyl, octahydroquinolin-1-yl, 2,5-dihydro-pyrrol-1-yl, thiazolidinyl, thiazolyl, azepan-1-yl or azocan-1-yl, and wherein the rings may be unsubstituted or substituted by lower alkyl, and $R^2$ is thiazolyl, are also preferred, for example the followings:
(5-amino-2-thiazol-2-yl-[1,2,4]triazolo[1,5-a]pyridin-7-yl)-pyrrolidin-1-yl-methanone,
(5-amino-2-thiazol-2-yl-[1,2,4]triazolo[1,5-a]pyridin-7-yl)-piperidin-1-yl-methanone,
(5-amino-2-thiazol-2-yl-[1,2,4]triazolo[1,5-a]pyridin-7-yl)-(2,5-dihydro-pyrrol-1-yl-methanone,
(5-amino-2-thiazol-2-yl-[1,2,4]triazolo[1,5-a]pyridin-7-yl)-(2-methyl-pyrrolidin-1-yl-methanone,
(5-amino-2-thiazol-2-yl-[1,2,4]triazolo[1,5-a]pyridin-7-yl)-thiazolidin-3-yl-methanone,
(5-amino-2-thiazol-2-yl-[1,2,4]triazolo[1,5-a]pyridin-7-yl)-azepan-1-yl-methanone,
(5-amino-2-thiazol-2-yl-[1,2,4]triazolo[1,5-a]pyridin-7-yl)-(2-methyl-piperidin-1-yl-methanone,
(5-amino-2-thiazol-2-yl-[1,2,4]triazolo[1,5-a]pyridin-7-yl)-(4-methyl-piperidin-1-methanone,
(5-amino-2-thiazol-2-yl-[1,2,4]triazolo[1,5-a]pyridin-7-yl)-azocan-1-yl-methanone,
(5-amino-2-thiazol-2-yl-[1,2,4]triazolo[1,5-a]pyridin-7-yl)-(3,5-dimethyl-piperidin-1-yl)-methanone,
(5-amino-2-thiazol-2-yl-[1,2,4]triazolo[1,5-a]pyridin-7-yl)-(2,6-dimethyl-piperidin-1-yl)-methanone,
(5-amino-2-thiazol-2-yl-[1,2,4]triazolo[1,5-a]pyridin-7-yl)-(cis-2,6-dimethyl-piperidin-1-yl)-methanone or
(5-amino-2-thiazol-2-yl-[1,2,4]triazolo[1,5-a]pyridin-7-yl)-(octahydro-quinolin-1-methanone.

Further preferred are compounds of formula I, wherein $R^1$ is —NR'R" and R' and R" are together with the N atom to which they are attached pyrrolidin-1-yl, azepan-1-yl, piperidin-1-yl, azocan-1-yl, and wherein the rings may be unsubstituted or substituted by lower alkyl, lower alkoxy and $R^2$ is pyridyl.

Examples of such compounds are:
(5-amino-2-pyridin-2-yl-[1,2,4]triazolo[1,5-a]pyridin-7-yl)-(2-methyl-pyrrolidin methanone,
(5-amino-2-pyridin-2-yl-[1,2,4]triazolo[1,5-a]pyridin-7-yl)-azepan-1-yl-methanone,
(5-amino-2-pyridin-2-yl-[1,2,4]triazolo[1,5-a]pyridin-7-yl)-(2-methyl-piperidin-1-yl-methanone,
(5-amino-2-pyridin-2-yl-[1,2,4]triazolo[1,5-a]pyridin-7-yl)-(2-methyl-piperidin-1-yl-methanone,
(5-amino-2-pyridin-2-yl-[1,2,4]triazolo[1,5-a]pyridin-7-yl)-azocan-1-yl-methanone,
(5-amino-2-pyridin-2-yl-[1,2,4]triazolo[1,5-a]pyridin-7-yl)-(3,5-dimethyl-piperidin-1-yl)-methanone or
(5-amino-2-pyridin-2-yl-[1,2,4]triazolo[1,5-a]pyridin-7-yl)-R-2-methoxymethyl-pyrrolidin-1-yl)-methanone.

Compounds of formula I, wherein $R^1$ is —NR'R" and R' and R" are independently from each other lower alkenyl, lower alkyl, —(CH$_2$)$_n$-cycloalkyl, —(CH$_2$)$_n$-pyridinyl or —(CH$_2$)$_n$-phenyl and $R^2$ is pyridyl are further preferred, for example the followings:
5-amino-2-pyridin-2-yl-[1,2,4]triazolo[1,5-a]pyridine-7-carboxylic acid diallylamide,
5-amino-2-pyridin-2-yl-[1,2,4]triazolo[1,5-a]pyridine-7-carboxylic acid cyclopropylmethyl-propyl-amide, 5-amino-2-pyridin-2-yl-[1,2,4]triazolo[1,5-a]pyridine-7-carboxylic acid allyl-cyclopentyl-amide, 5-amino-2-pyridin-2-yl-[1,2,4]triazolo[1,5-a]pyridine-7-carboxylic acid ethyl-pyridin-4-yl-methyl-amide, 5-amino-2-pyridin-2-yl-[1,2,4]triazolo[1,5-a]pyridine-7-carboxylic acid benzyl-isopropyl-amide or 5-amino-2-pyridin-2-yl-[1,2,4]triazolo[1,5-a]pyridine-7-carboxylic acid dibenzylamide.

Further preferred are compounds of formula I, wherein X is —N(R$^e$)CH$_2$— and R$^1$ is cycloalkyl or aryl, unsubstituted or substituted by halogen and R$^2$ is furyl, unsubstituted or substituted by halogen or methyl, or is thiazolyl.

The present compounds of formula I and their pharmaceutically acceptable salts can be prepared by methods known in the art, for example, by processes described below, which process comprises reacting a compound of formula

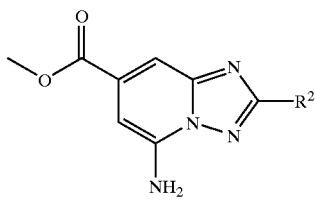

I-1 with a compound of formula

HNR'R''    II to a compound of formula

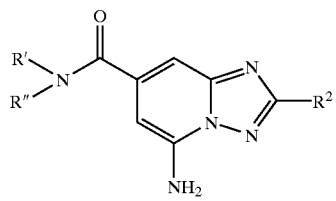

I-2 wherein R$^1$, R$^2$ and R' and R'' have the significances given above, or reacting a compound of formula

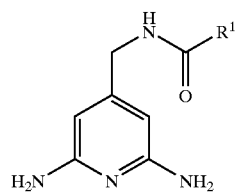

III with a compound of formula

R$^2$CHO    V in the presence of a compound of formula

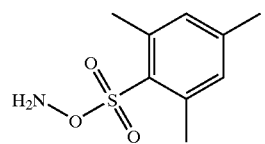

IV o give a compound of formula

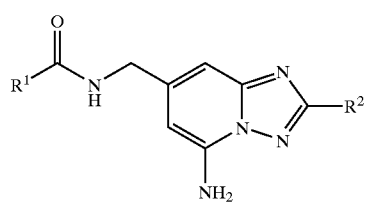

I-3 wherein R$^1$ and R$^2$ are defined above, or reacting a compound of formula

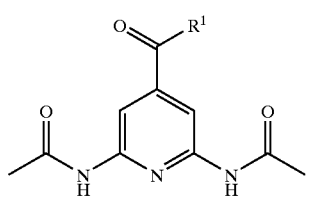

VI with HCl and then with a compound of formula

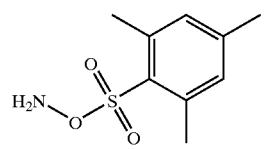

IV and with a compound of formula

R$^2$CHO    V to a compound of formula

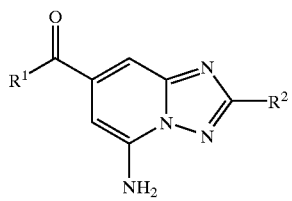

I-4 wherein R$^1$ and R$^2$ have the significances given above or modifying one or more substituents R$^1$ or R$^2$ within the definitions given above, and if desired, converting the compounds obtained into pharmaceutically acceptable acid addition salts.

In Examples 1–435 and in the following schemes 1 and 2 the preparation of compounds of formula I is described in more detail.

Scheme 1

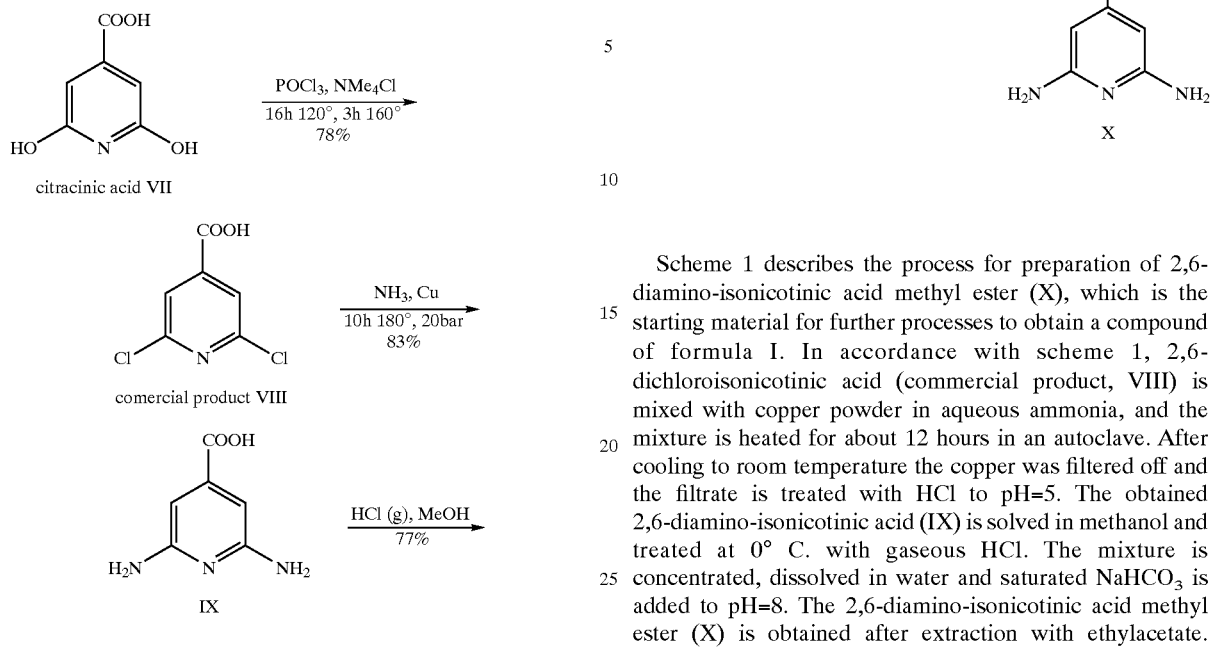
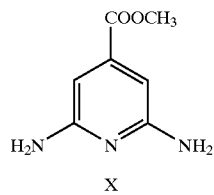

Scheme 1 describes the process for preparation of 2,6-diamino-isonicotinic acid methyl ester (X), which is the starting material for further processes to obtain a compound of formula I. In accordance with scheme 1, 2,6-dichloroisonicotinic acid (commercial product, VIII) is mixed with copper powder in aqueous ammonia, and the mixture is heated for about 12 hours in an autoclave. After cooling to room temperature the copper was filtered off and the filtrate is treated with HCl to pH=5. The obtained 2,6-diamino-isonicotinic acid (IX) is solved in methanol and treated at 0° C. with gaseous HCl. The mixture is concentrated, dissolved in water and saturated $NaHCO_3$ is added to pH=8. The 2,6-diamino-isonicotinic acid methyl ester (X) is obtained after extraction with ethylacetate.

Scheme 2

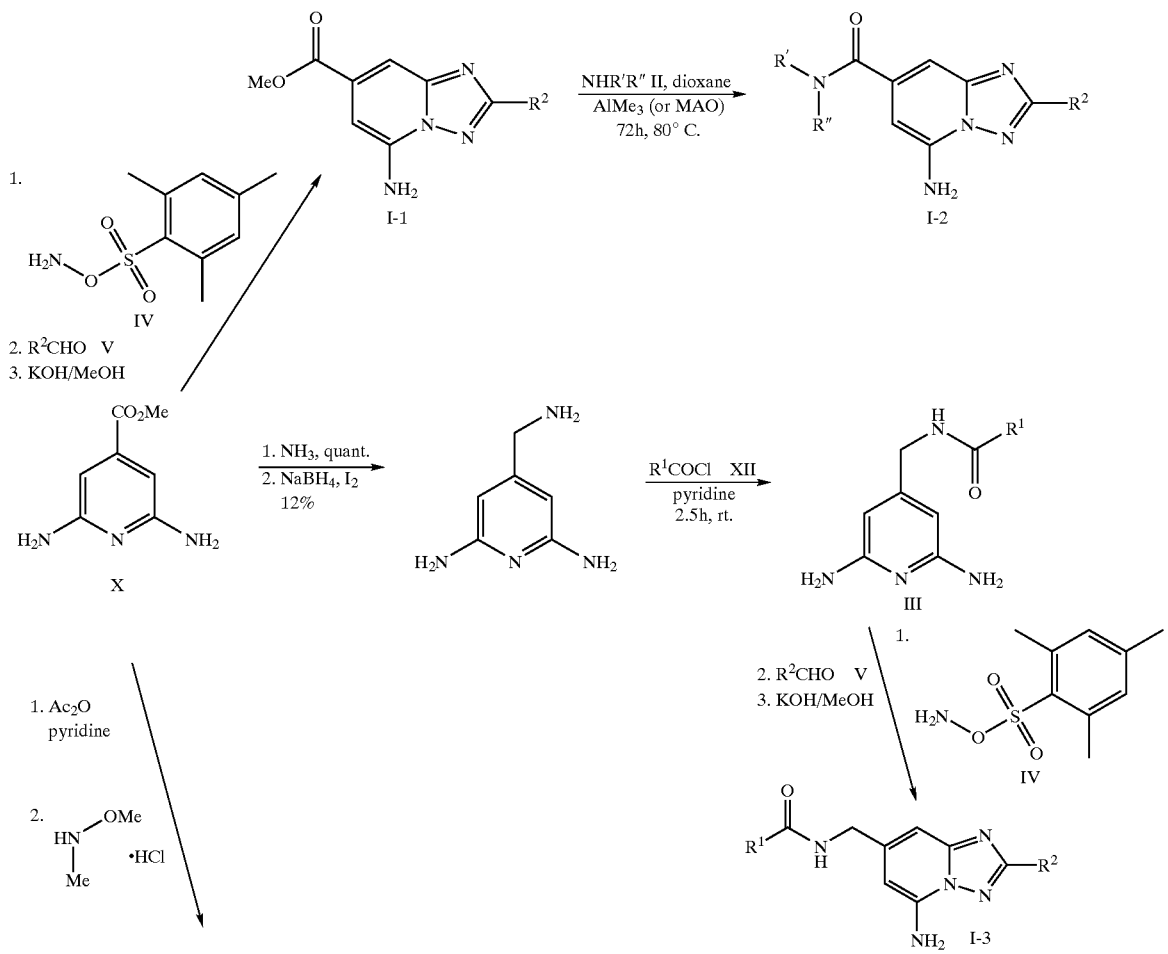

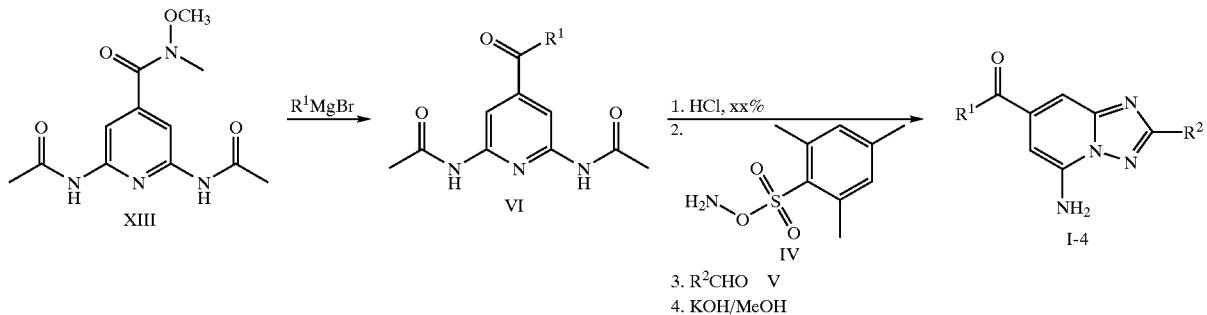

3. R²CHO V
4. KOH/MeOH

The substituents R¹ and R₂ have the significances given above.

In accordance with scheme 2 compounds of formulas I-1, I-2, I-3 and I-4 are obtained. Compounds of formula I, wherein R¹ is methoxy (I-1), may be prepared as follows: To a solution of 2,6-diamino-isonicotinic acid methyl ester (X) in dioxane is added O-mesitylenesulfonylhydroxylamine (IV) and a corresponding aldehyde (V). The mixture is stirred for some hours at about 100° C. After addition of KOH in methanol the solution is stirred at room temperature and then the product is concentrated.

The obtained compound of formula I-1 may further be transformed into a compound of formula I-2. To a solution of a compound of formula II in dioxane is added trimethylaluminum or methylaluminoxane and stirred for about 1 hour at room temperature. Then a mixture of a compound of formula I-1 in dioxane is added and the mixture is heated at about 80° C. for 72 hours. After addition of HCl the compound of formula I-2 is obtained.

A compound of formula I-3 may be prepared as follows: A solution of 2,6-diamino-isonicotinic acid methyl ester (X) is treated for 1 hour with gaseous ammonia. The mixture is heated for 36 hours at about 60° C. in an autoclave and is then filtered through decalite. The obtained 2,6-diamino-isonicotinamide is suspended in THF and borandimethylsulfide-complex (or NaBH₄) is added. The mixture is refluxed for 4 days. After cooling to room temperature HCl is added and the mixture is neutralized with NaOH, to give 4-aminomethyl-pyridine-2,6-diamine. A solution of this compound in pyridine is treated with a compound of formula XII together with a catalytic amount of 4-dimethylaminopyridine, and stirred for 2.5 hours at room temperature to obtain a compound of formula III. Furthermore, to the obtained solution of a compound of formula III in dioxane is added O-mesitylenesulfonylhydroxylamine and then an aldehyde of formula V. The mixture is heated to about 100° C. and after 2.5 hours KOH in methanol is added. After stirring the mixture at room temperature a compound of formula I-3 is obtained.

Compounds of formula I-4 may be prepared as follows: A mixture of 2,6-diamino-isonicotinic acid methyl ester (X), pyridine and acetic anhydride is stirred for 1 hour at room temperature and subsequently 1 hour at about 80° C. After purification the prepared 2,6-bis-acetylamino-isonicotinic acid methyl ester is solved in pyridine and is added slowly to a mixture of N,O-dimethylhydroxylamide and trimethylaluminum in toluene and is then allow to stir to room temperature. After purification a compound of formula XIII is obtained. Further, to a solution of 2,6-bis-acetylamino-N-methoxy-N-methyl-isonicotinamide (XIII) is added at room temperature a solution of a compound of formula R¹MgBr, for example 4-fluorophenylmagnesium bromide, in THF. The solution is stirred at room temperature and subsequently for 2 hours at about 40° C. After cooling to room temperature HCl is added and the mixture is evaporated to dryness. After purification a compound of formula VI is obtained. This compound is solved in dioxane and O-mesitylenesulfonylhydroxylamine and a compound of formula V, for example 5-bromo-2-furaldehyde, is added. The mixture is stirred at about 80° C. for 30 min, and after the addition of KOH the mixture is stirred at room temperature for some hours. After purification of the mixture a compound of formula I4 is obtained.

The salt formation is effected at room temperatures in accordance with methods which are known per se and which are familiar to any person skilled in the art. Not only salts with inorganic acids, but also salts with organic acids came into consideration. Hydrochlorides, hydrobromides, sulphates, nitrates, citrate, acetates, maleates, succinates, methan-sulphonates, p-toluenesulphonates and the like are examples of such salts.

The compounds of formula I and their pharmaceutically usable addition salts possess valuable pharmacological properties. Specifically, it has been found that the compounds of the present invention are adenosine receptor ligands.

The compounds were investigated in accordance with the tests given hereinafter.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 MM $MgCl_2$ (pH 7.4) (buffer A). The [³H]-SCH-58261 (Dionisotti et al., 1997, Br. J. Pharmacol. 121, 353) binding assay was carried out in 96-well plates in the presence of 2.5 μg of membrane protein, 0.5 mg of Ysi-poly-1-lysine SPA beads and 0.1 U adenosine deaminase in a final volume of 200 μl of buffer A. Non-specific binding was defined using xanthine amine congener (XAC; 2 μM). Compounds were tested at 10 concentrations from 10 μM–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

In accordance with the invention, it has been shown that compounds of formula I have a high affinity toward the $A_{2A}$ receptor. In the table below are described specific values of prepared compounds. Values of $KiHA_{2A}$ and $KiH_{A1}$ are shown for compounds of formula 1. A low Ki value is indicative of a particular compound's high affinity toward a particular receptor and conversely a higher Ki value is indicative of a lower affinity for that compound toward a particular receptor. A ratio obtained by dividing $KiH_{A1}$ by $KiHA_{2A}$ is then calculated. This calculated ratio provides a measure of the selectivity of the compound between the $A_{2A}$ receptor and the $A_1$ receptor. Generally speaking, compounds that have a higher $HA_1/HA_{2A}$ ratio are able to give a substantially complete blockade of the $HA_{2A}$ receptor without substantially affecting the $A_1$ receptor.

The compounds of formula I and the pharmaceutically acceptable salts of the compounds of formula I can be used as pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers and other pharmaceutically acceptable excipients for the production of pharmaceutical compositions. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier or pharmaceutically acceptable excipient are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

2,6-Diamino-isonicotinic Acid

A mixture of 20 g (0.1 mol) 2,6-dichloro isonicotinic acid and 2 g (30 mmol) copper powder in 300 ml aqueous ammonia (~30%) was heated for 12 h to 180° C. in an autoclave (20 bar). After cooling to room temperature the copper was filtered off and the filtrate was treated with 1N HCl to pH=5. The resultant precipitate was filtered and purified by repeated dissolving in aqueous ammonia (25%) and subsequent precipitation with 1N HCl. Filtration and drying in HV yielded 13.2 g (83%) 2,6-diamino-isonicotinic acid as a brown solid.

1-H-NMR (400 Mhz, DMSO-d6): δ=7.23 (s, br, 1H, COOH), 6.10 (s, 2H, Ar—H), 5.64 (s, br, 4H, $NH_2$). MS m/e (%): 153 (M+H$^+$, 100).

EXAMPLE 2

2,6-Diamino-isonicotinic Acid Methyl Ester

A suspension of 11 g (70 mmol) 2,6-diamino-isonicotinic acid in 270 ml methanol was treated at 0° C. for 2 h with gaseous HCl. The mixture was concentrated, the residue was dissolved in water and saturated $NaHCO_3$ was added to pH=8. Exhaustive extraction with ethylacetate, drying of the combined organic phases with $MgSO_4$ and removal of the volatiles yielded 9.3 g (77%) 2,6-diamino-isonicotinic acid methyl ester as yellow solid.

1-H-NMR (400 MHz, DMSO-d6): δ=6.11 (s, 2H, Ar—H), 5.69 (s, 4H, $NH_2$), 3.77 (s, 3H, $CH_3$). MS m/e (%): 167 (M+H$^+$, 100). Elemental analysis: calculated C, 50.30, H, 5.43, N, 25.14. found C, 50.27, H, 5.26, N, 24.11.

EXAMPLE 3

General Procedure

5-Amino-2-phenyl-[1,2,4]triazolo[1,5-a]pyridine-7-carboxylic Acid Methyl Ester

To a solution of 1 g (5.98 mmol) 2,6-diamino-isonicotinic acid methyl ether in 50 ml dioxane at room temperature was added 1.41 g (6.58 mmol, 1.1 eq.) O-mesitylenesulfonylhydroxylamine and after 2 h 0.824 g (7.77 mmol, 1.3 eq.) benzaldehyde and stirred for 3 h at 100° C. After the addition of 6 ml 1N KOH in methanol the mixture was stirred at room temperature for 12 h and concentrated. The residue was taken up in 50 ml water followed by extraction with dichloromethane, drying of the combined organic layers with $MgSO_4$, and removal of the volatile components. The residue was purified by column chromatography on silica eluting with a gradient of dichloromethane:ethylacetate 10:1->5:1. 0.8 g (50%) of the title compound were isolated as brownish solid.

According to example 3 triazolopyridine methylester derivatives have been synthesised. The results including structural formulae and characterization are compiled in the following list comprising examples 4 to example 19

| No | Structure | Yield (%) | MW MS m/e (%) | Composition Calc./found | NMR-data |
|---|---|---|---|---|---|
| 4 | 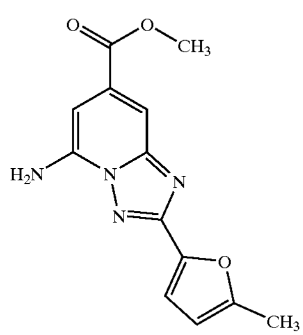 | 50 | 272.2 (M + H)$^+$ (100) | C 57.35/57.46 H 4.44/4.61 N 20.58/20.08 | 1-H-NMR(400 MHz, DMSO-d$_6$): δ=7.38(s, 3H, 8-H, $NH_2$), 7.08(s, 1H, Furanyl(3-H)), 6.73(s, 1H, 6-H)), 6.34(s, 1H, Furanyl(4-H)), 3.89(s, 3H, $OCH_3$), 2.40(s, 3H, Furanyl($CH_3$)) |
| 5 | 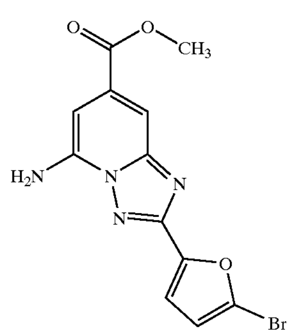 | 27 | 337.1 (M + H)$^+$ (100) | C 42.75/42.86 H 2.69/2.99 N 16.62/16.12 Br 23.70/24.79 | 1-H-NMR(400 MHz, DMSO-d$_6$): δ=7.45(s, br, 2H, $NH_2$), 7.42(s, 1H, 8-H), 7.23(d, J=2 Hz, 1H, Furanyl(3-H)), 6.85(d, J= 2 Hz, 1H, Furanyl(4-H)), 6.76(s, 1H), 6-H), 3.90(s, 3H, $OCH_3$) |
| 6 | 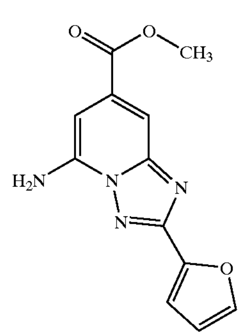 | 43 | 258.239 (M + H)$^+$ (100) | C 55.81/55.70 H 3.90/4.37 N 21.70/19.91 | 1-H-NMR(400 MHz, DMSO-d$_6$): δ=7.93(s, 1H, Furanyl(3-H), 7.42(s, 1H, 8-H), 7.40(s, 2H, $NH_2$), 7.19(s, 1H, Furanyl(5-H)), 6.75(s, 1H, 6-H), 6.72 (s, 1H, Furanyl(4-H)) 3.90(s, 3H, $OCH_3$) |

-continued

| No | Structure | Yield (%) | MW MS m/e (%) | Composition Calc./found | NMR-data |
|---|---|---|---|---|---|
| 7 | 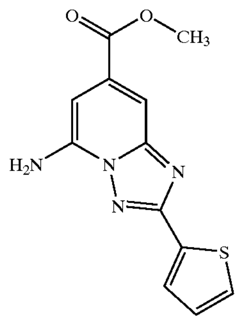 | 32 | 274.303 (M + H)+ (100) | C 52.55/52.84 H 3.67/3.83 N 20.43/19.57 S 11.69/11.92 | 1-H-NMR(400 MHz, DMSO-d$_6$): δ=7.84(d, J= 1 Hz, 1H, Thiophenyl(3-H)), 7.75(d, J=4Hz, 1H, Thiophenyl(5-H)), 7.42(s, 1 H, 8-H), 7.34(s, 2H, NH$_2$), 7.25(m, 1H, Thiophenyl(4-H)), 6.75(s, 1H, 6-H), 3.90(s, 3H, OCH$_3$) |
| 8 | 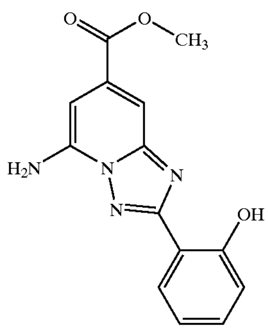 | 18 | 284.277 (M + H)+ (100) | C 59.15/60.07 H 4.26/4.40 N 19.71/18.26 | 1-H-NMR(400 MHz, DMSO-d$_6$): δ=11.1(s, 1H, OH), 8.20(d, J=8 Hz, 1H, Ph(6-H)), 7.64(s, br, 2H, NH$_2$), 7.51(s, 1H, 8-H), 7.41(t, J=8 Hz, 1H, Ph(5-H)), 7.03(m, 2H, Ph(3-H, 4-H)), 6.83(s, 1H, 6-H), 3.91(s, 3H, OCH$_3$) |
| 9 | 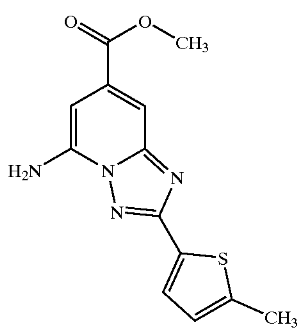 | 49 | 288.33 (M + H)+ (100) | C 54.16/53.77 H 4.20/4.29 N 19.43/18.85 S 11.12/11.08 | 1-H-NMR(400 MHz, DMSO-d$_6$): δ=7.64(d, J= 3.6 Hz, 1H, Thiophenyl(3-H)), 7.39(s, 1H, 8-H), 7.30 (s, br, 2H, NH$_2$), 6.93(d, J=3.6 Hz, 1H, Thiophenyl (4-H)), 6.73(s, 1H, 6-H), 3.89(s, 3H, OCH$_3$) |
| 10 | 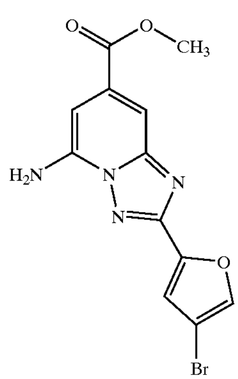 | 24 | 337.14 (M + H)+ (100) | C 42.75/42.88 H 2.69/2.93 N 16.62/16.15 Br 23.70/23.67 | 1-H-NMR(400 MHz, DMSO-d$_6$): δ=8.19(s, 1H, Furanyl(3-H)), 7.44(s, br, 3H, NH$_2$, 8-H), 7.34(s, 1H, Furanyl(5-H)), 6.77(s, 1H, 6-H), 3.90(s, 3H, OCH$_3$) |

| No | Structure | Yield (%) | MW MS m/e (%) | Composition Calc./found | NMR-data |
|----|-----------|-----------|---------------|-------------------------|----------|
| 11 | 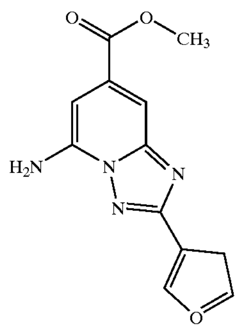 | 51 | 258.239 (M+H)+ (100) | C 55.81/55.89 H 3.90/4.04 N 21.70/21.20 | 1-H-NMR(400 MHz, DMSO-d<sub>6</sub>): δ= 8.38(s, 1H, Furanyl(2-H)), 7.87(s, 1H, Furanyl(4-H)), 7.41 (s, 1H, 8-H), 7.32(s, br, 2H, NH<sub>2</sub>), 7.02(s, 1H, Furanyl(5-H)), 6.73(s, 1H, 6-H), 3.90(s, 3H, OCH<sub>3</sub>) |
| 12 | 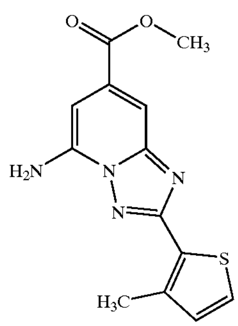 | 43 | 288.33 (M + H)+ (100) | C 54.16/54.42 H 4.20/4.33 N 19.43/18.82 S 11.12/11.23 | 1-H-NMR(400 MHz, DMSO-d$_6$): δ=7.61(d, J= 5.2 Hz, 1H, Thiophenyl(5-H)), 7.42(s, 1H, 8-H), 7.30 (s, br, 2H, NH$_2$), 7.07(d, J=5.2 Hz, 1H, Thiophenyl (4-H)), 6.74(s, 1H, 6-H), 3.90(s, 3H, OCH$_3$) |
| 13 | 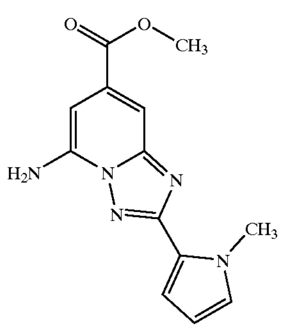 | 28 | 271.281 (M + H)+ (100) | C 57.56/57.59 H 4.83/5.02 N 25.82/25.53 | 1-H-NMR(400 MHz, DMSO-d$_6$): δ=7.39(s, 1H, 8-H), 7.29(s, br, 2H, NH$_2$), 6.98(s, 1H, Pyrrolyl (3-H)), 6.84(s, 1H, Pyrrolyl(5-H)), 6.71(s, 1H, 6-H), 6.14(m, 1H, Pyrrolyl(4-H), 4.08(s, 3H, NCH$_3$), 3.89(s, 3H, OCH$_3$) |
| 14 | 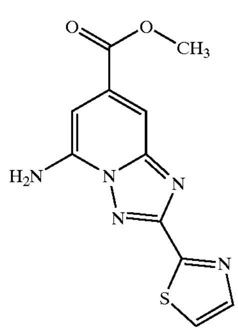 | 51 | 275.291 (M + H)+ (100) | C 47.99/48.27 H 3.30/3.51 N 25.44/24.49 S 11.65/10.69 | 1-H-NMR(400 MHz, DMSO-d$_6$): δ=8.09(d, J= 2.8 Hz, 1H, Thiazolyl(5-H)), 8.01(d, J=2.8 Hz, 1H, Thiazolyl(4-H)), 7.51 (s, br, 2H, NH$_2$), 7.50(s, 1H, 8-H), 6.81(s, 1H, 6-H), 3.91(s, 3H, OCH$_3$) |

| No | Structure | Yield (%) | MW MS m/e (%) | Composition Calc./found | NMR-data |
|---|---|---|---|---|---|
| 15 | 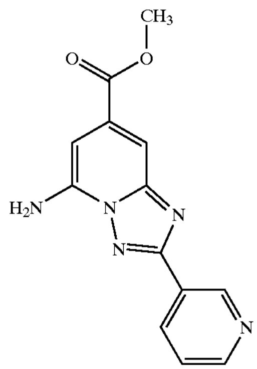 | | 269.265 (M + H)+ (100) | | |
| 16 | 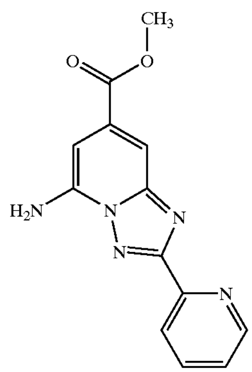 | | 269.265 (M + H)+ (100) | | 1-H-NMR(250 MHz, DMSO-d₆): δ=8.75(d, J = 4.2 Hz, 1H, pyridine 6-H), 8.31(d, J=7.8 Hz, 1H, pyridine 3-H), 8.01(t, J = 7.8 Hz, 1H, pyridine 4-H), 7.56(t, J=4.2 Hz, 1H, pyridine 5-H), 7.50(d, J= 1.5 Hz, 1H, 4-H), 7.46(s, br, 2H, NH₂), 6.78(d, J= 1.5 Hz, 1H, 6-H), 3.91(s, 3H, OCH₃) |
| 17 | 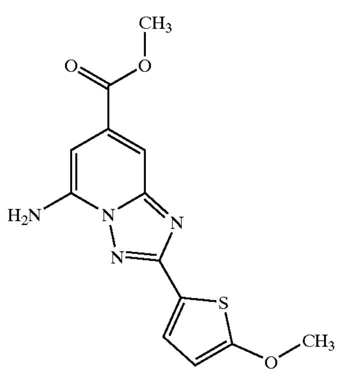 | | 304.33 (M + H)+ (100) | | 1-H-NMR(250 MHz, DMSO-d₆): δ=7.81(d, J= 4.3 Hz, 1H, thiophene 3-H), 7.35(d, J=1.7 Hz, 1H, 4-H), 7.28(s, br, 2H, NH₂), 6.71(d, J=1.7 Hz, 1H, 6-H), 6.59(d, J=4.3 Hz, 1H, thiophene 4-H), 3.91(s, 3H, OCH₃) |

-continued

| No | Structure | Yield (%) | MW MS m/e (%) | Composition Calc./found | NMR-data |
|---|---|---|---|---|---|
| 18 | 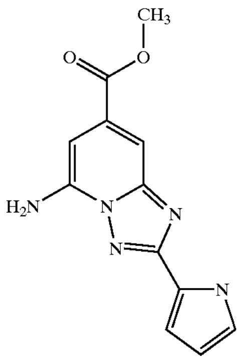 | | 257.254 (M + H)+ (100) | | |
| 19 | 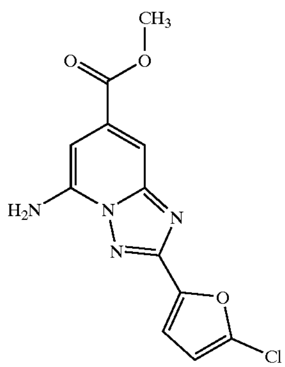 | | 292.684 (M + H)+ (100) | | 1-H-NMR(250 MHz, DMSO-d$_6$): δ=7.45(s, br, 2H, NH$_2$), 7.41(s, 1H, H-4), 7.28(d, J=3.6 Hz, 1H, furyl 3-H), 6.76(m, 2H, 6-H/thiophene 3-H), 3.90 (s, 3H, OCH$_3$) |

The examples 4–19 are named as follows:

| Example No. | Name |
|---|---|
| 4 | 5-Amino-2-(5-methyl-furan-2-yl)-[1,2,4]triazolo[1,5-a]pyridine-7-carboxylic acid methyl ester |
| 5 | 5-Amino-2-(5-bromo-furan-2-yl)-[1,2,4]triazolo[1,5-a]pyridine-7-carboxylic acid methyl ester |
| 6 | 5-Amino-2-furan-2-yl-[1,2,4]triazolo[1,5-a]pyridine-7-carboxylic acid methyl ester |
| 7 | 5-Amino-2-thiophen-2-yl-[1,2,4]triazolo[1,5-a]pyridine-7-carboxylic acid methyl ester |
| 8 | 5-Amino-2-(2-hydroxy-phenyl)-[1,2,4]triazolo[1,5-a]pyridine-7-carboxylic acid methyl ester |
| 9 | 5-Amino-2-(5-methyl-thiophen-2-yl)-[1,2,4]triazolo[1,5-a]pyridine-7-carboxylic acid methyl ester |
| 10 | 5-Amino-2-(4-bromo-furan-2-yl)-[1,2,4]triazolo[1,5-a]pyridine-7-carboxylic acid methyl ester |
| 11 | 5-Amino-2-furan-3-yl-[1,2,4]triazolo[1,5-a]pyridine-7-carboxylic acid methyl ester |
| 12 | 5-Amino-2-(3-methyl-thiophen-2-yl)-[1,2,4]triazolo[1,5-a]pyridine-7-carboxylic acid methyl ester |
| 13 | 5-Amino-2-(1-methyl-1H-pyrrol-2-yl)-[1,2,4]triazolo[1,5-a]pyridine-7-carboxylic acid methyl ester |
| 14 | 5-Amino-2-thiazol-2-yl-[1,2,4]triazolo[1,5-a]pyridine-7-carboxylic acid methyl ester |
| 15 | 5-Amino-2-pyridin-3-yl-[1,2,4]triazolo[1,5-a]pyridine-7-carboxylic acid methyl ester |
| 16 | 5-Amino-2-pyridin-2-yl-[1,2,4]triazolo[1,5-a]pyridine-7-carboxylic acid methyl ester |
| 17 | 5-Amino-2-(5-methoxy-thiophen-2-yl)-[1,2,4]triazolo[1,5-a]pyridine-7-carboxylic acid methyl ester |
| 18 | 5-Amino-2-(1H-pyrrol-2-yl)-[1,2,4]triazolo[1,5-a]pyridine-7-carboxylic acid methyl ester |
| 19 | 5-Amino-2-(5-chloro-furan-2-yl)-[1,2,4]triazolo[1,5-a]pyridine-7-carboxylic acid methyl ester |

EXAMPLE 20

5-Amino-2-(5-methyl-furan-2-yl)-[1,2,4]triazolo[1,5-a]pyridine-7-carboxylic Acid Diethylamide To a solution of 35 mg (0.44 mmol) diethylamine in 0.5 ml dioxane was added 0.5 ml methylaluminoxane (10% in toluene) (in a variant trimethylaluminium was used instead of methylaluminoxane which proofed to give comparable results) and stirred for 1 h at room temperature. 31 mg (0.11 mmol) 5-Amino-2-(5-methyl-furan-2-yl)-[1,2,4]triazolo[1,5-a]pyridine-7-carboxylic acid methyl ester in 1 ml dioxane was added and the mixture was heated to 80° C. for 72 h. After addition of 0.4 ml 1N HCl the mixture was evaporated to dryness and the residue was taken up in 1.5 ml DMSO, filtered, and the title compound was isolated by reversed phase HPLC eluting with a water/acetonitrile gradient to yield 8.6 mg (25%).

1-H-NMR (500 MHz, DMSO): δ=7.24 (s, 2H, NH$_2$), 7.03 (d, J=3 Hz, 1H, Furanyl (3-H)), 6.79 (s, 1H, 8-H), 6.32 (d, J=3 Hz, 1H, Furanyl (4-H)), 6.09 (s, 1H, 6-H), 2.39 (s, 3H, CH$_3$), 1.15 (m, 3H, NCH$_2$CH$_3$), 1.08 (m, 3H, NCH$_2$CH$_3$), signal for NCH$_2$ under DMSO signal. MS m/e (%): 313 (M$^+$, 100)

According to example 20, representative triazolopyridine carboxamide derivatives have been synthesised. The results including structural formulae and characterization are compiled in the following list comprising examples 21 to example 233. Additionally, the table includes the affinity values HA$_2$a and HA$_1$ adenosine receptors determined as described above. The calculated selectivity ratio of the affinity to the HA1 receptor to the HA2a receptor provides a selectivity value indicative of the ability of the compound to block the HA2A receptor compared to its effect on the HA1 receptor.

| No. | Ki HA2A (nM) | Ki HA1 (nM) | selectivity (A1/A2a) | Structure | MW MS m/e (%) |
|---|---|---|---|---|---|
| 21 | 3.4 | 232.1 | 68.0 | 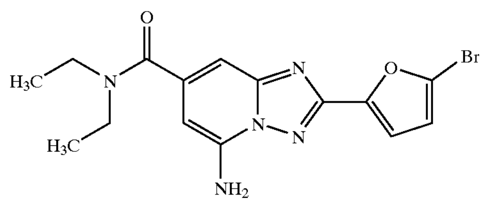 | 329.4 MH$^+$ (100) |
| 22 | 8.8 | 548.1 | 62.0 | 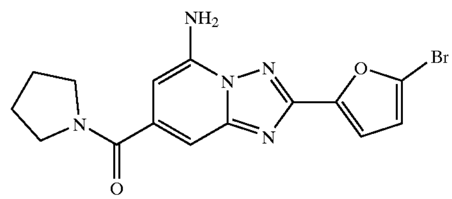 | 376.2 MH$^+$ (100) |
| 23 | 5.8 | 275.6 | 47.9 | 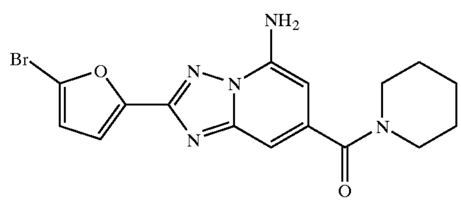 | 390.2 MH$^+$ (100) |
| 24 | 8.9 | 247.3 | 27.8 | 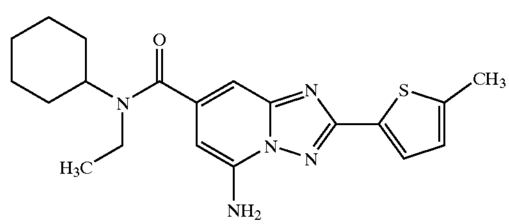 | 383.5 MH$^+$ (100) |
| 25 | 50.4 | 3100.3 | 61.5 | 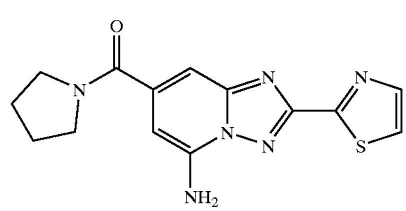 | 314.4 MH$^+$ (100) |
| 26 | 2.3 | 30.1 | 13.0 | 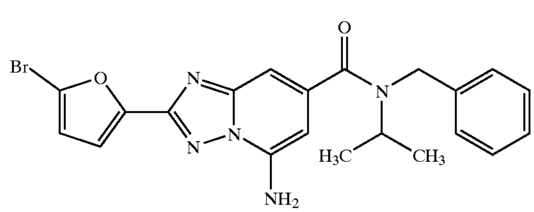 | 454.3 MH$^+$ (100) |

-continued

| No. | Ki HA2A (nM) | Ki HA1 (nM) | selectivity (A1/A2a) | Structure | MW MS m/e (%) |
|---|---|---|---|---|---|
| 27 | 16.8 | 940.3 | 56.0 | 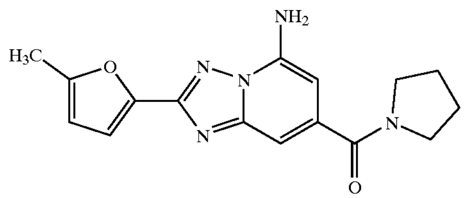 | 311.3 MH+ (100) |
| 28 | 14.2 | 696.1 | 49.1 | 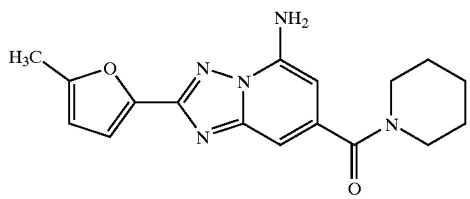 | 325.4 MH+ (100) |
| 29 | 15.9 | 243.6 | 15.3 | 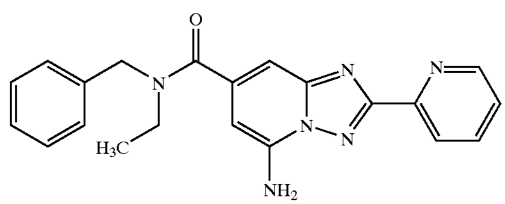 | 372.4 MH+ (100) |
| 30 | 211.7 | 2138.3 | 10.1 | 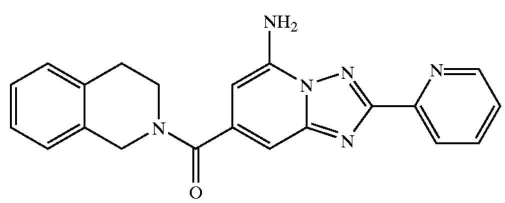 | 370.4 MH+ (100) |
| 31 | 49.6 | 1126.6 | 22.7 | 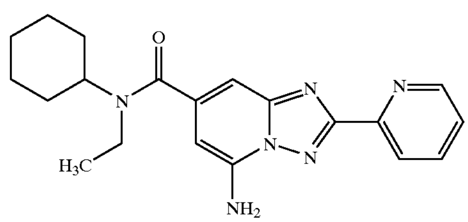 | 364.5 MH+ (100) |
| 32 | 28.6 | 288.0 | 10.1 | 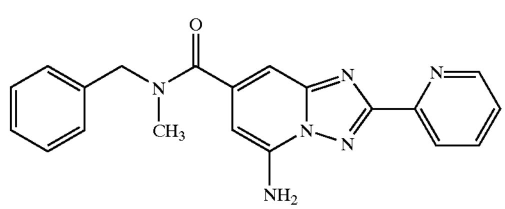 | 358.4 MH+ (100) |
| 33 | 87.0 | 1173.1 | 13.5 | 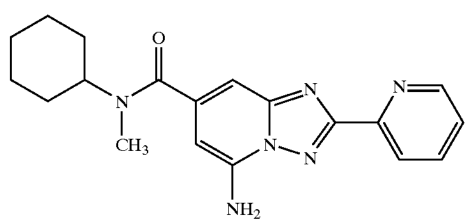 | 350.4 MH+ (100) |

-continued
| No. | Ki HA2A (nM) | Ki HA1 (nM) | selectivity (A1/A2a) | Structure | MW MS m/e (%) |
|---|---|---|---|---|---|
| 34 | 153.9 | 5977.2 | 38.8 | 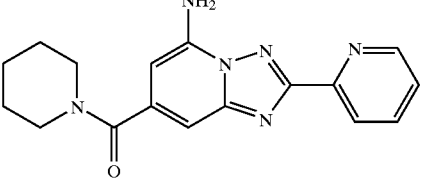 | 322.4 MH+ (100) |
| 35 | 106.1 | 2917.2 | 27.5 | 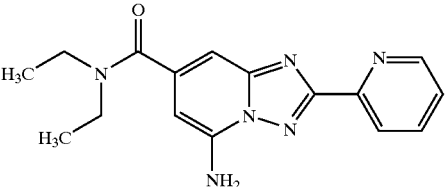 | 310.4 MH+ (100) |
| 36 | 13.1 | 199.2 | 15.2 | 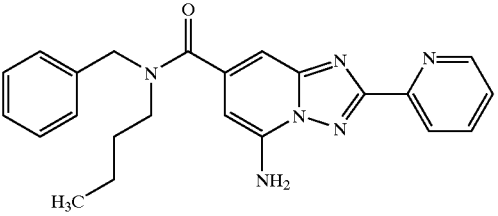 | 400.5 MH+ (100) |
| 37 | 374.6 | | 0.0 | 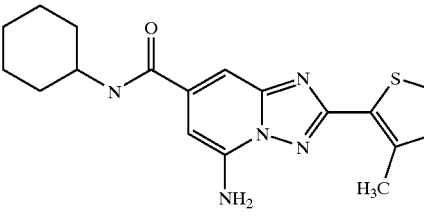 | 355.5 MH+ (100) |
| 38 | 23.8 | 108.9 | 4.6 | 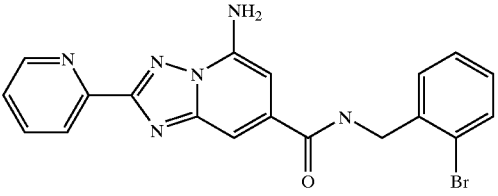 | 423.3 MH+ (100) |
| 39 | 16.8 | 69.8 | 4.2 | 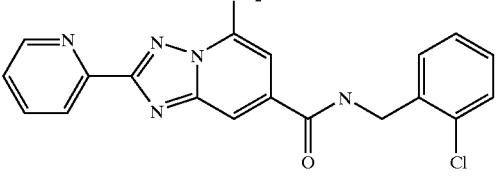 | 378.8 MH+ (100) |
| 40 | 49.9 | 204.2 | 4.1 | 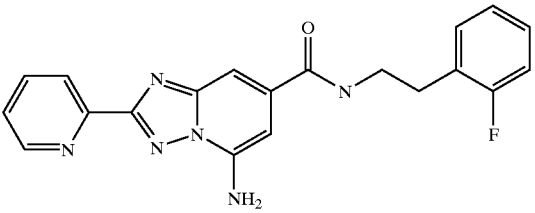 | 376.4 MH+ (100) |

-continued

| No. | Ki HA2A (nM) | Ki HA1 (nM) | selectivity (A1/A2a) | Structure | MW MS m/e (%) |
|---|---|---|---|---|---|
| 41 | 21.8 | 88.1 | 4.0 | 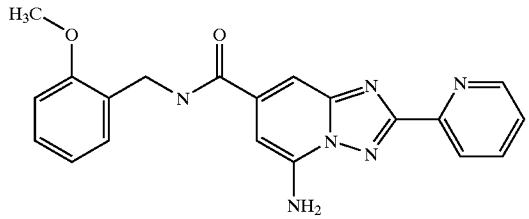 | 374.4 MH+ (100) |
| 42 | 341.1 | | 0.0 | 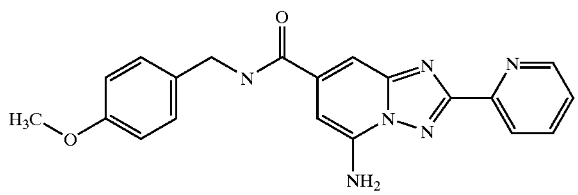 | 374.4 MH+ (100) |
| 43 | 87.7 | 203.3 | 2.3 | 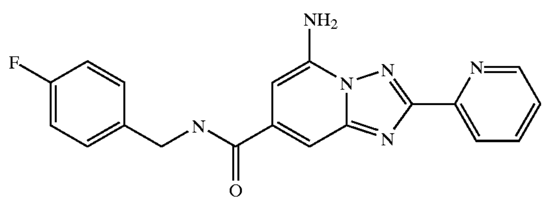 | 362.4 MH+ (100) |
| 44 | 44.5 | 120.4 | 2.7 | 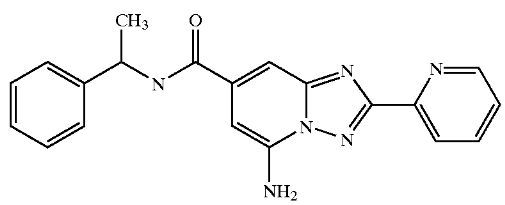 | 358.4 MH+ (100) |
| 45 | 53.5 | 127.6 | 2.4 | 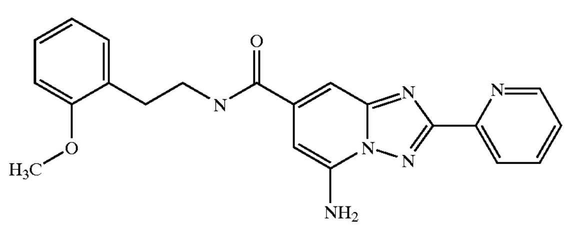 | 388.4 MH+ (100) |
| 46 | 61.1 | 184.0 | 3.0 | 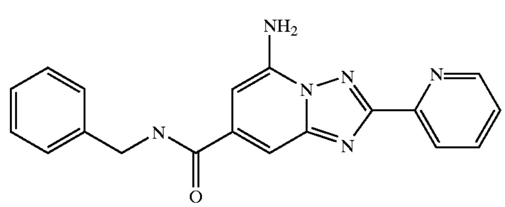 | 344.4 MH+ (100) |
| 47 | 37.5 | 316.2 | 8.4 | 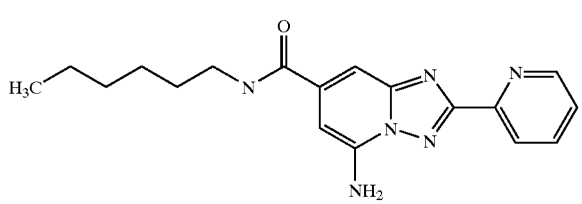 | 338.4 MH+ (100) |

-continued

| No. | Ki HA2A (nM) | Ki HA1 (nM) | selectivity (A1/A2a) | Structure | MW MS m/e (%) |
|---|---|---|---|---|---|
| 48 | 62.1 | 365.9 | 5.9 | 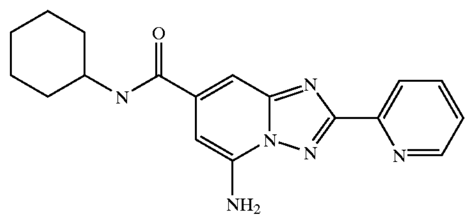 | 336.4 MH+ (100) |
| 49 | 34.3 | 242.1 | 7.1 | 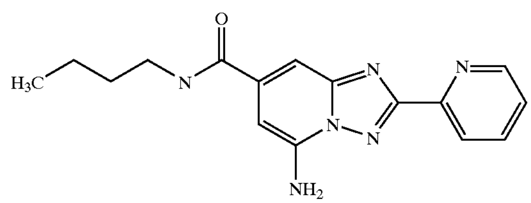 | 310.4 MH+ (100) |
| 50 | 118.9 | 123.2 | 1.0 | 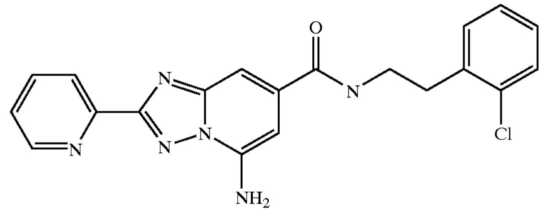 | 392.9 MH+ (100) |
| 51 | 22.2 | 129.1 | 5.8 | 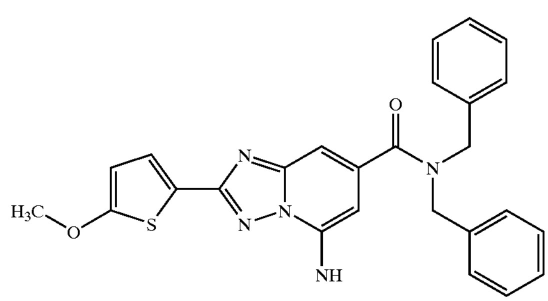 | 469.6 MH+ (100) |
| 52 | 108.1 | 85.7 | 0.8 | 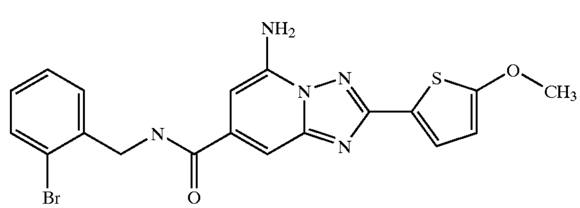 | 458.3 MH+ (100) |
| 53 | 326.8 | | 0.0 | 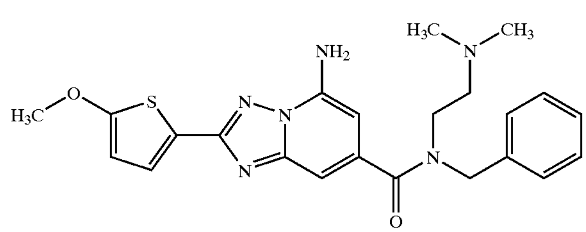 | 450.6 MH+ (100) |

-continued

| No. | Ki HA2A (nM) | Ki HA1 (nM) | selectivity (A1/A2a) | Structure | MW | MS m/e (%) |
|---|---|---|---|---|---|---|
| 54 | 314.7 |  | 0.0 | 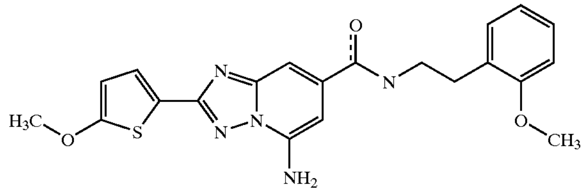 | 423.5 | MH+ (100) |
| 55 | 28.3 | 76.4 | 2.7 | 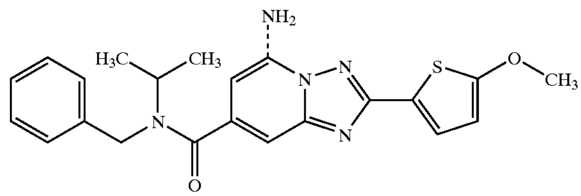 | 421.5 | MH+ (100) |
| 56 | 82.0 | 86.3 | 1.1 | 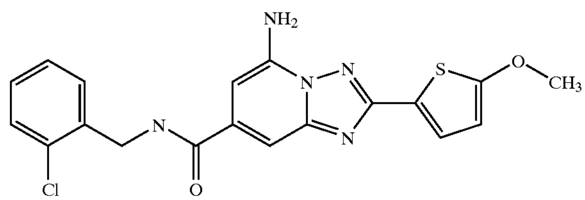 | 413.9 | MH+ (100) |
| 57 | 337.4 |  | 0.0 | 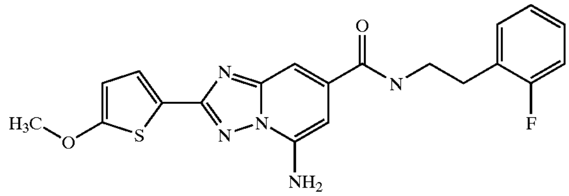 | 411.5 | MH+ (100) |
| 58 | 71.9 | 52.7 | 0.7 | 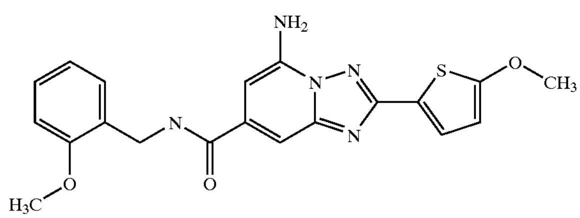 | 409.5 | MH+ (100) |
| 59 | 42.9 | 106.4 | 2.5 | 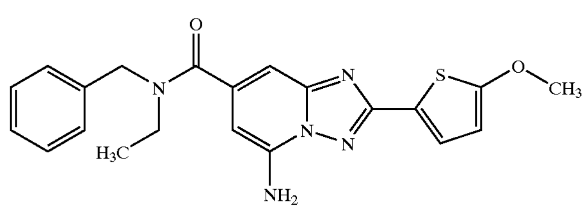 | 407.5 | MH+ (100) |
| 60 | 391.7 |  | 0.0 | 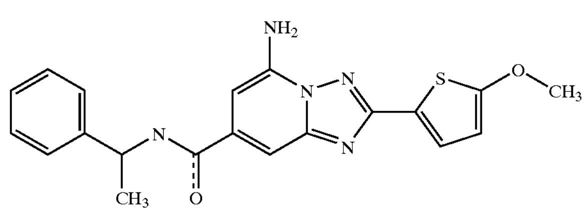 | 393.5 | MH+ (100) |

-continued

| No. | Ki HA2A (nM) | Ki HA1 (nM) | selectivity (A1/A2a) | Structure | MW MS m/e (%) |
|---|---|---|---|---|---|
| 61 | 333.1 | | 0.0 | 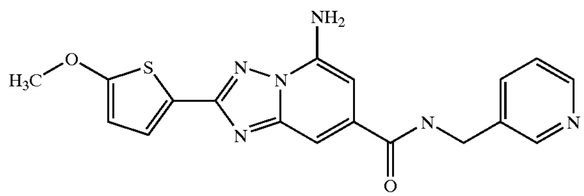 | 380.4 MH+ (100) |
| 62 | 175.5 | 113.0 | 0.6 | 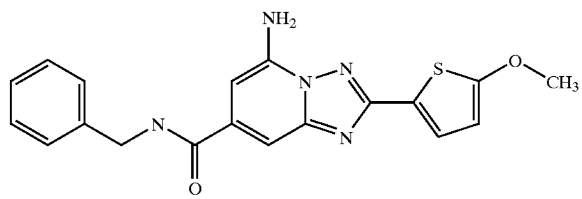 | 379.4 MH+ (100) |
| 63 | 181.3 | 247.0 | 1.4 | 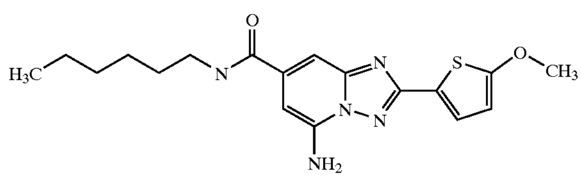 | 373.5 MH+ (100) |
| 64 | 227.0 | 222.8 | 1.0 | 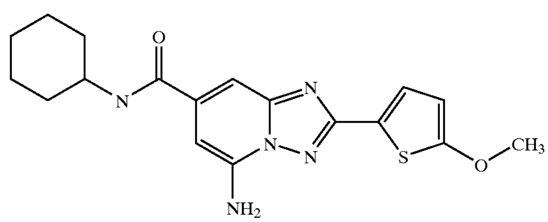 | 371.5 MH+ (100) |
| 65 | 51.5 | 210.7 | 4.1 | 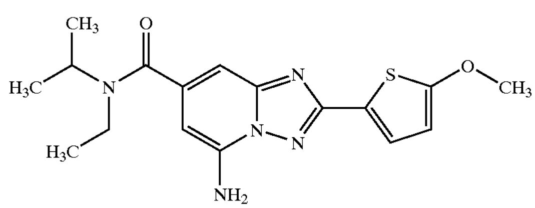 | 359.5 MH+ (100) |
| 66 | 173.7 | 622.9 | 3.6 | 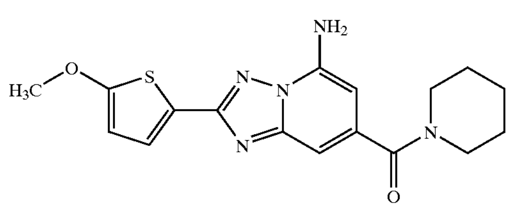 | 357.4 MH+ (100) |
| 67 | 99.1 | 135.6 | 1.4 | 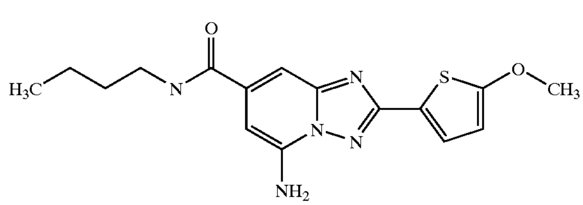 | 345.4 MH+ (100) |

-continued

| No. | Ki HA2A (nM) | Ki HA1 (nM) | selectivity (A1/A2a) | Structure | MW MS m/e (%) |
|---|---|---|---|---|---|
| 68 | 171.2 | 716.9 | 4.2 | 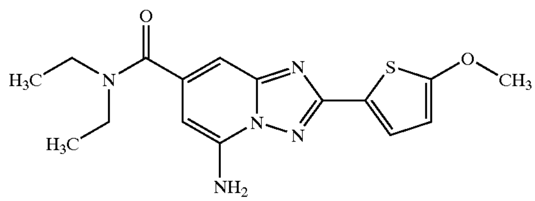 | 345.4 MH+ (100) |
| 69 | 338.9 | | 0.0 | 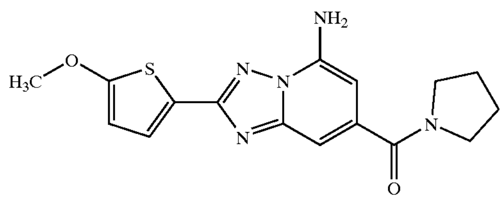 | 343.4 MH+ (100) |
| 70 | 112.6 | 148.3 | 1.3 | 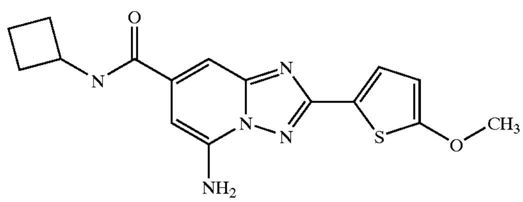 | 343.4 MH+ (100) |
| 71 | 64.9 | 180.3 | 2.8 | 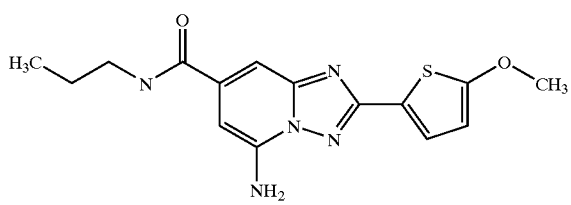 | 331.4 MH+ (100) |
| 72 | 260.2 | | 0.0 | 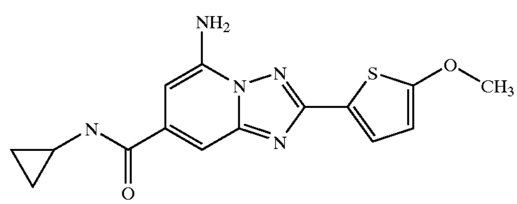 | 329.4 MH+ (100) |
| 73 | 37.4 | 136.2 | 3.6 | 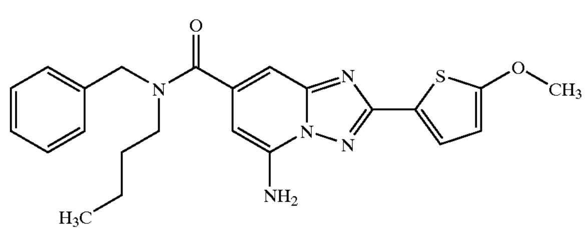 | 435.6 MH+ (100) |
| 74 | 366.8 | | 0.0 | 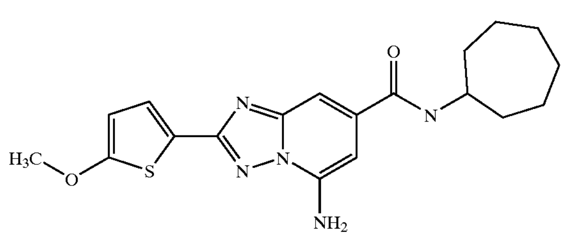 | 385.5 MH+ (100) |

-continued

| No. | Ki HA2A (nM) | Ki HA1 (nM) | selectivity (A1/A2a) | Structure | MW MS m/e (%) |
|---|---|---|---|---|---|
| 75 | 26.6 | 15.8 | 0.6 | 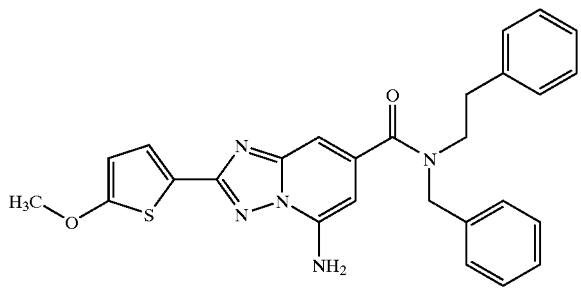 | 483.6 MH+ (100) |
| 76 | 28.5 | | 0.0 | 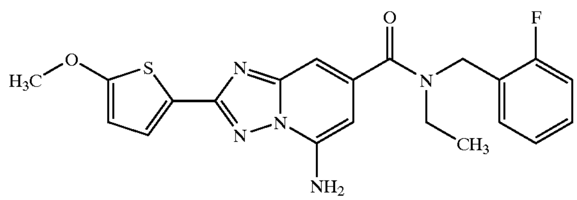 | 425.5 MH+ (100) |
| 77 | 116.1 | 294.8 | 2.5 | 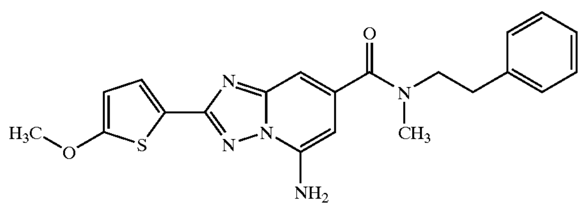 | 407.5 MH+ (100) |
| 78 | 388.7 | 97.4 | 0.3 | 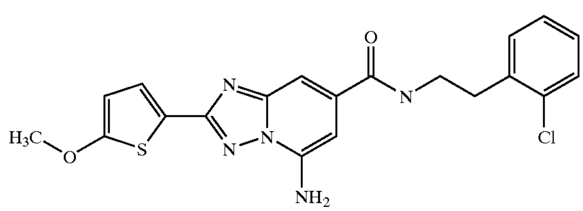 | 427.9 MH+ (100) |
| 79 | 152.1 | 1399.7 | 9.2 | 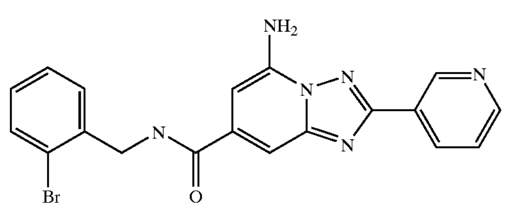 | 423.3 MH+ (100) |
| 80 | 282.1 | 3773.8 | 13.4 | 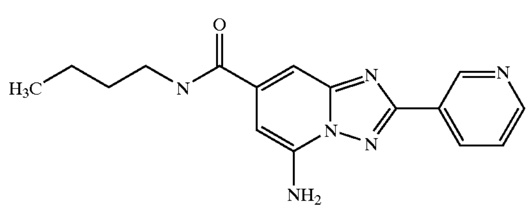 | 310.4 MH+ (100) |

-continued
| No. | Ki HA2A (nM) | Ki HA1 (nM) | selectivity (A1/A2a) | Structure | MW MS m/e (%) |
|---|---|---|---|---|---|
| 81 | 315.0 | 4391.4 | 13.9 | 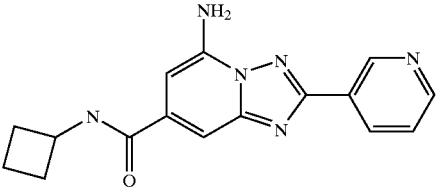 | 308.3 MH+ (100) |
| 82 | 308.7 | 5846.9 | 18.9 | 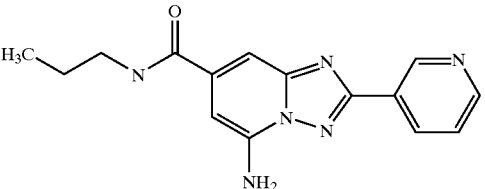 | 296.3 MH+ (100) |
| 83 | 129.7 | 1499.0 | 11.6 | 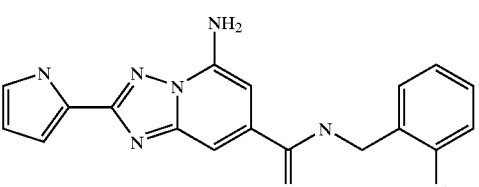 | 366.8 MH+ (100) |
| 84 | 293.9 | 4962.4 | 16.9 | 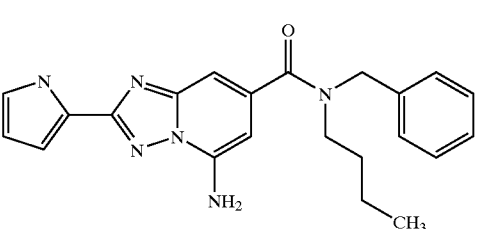 | 388.5 MH+ (100) |
| 85 | 168.7 | 1399.7 | 8.3 | 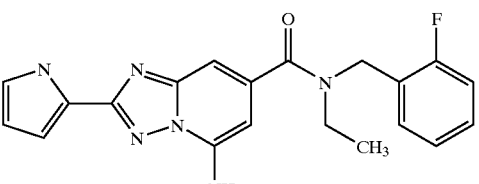 | 378.4 MH+ (100) |
| 86 | 252.4 | 819.3 | 3.2 | 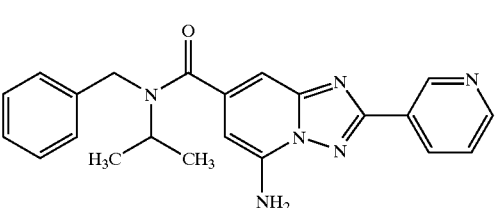 | 386.5 MH+ (100) |
| 87 | 239.6 | 1256.9 | 5.2 | 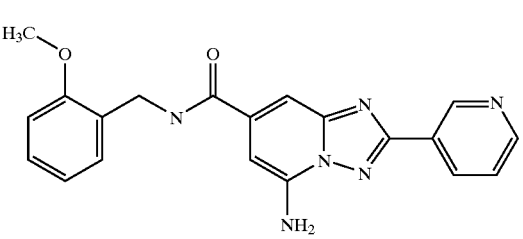 | 374.4 MH+ (100) |

-continued

| No. | Ki HA2A (nM) | Ki HA1 (nM) | selectivity (A1/A2a) | Structure | MW MS m/e (%) |
|---|---|---|---|---|---|
| 88 | 277.8 | 993.1 | 3.6 | 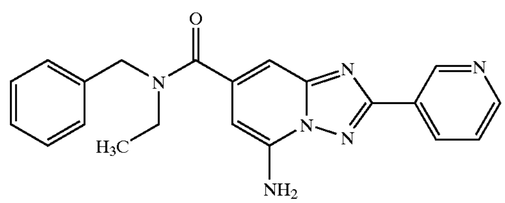 | 372.4 MH+ (100) |
| 89 | 174.0 | 900.0 | 5.2 | 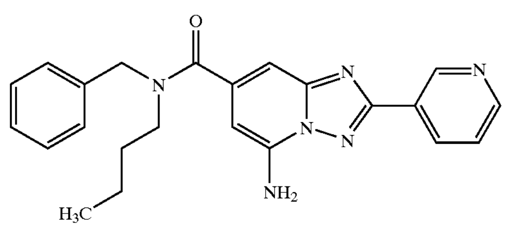 | 400.5 MH+ (100) |
| 90 | 144.1 | 239.3 | 1.7 | 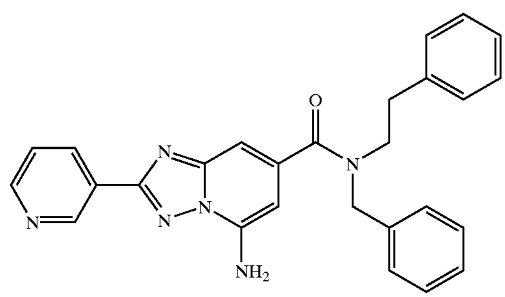 | 448.5 MH+ (100) |
| 91 | 144.1 | 815.0 | 5.7 | 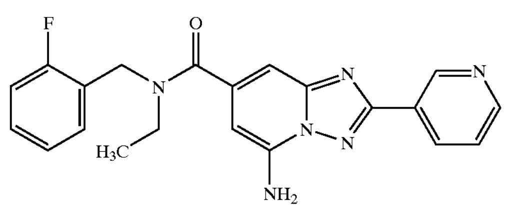 | 390.4 MH+ (100) |
| 92 | 293.1 | | 0.0 | 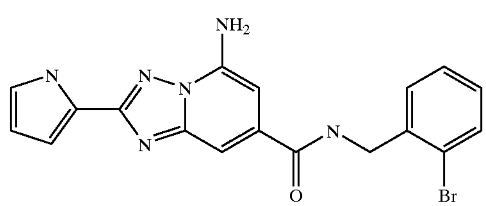 | 411.3 MH+ (100) |
| 93 | 304.2 | 4860.0 | 16.0 | 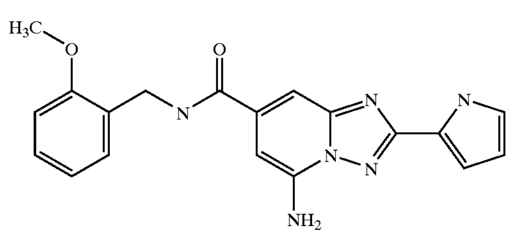 | 362.4 MH+ (100) |

-continued

| No. | Ki HA2A (nM) | Ki HA1 (nM) | selectivity (A1/A2a) | Structure | MW MS m/e (%) |
|---|---|---|---|---|---|
| 94 | 395.4 | | 0.0 | 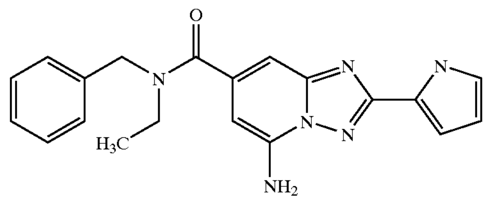 | 360.4 MH+ (100) |
| 95 | 392.2 | | 0.0 | 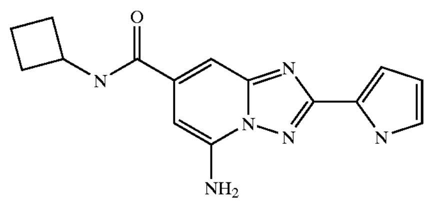 | 296.3 MH+ (100) |
| 96 | 216.7 | 729.0 | 3.4 | 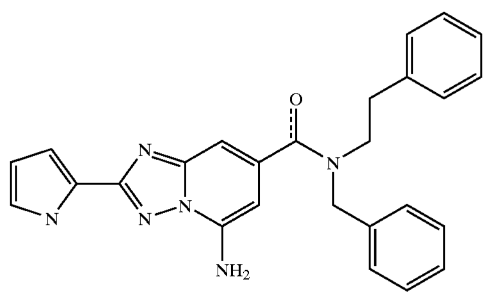 | 436.5 MH+ (100) |
| 97 | 234.8 | 2560.3 | 10.9 | 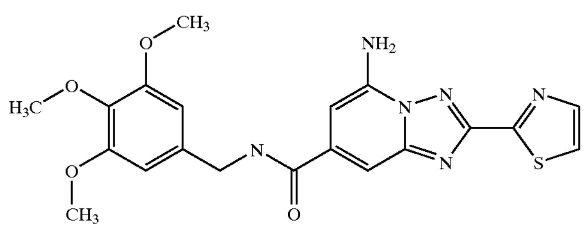 | 440.5 MH+ (100) |
| 98 | 50.5 | 766.6 | 15.2 | 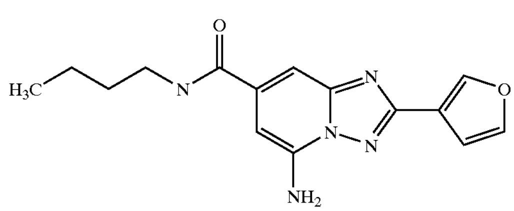 | 299.3 MH+ (100) |
| 99 | 232.8 | 6095.2 | 26.2 | 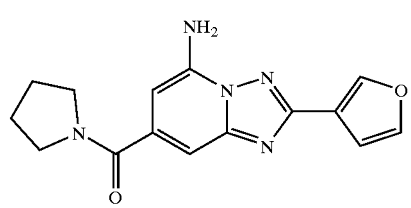 | 297.3 MH+ (100) |

-continued

| No. | Ki HA2A (nM) | Ki HA1 (nM) | selectivity (A1/A2a) | Structure | MW MS m/e (%) |
|---|---|---|---|---|---|
| 100 | 15.5 | 528.8 | 34.1 | 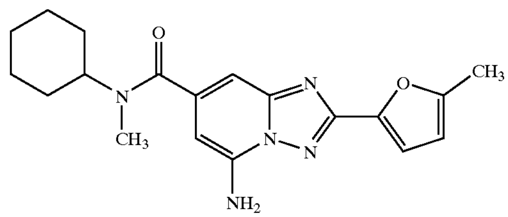 | 353.4 MH+ (100) |
| 101 | 33.3 | 701.4 | 21.1 | 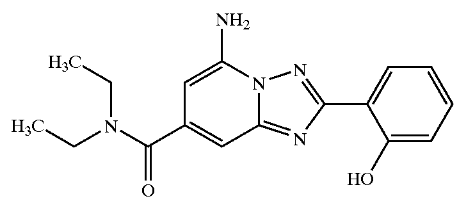 | 325.4 MH+ (100) |
| 102 | 57.6 | 977.6 | 17.0 | 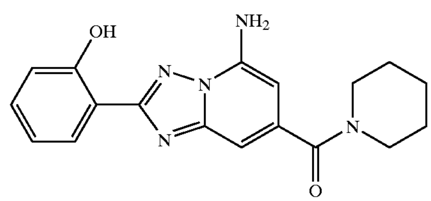 | 337.4 MH+ (100) |
| 103 | 100.5 | 3525.5 | 35.1 | 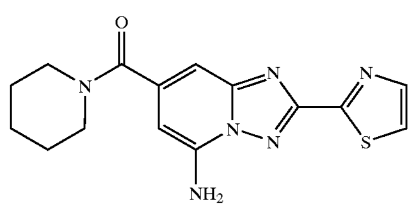 | 328.4 MH+ (100) |
| 104 | 4.9 | 223.4 | 46.0 | 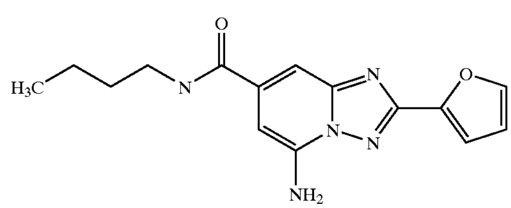 | 299.3 MH+ (100) |
| 105 | 50.9 | 2383.4 | 46.9 | 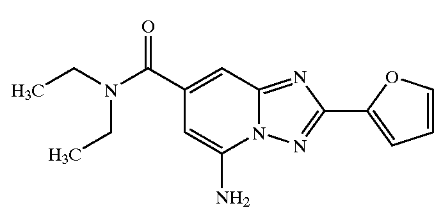 | 299.3 MH+ (100) |
| 106 | 11.4 | 1731.7 | 151.3 | 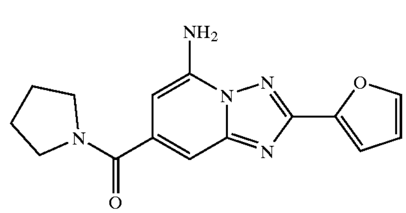 | 297.3 MH+ (100) |

-continued

| No. | Ki HA2A (nM) | Ki HA1 (nM) | selectivity (A1/A2a) | Structure | MW MS m/e (%) |
|---|---|---|---|---|---|
| 107 | 27.0 | 2718.6 | 100.6 | 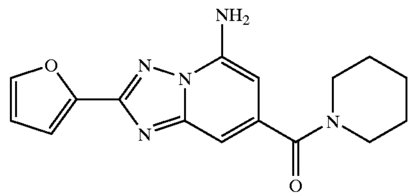 | 311.3 MH+ (100) |
| 108 | 299.2 | 6200.7 | 20.7 | 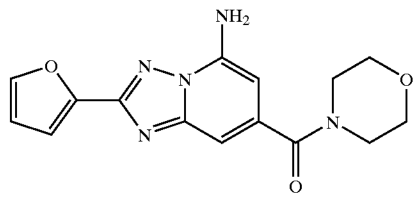 | 313.3 MH+ (100) |
| 109 | 2.9 | 58.7 | 20.2 | 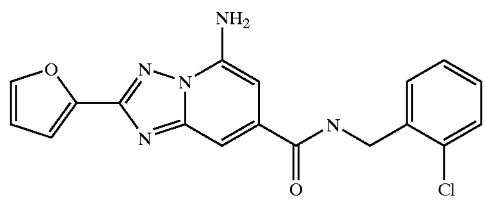 | 367.8 MH+ (100) |
| 110 | 2.6 | 64.2 | 24.5 | 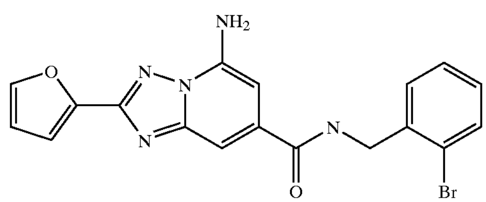 | 412.3 MH+ (100) |
| 111 | 45.2 | 1222.8 | 27.1 | 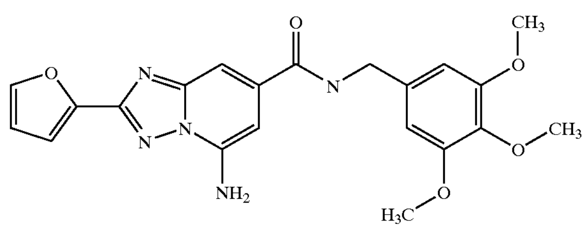 | 423.4 MH+ (100) |
| 112 | 146.7 | 2436.2 | 16.6 | 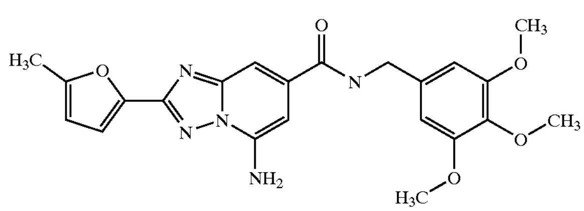 | 437.5 MH+ (100) |
| 113 | 17.2 | 306.6 | 17.8 | 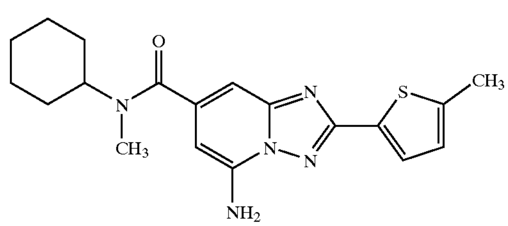 | 369.5 MH+ (100) |

-continued
| No. | Ki HA2A (nM) | Ki HA1 (nM) | selectivity (A1/A2a) | Structure | MW MS m/e (%) |
|---|---|---|---|---|---|
| 114 | 28.3 | 772.1 | 27.3 | 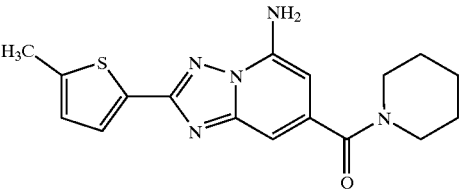 | 341.4 MH+ (100) |
| 115 | 221.8 | 2917.2 | 13.2 | 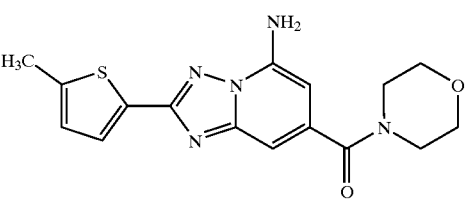 | 343.4 MH+ (100) |
| 116 | 15.3 | 169.8 | 11.1 | 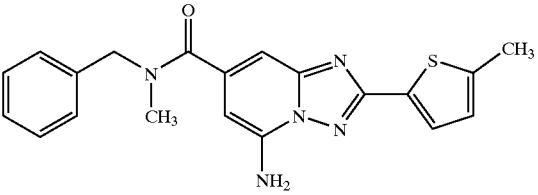 | 377.5 MH+ (100) |
| 117 | 9.2 | 177.5 | 19.2 | 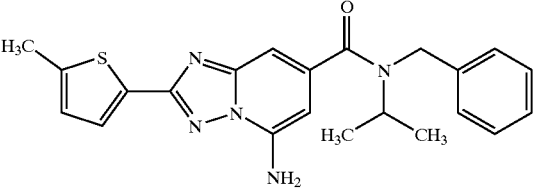 | 405.5 MH+ (100) |
| 118 | 126.5 | 1964.5 | 15.5 | 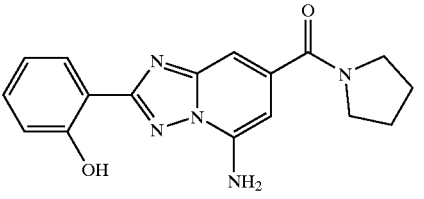 | 323.4 MH+ (100) |
| 119 | 17.1 | 428.6 | 25.0 | 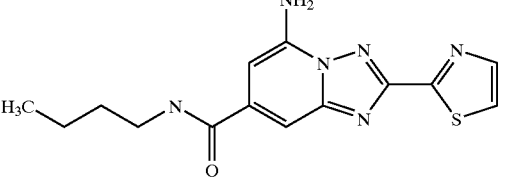 | 316.4 MH+ (100) |
| 120 | 77.4 | 2740.3 | 35.4 | 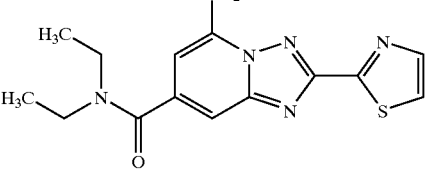 | 316.4 MH+ (100) |

-continued
| No. | Ki HA2A (nM) | Ki HA1 (nM) | selectivity (A1/A2a) | Structure | MW MS m/e (%) |
|---|---|---|---|---|---|
| 121 | 17.0 | 204.5 | 12.0 | 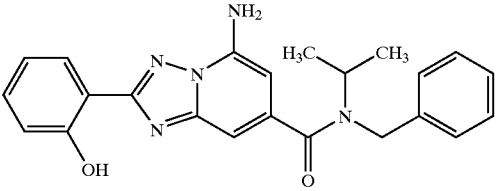 | 401.5 MH$^+$ (100) |
| 122 | 317.4 | 3317.6 | 10.5 | 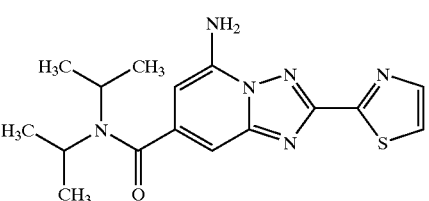 | 344.4 MH$^+$ (100) |
| 123 | 43.5 | 698.3 | 16.0 | 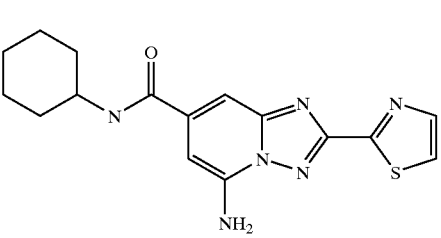 | 342.4 MH$^+$ (100) |
| 124 | 99.2 | 1508.3 | 15.2 | 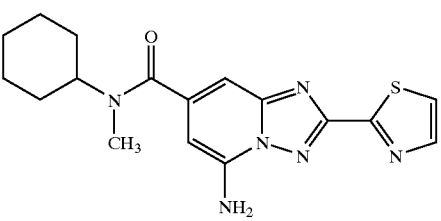 | 356.5 MH$^+$ (100) |
| 125 | 24.4 | 254.8 | 10.5 | 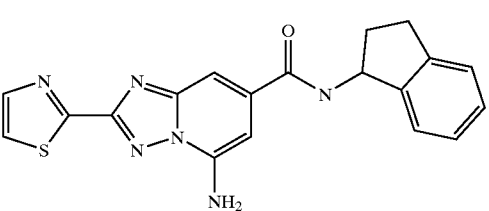 | 376.4 MH$^+$ (100) |
| 126 | 54.4 | 231.8 | 4.3 | 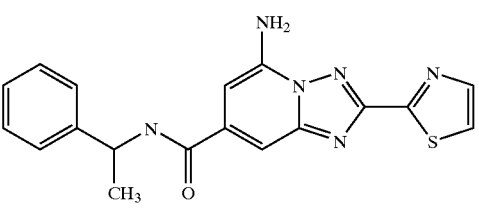 | 364.4 MH$^+$ (100) |
| 127 | 104.1 | 1967.6 | 18.9 | 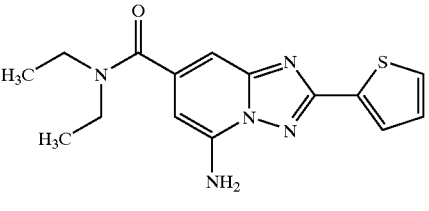 | 315.4 MH$^+$ (100) |

-continued

| No. | Ki HA2A (nM) | Ki HA1 (nM) | selectivity (A1/A2a) | Structure | MW MS m/e (%) |
|---|---|---|---|---|---|
| 128 | 104.1 | 1480.3 | 14.2 | 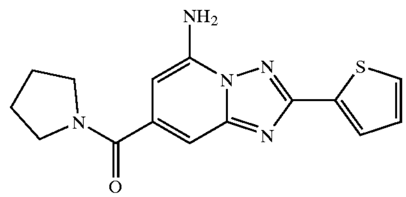 | 313.4 MH+ (100) |
| 129 | 100.5 | 1455.5 | 14.5 | 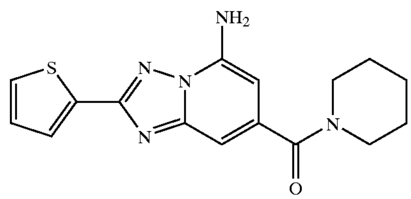 | 327.4 MH+ (100) |
| 130 | 15.2 | 127.6 | 8.4 | 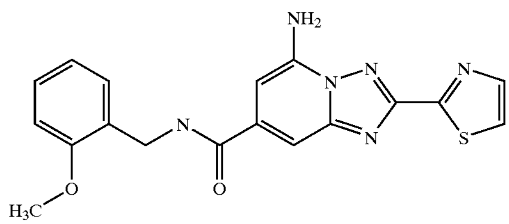 | 380.4 MH+ (100) |
| 131 | 19.4 | 345.4 | 17.8 | 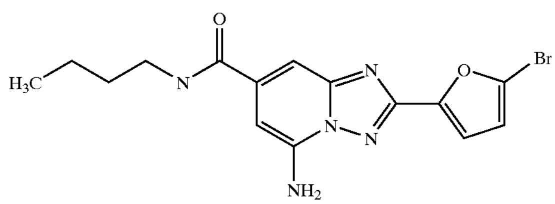 | 378.2 MH+ (100) |
| 132 | 33.8 | 766.6 | 22.7 | 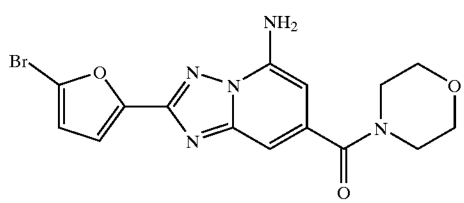 | 392.2 MH+ (100) |
| 133 | 146.0 | 1942.8 | 13.3 | 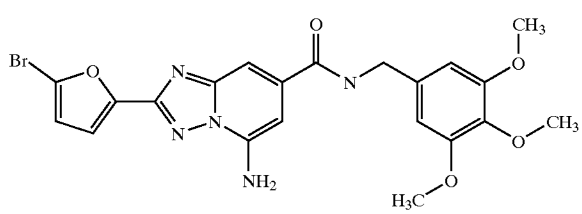 | 502.3 MH+ (100) |
| 134 | 287.2 | 2675.2 | 9.3 | 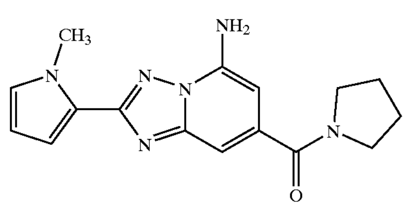 | 310.4 MH+ (100) |

-continued

| No. | Ki HA2A (nM) | Ki HA1 (nM) | selectivity (A1/A2a) | Structure | MW MS m/e (%) |
|---|---|---|---|---|---|
| 135 | 166.5 | 1821.7 | 10.9 | 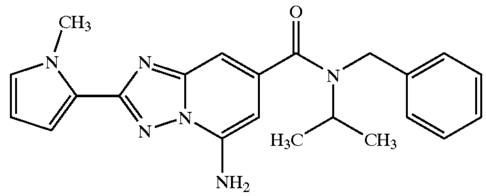 | 388.5 MH+ (100) |
| 136 | 12.0 | 222.5 | 18.5 | 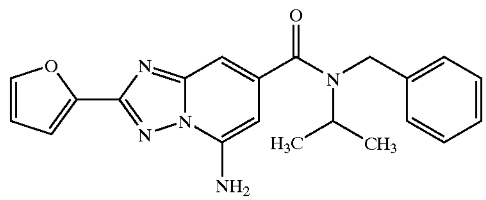 | 375.4 MH+ (100) |
| 137 | 11.0 | 217.6 | 19.8 | 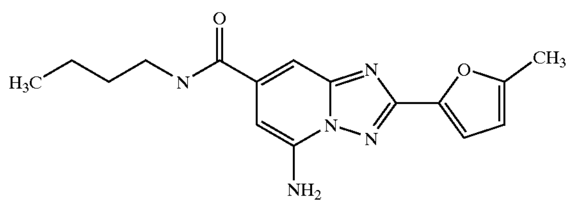 | 313.4 MH+ (100) |
| 138 | 123.3 | 1266.2 | 10.3 | 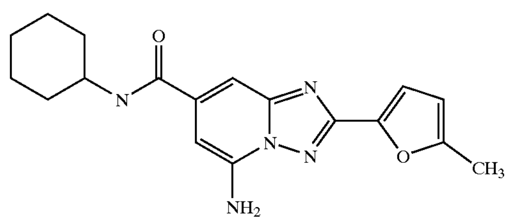 | 339.4 MH+ (100) |
| 139 | 74.5 | 1753.4 | 23.5 | 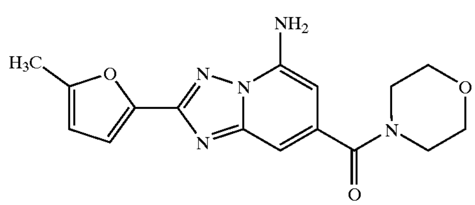 | 327.3 MH+ (100) |
| 140 | 7.3 | 107.4 | 14.7 | 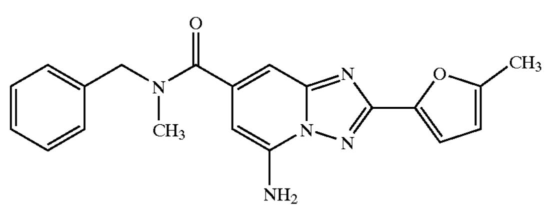 | 361.4 MH+ (100) |
| 141 | 5.9 | 122.6 | 20.8 | 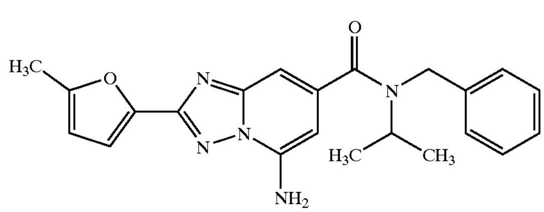 | 389.5 MH+ (100) |

-continued

| No. | Ki HA2A (nM) | Ki HA1 (nM) | selectivity (A1/A2a) | Structure | MW | MS m/e (%) |
|---|---|---|---|---|---|---|
| 142 | 281.3 | 4118.3 | 14.6 | 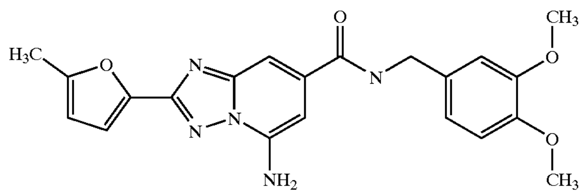 | 407.4 | MH+ (100) |
| 143 | 120.7 | 1089.3 | 9.0 | 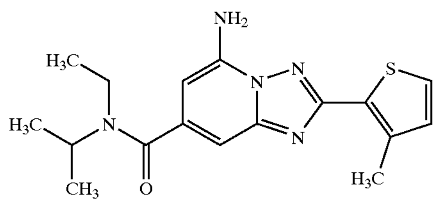 | 343.5 | MH+ (100) |
| 144 | 63.4 | 819.3 | 12.9 | 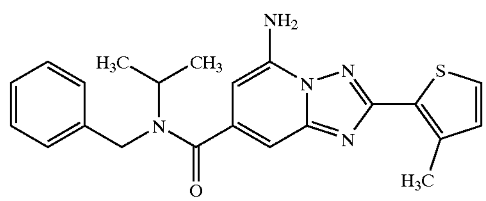 | 405.5 | MH+ (100) |
| 145 | 26.0 | 106.4 | 4.1 | 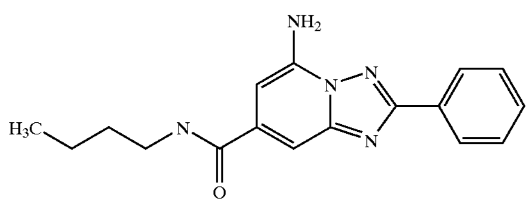 | 309.4 | MH+ (100) |
| 146 | 130.4 | 1958.3 | 15.0 | 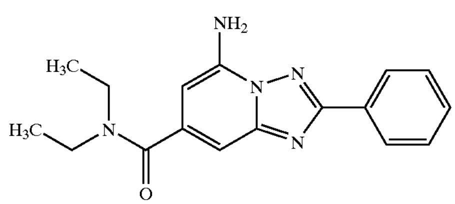 | 309.4 | MH+ (100) |
| 147 | 139.8 | 453.4 | 3.2 | 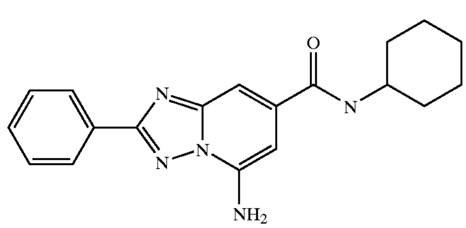 | 335.4 | MH+ (100) |
| 148 | 148.3 | 1197.9 | 8.1 | 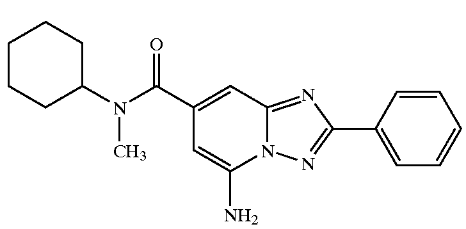 | 349.4 | MH+ (100) |

-continued

| No. | Ki HA2A (nM) | Ki HA1 (nM) | selectivity (A1/A2a) | Structure | MW | MS m/e (%) |
|---|---|---|---|---|---|---|
| 149 | 57.4 | 98.1 | 1.7 | 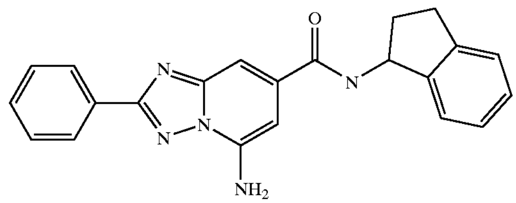 | 369.4 | MH+ (100) |
| 150 | 82.3 | 710.7 | 8.6 | 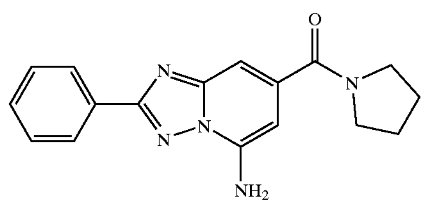 | 307.4 | MH+ (100) |
| 151 | 85.5 | 927.9 | 10.8 | 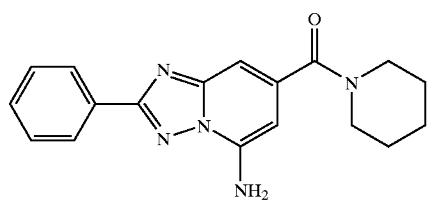 | 321.4 | MH+ (100) |
| 152 | 32.8 | 366.5 | 11.2 | 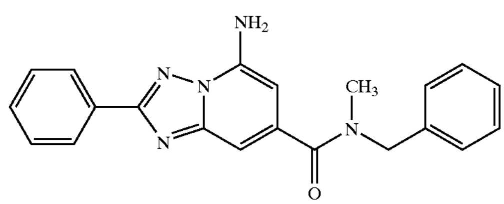 | 357.4 | MH+ (100) |
| 153 | 301.1 | 4804.1 | 16.0 | 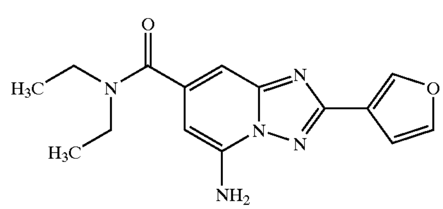 | 299.3 | MH+ (100) |
| 154 | 88.1 | 1176.2 | 13.3 | 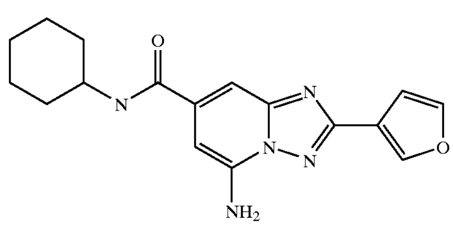 | 325.4 | MH+ (100) |
| 155 | 301.5 | 5853.1 | 19.4 | 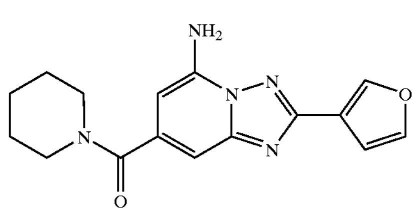 | 311.3 | MH+ (100) |

-continued

| No. | Ki HA2A (nM) | Ki HA1 (nM) | selectivity (A1/A2a) | Structure | MW MS m/e (%) |
|---|---|---|---|---|---|
| 156 | 17.1 | 228.4 | 13.3 | 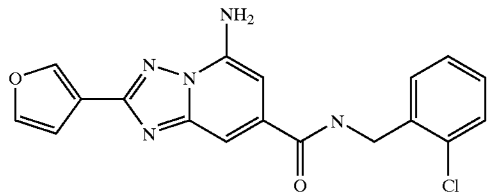 | 367.8 MH+ (100) |
| 157 | 18.0 | 231.2 | 12.8 | 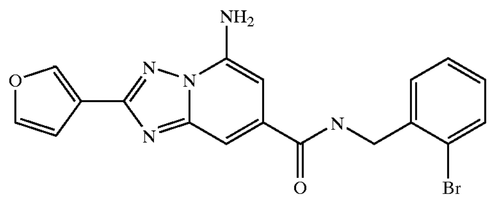 | 412.3 MH+ (100) |
| 158 | 87.5 | 258.5 | 3.0 | 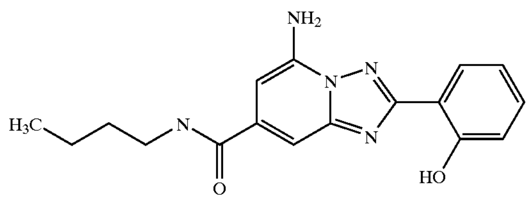 | 325.4 MH+ (100) |
| 159 | 104.7 | 279.3 | 2.7 | 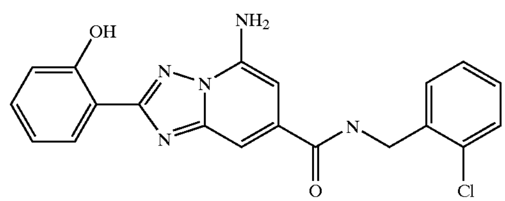 | 393.8 MH+ (100) |
| 160 | 125.5 | 138.7 | 1.1 | 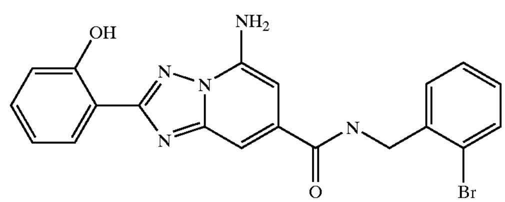 | 438.3 MH+ (100) |
| 161 | 28.0 | 160.8 | 5.7 | 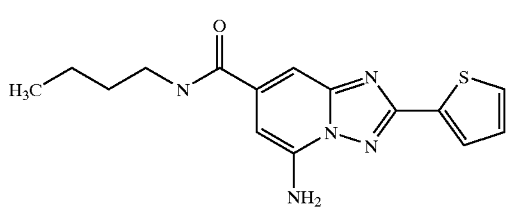 | 315.4 MH+ (100) |
| 162 | 61.4 | 300.7 | 4.9 | 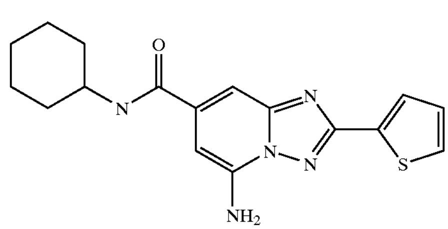 | 341.4 MH+ (100) |

-continued

| No. | Ki HA2A (nM) | Ki HA1 (nM) | selectivity (A1/A2a) | Structure | MW MS m/e (%) |
|---|---|---|---|---|---|
| 163 | 31.1 | 124.8 | 4.0 | 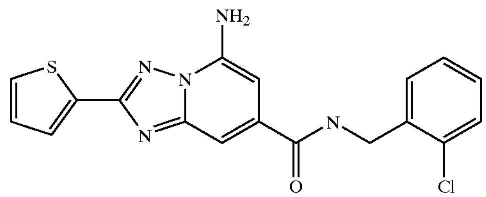 | 383.9 MH+ (100) |
| 164 | 25.5 | 111.1 | 4.4 | 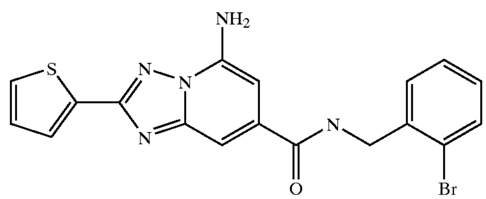 | 428.3 MH+ (100) |
| 165 | 88.8 | 769.7 | 8.7 | 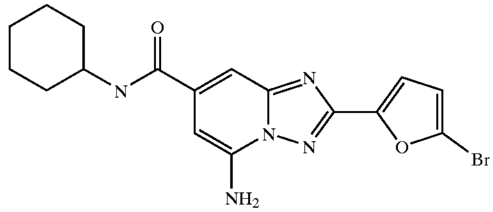 | 404.3 MH+ (100) |
| 166 | 39.7 | 201.4 | 5.1 | 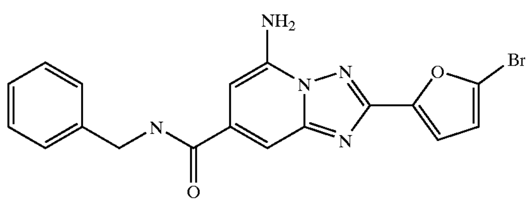 | 412.3 MH+ (100) |
| 167 | 42.7 | 196.4 | 4.6 | 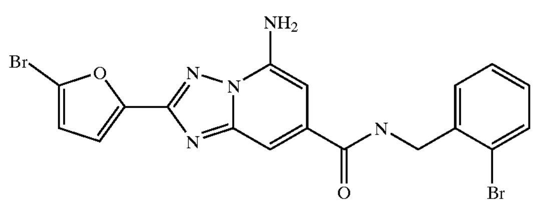 | 491.2 MH+ (100) |
| 168 | 18.4 | 47.2 | 2.6 | 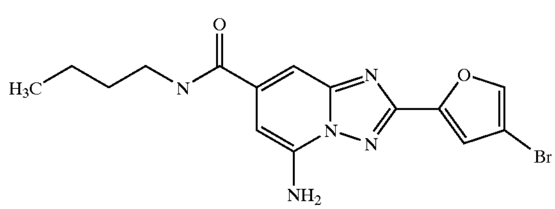 | 378.2 MH+ (100) |
| 169 | 119.3 | 406.9 | 3.4 | 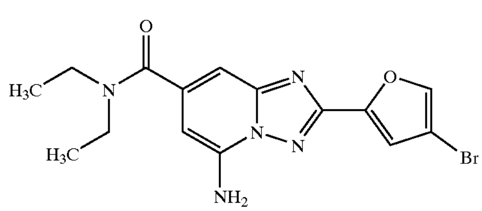 | 378.2 MH+ (100) |

-continued

| No. | Ki HA2A (nM) | Ki HA1 (nM) | selectivity (A1/A2a) | Structure | MW MS m/e (%) |
|---|---|---|---|---|---|
| 170 | 33.8 | 152.4 | 4.5 | 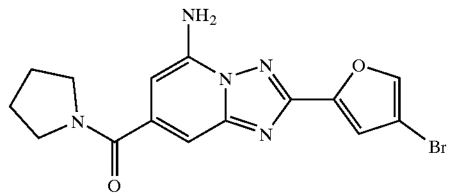 | 376.2 MH+ (100) |
| 171 | 64.9 | 276.2 | 4.3 | 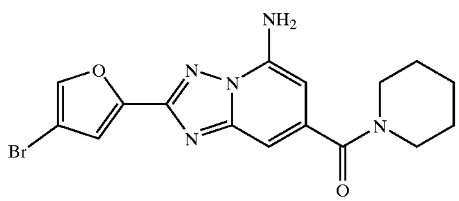 | 390.2 MH+ (100) |
| 172 | 29.7 | 24.7 | 0.8 | 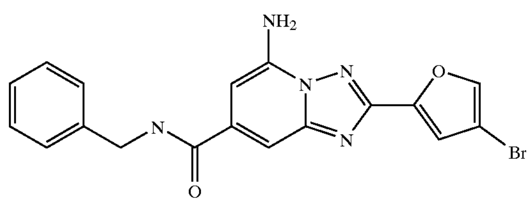 | 412.3 MH+ (100) |
| 173 | 44.4 | 73.6 | 1.7 | 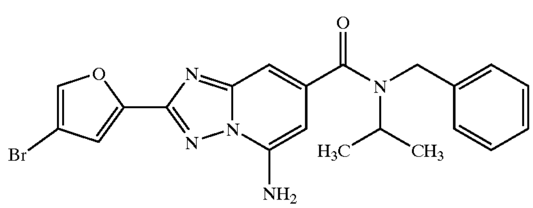 | 454.3 MH+ (100) |
| 174 | 11.1 | 17.5 | 1.6 | 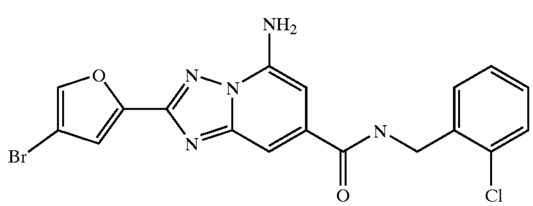 | 446.7 MH+ (100) |
| 175 | 14.6 | 22.6 | 1.5 | 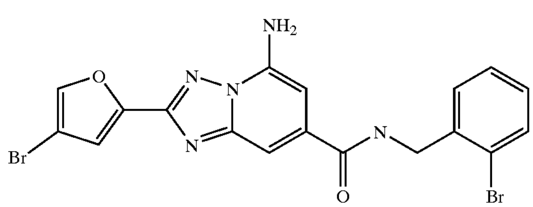 | 491.2 MH+ (100) |
| 176 | 329.4 | 150.8 | 0.5 | 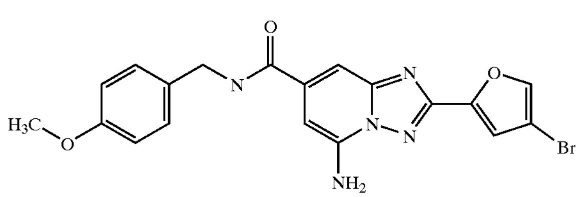 | 442.3 MH+ (100) |

-continued

| No. | Ki HA2A (nM) | Ki HA1 (nM) | selectivity (A1/A2a) | Structure | MW MS m/e (%) |
|---|---|---|---|---|---|
| 177 | 197.4 | 266.3 | 1.3 | 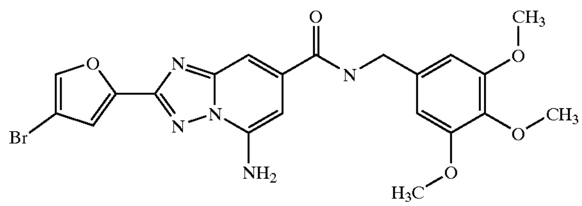 | 502.3 MH+ (100) |
| 178 | 65.2 | 450.0 | 6.9 | 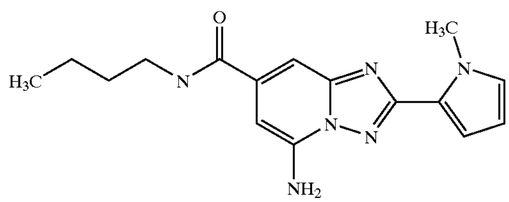 | 312.4 MH+ (100) |
| 179 | 143.7 | 779.0 | 5.4 | 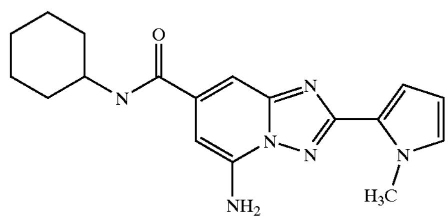 | 338.4 MH+ (100) |
| 180 | 111.9 | 306.6 | 2.7 | 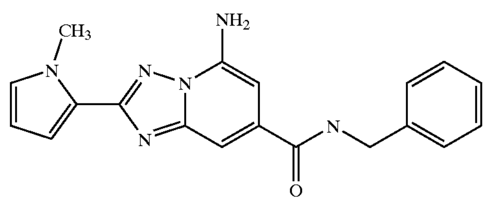 | 346.4 MH+ (100) |
| 181 | 54.3 | 256.3 | 4.7 | 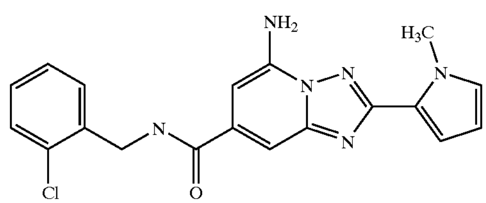 | 380.8 MH+ (100) |
| 182 | 54.6 | 269.7 | 4.9 | 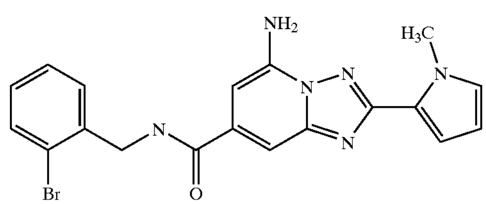 | 425.3 MH+ (100) |
| 183 | 33.7 | 302.0 | 9.0 | 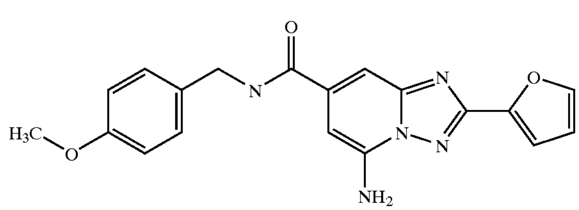 | 363.4 MH+ (100) |

-continued

| No. | Ki HA2A (nM) | Ki HA1 (nM) | selectivity (A1/A2a) | Structure | MW | MS m/e (%) |
|---|---|---|---|---|---|---|
| 184 | 69.5 | 133.4 | 1.9 | 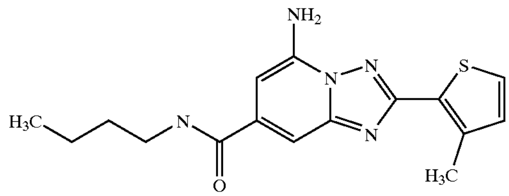 | 329.4 | MH+ (100) |
| 185 | 237.7 | 1415.2 | 6.0 | 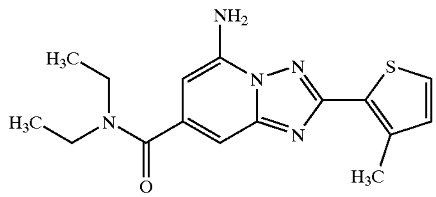 | 329.4 | MH+ (100) |
| 186 | 209.8 | 249.2 | 1.2 | 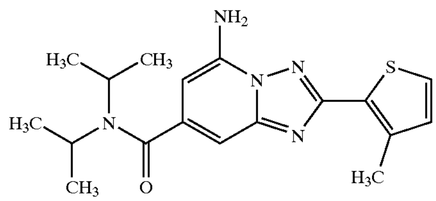 | 357.5 | MH+ (100) |
| 187 | 223.7 | 228.4 | 1.0 | 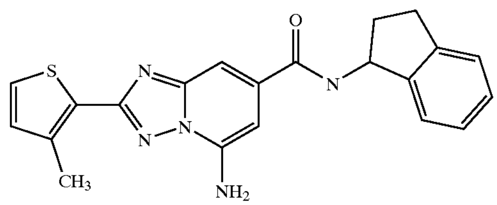 | 389.5 | MH+ (100) |
| 188 | 225.7 | 710.7 | 3.1 | 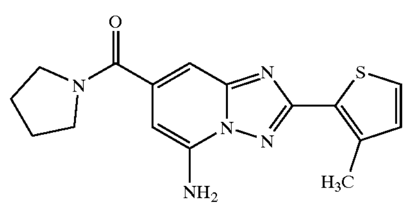 | 327.4 | MH+ (100) |
| 189 | 267.6 | 763.4 | 2.9 | 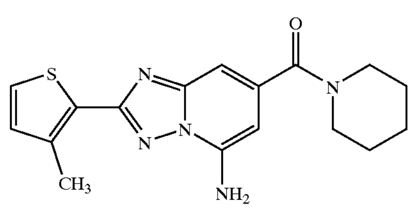 | 341.4 | MH+ (100) |
| 190 | 365.5 | 47.3 | 0.1 | 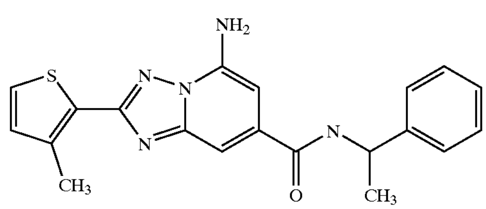 | 377.5 | MH+ (100) |

| No. | Ki HA2A (nM) | Ki HA1 (nM) | selectivity (A1/A2a) | Structure | MW | MS m/e (%) |
|---|---|---|---|---|---|---|
| 191 | 108.0 | 131.3 | 1.2 | 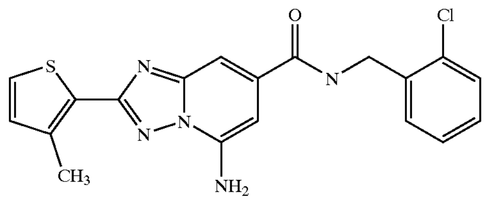 | 397.9 | MH+ (100) |
| 192 | 129.4 | 112.3 | 0.9 | 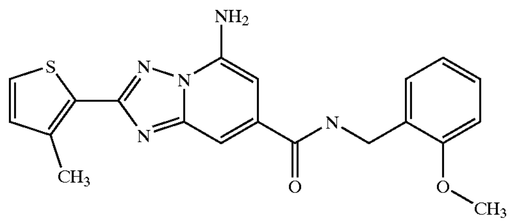 | 393.5 | MH+ (100) |
| 193 | 41.7 | 74.8 | 1.8 | 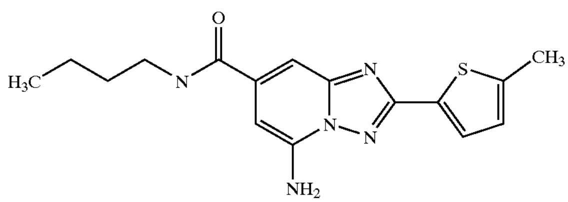 | 329.4 | MH+ (100) |
| 194 | 56.3 | 245.8 | 4.4 | 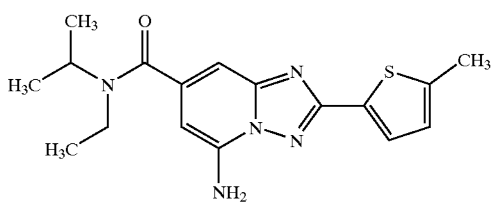 | 343.5 | MH+ (100) |
| 195 | 108.9 | 145.2 | 1.3 | 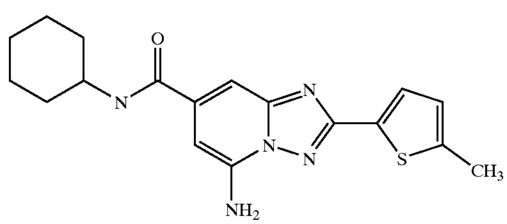 | 355.5 | MH+ (100) |
| 196 | 52.2 | 432.0 | 8.3 | 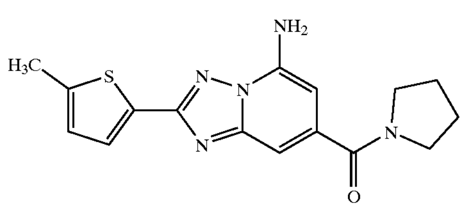 | 327.4 | MH+ (100) |
| 197 | 177.6 | 90.3 | 0.5 | 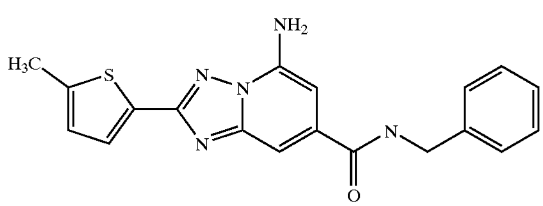 | 363.4 | MH+ (100) |

-continued

| No. | Ki HA2A (nM) | Ki HA1 (nM) | selectivity (A1/A2a) | Structure | MW | MS m/e (%) |
|---|---|---|---|---|---|---|
| 198 | 174.0 | 112.3 | 0.6 | 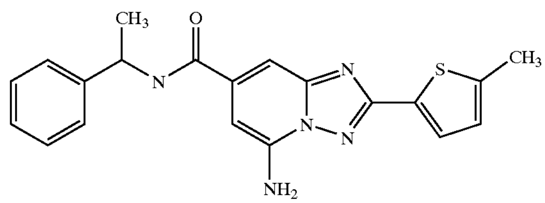 | 377.5 | MH+ (100) |
| 199 | 30.2 | 36.9 | 1.2 | 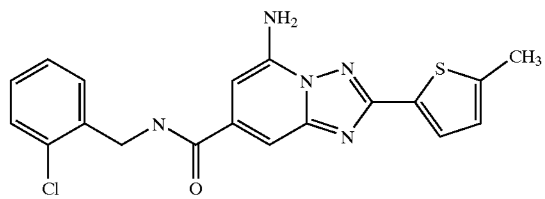 | 397.9 | MH+ (100) |
| 200 | 22.0 | 37.9 | 1.7 | 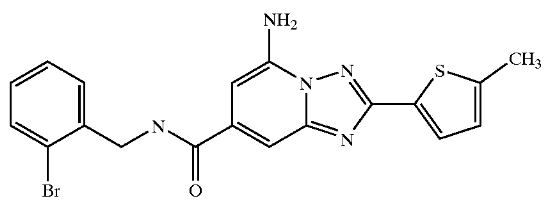 | 442.3 | MH+ (100) |
| 201 | 31.3 | 33.0 | 1.1 | 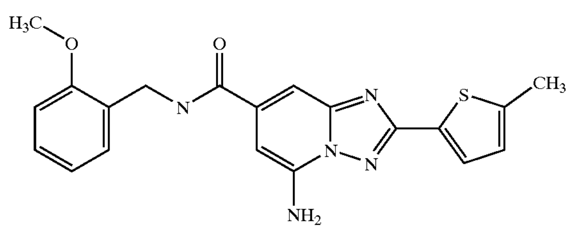 | 393.5 | MH+ (100) |
| 202 | 309.9 | 678.1 | 2.2 | 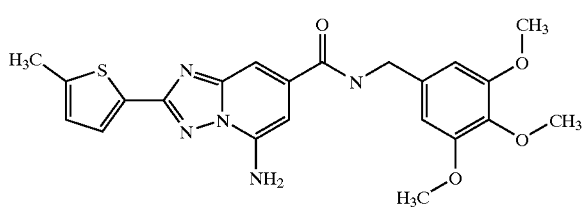 | 453.5 | MH+ (100) |
| 203 | 60.0 | 66.2 | 1.1 | 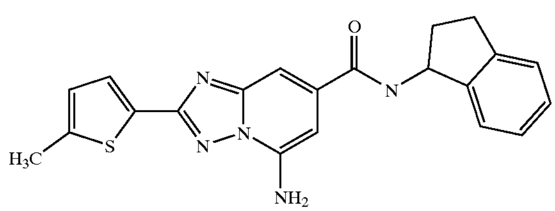 | 389.5 | MH+ (100) |
| 204 | 41.7 | 325.2 | 7.8 | 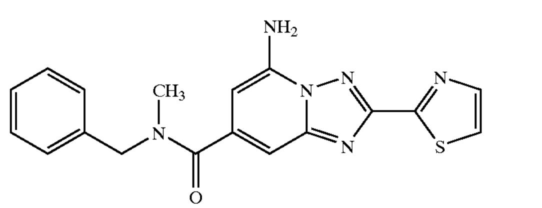 | 364.4 | MH+ (100) |

-continued

| No. | Ki HA2A (nM) | Ki HA1 (nM) | selectivity (A1/A2a) | Structure | MW MS m/e (%) |
|---|---|---|---|---|---|
| 205 | 157.4 | 293.9 | 1.9 | 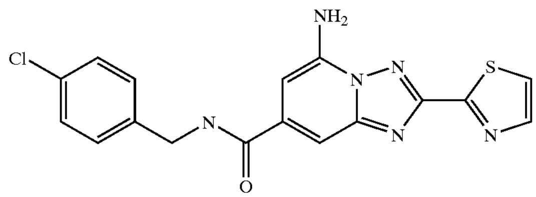 | 384.9 MH+ (100) |
| 206 | 125.5 | 657.3 | 5.2 | 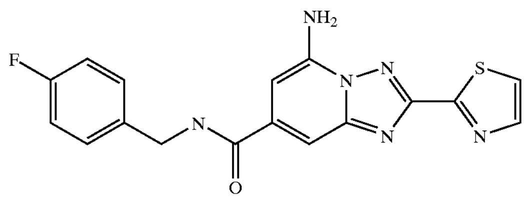 | 368.4 MH+ (100) |
| 207 | 187.3 | 533.2 | 2.8 | 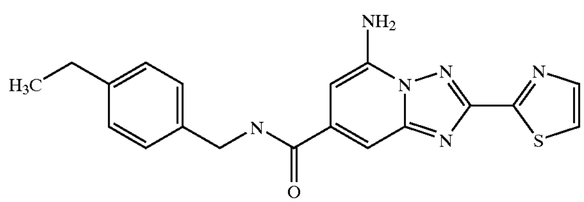 | 380.4 MH+ (100) |
| 208 | 316.1 | 1862.1 | 5.9 | 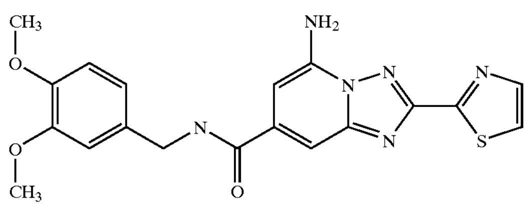 | 410.5 MH+ (100) |
| 209 | 39.2 | 320.3 | 8.2 | 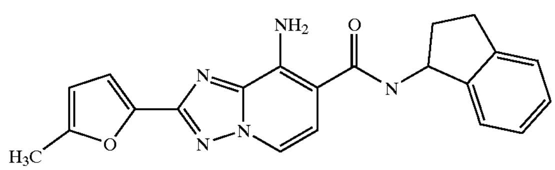 | 373.4 MH+ (100) |
| 210 | 48.6 | 298.9 | 6.1 | 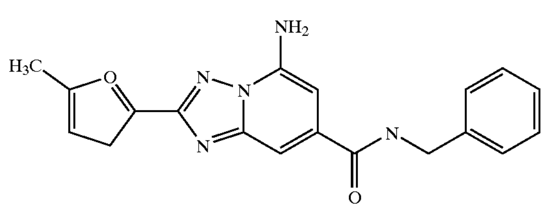 | 347.4 MH+ (100) |
| 211 | 57.3 | 298.2 | 5.2 | 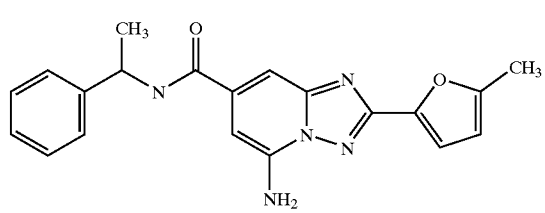 | 361.4 MH+ (100) |

| No. | Ki HA2A (nM) | Ki HA1 (nM) | selectivity (A1/A2a) | Structure | MW MS m/e (%) |
|---|---|---|---|---|---|
| 212 | 190.2 | 634.0 | 3.3 | 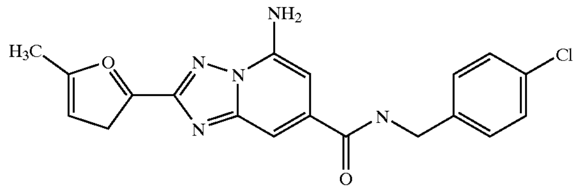 | 381.8 MH+ (100) |
| 213 | 73.2 | 343.2 | 4.7 | 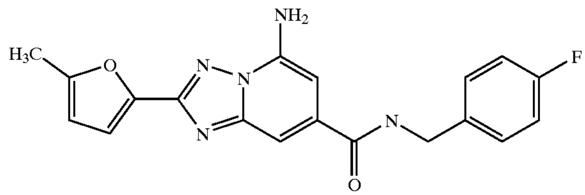 | 365.4 MH+ (100) |
| 214 | 14.6 | 111.1 | 7.6 | 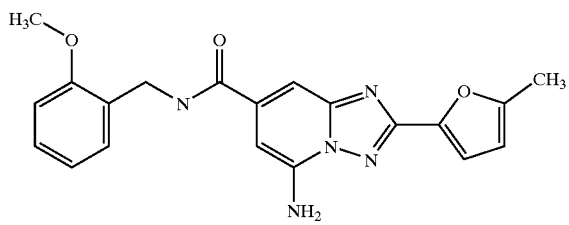 | 377.4 MH+ (100) |
| 215 | 294.6 | 1539.3 | 5.2 | 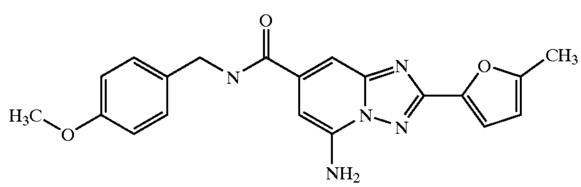 | 377.4 MH+ (100) |
| 216 | 64.1 | 148.7 | 2.3 | 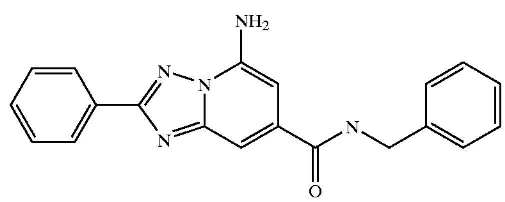 | 343.4 MH+ (100) |
| 217 | 84.6 | 72.6 | 0.9 | 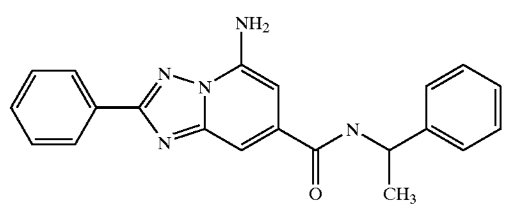 | 357.4 MH+ (100) |
| 218 | 47.2 | 116.4 | 2.5 | 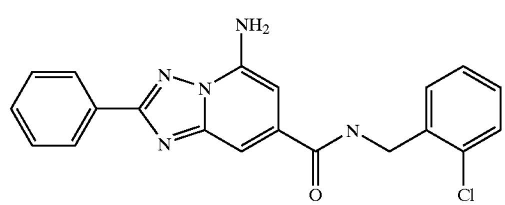 | 377.8 MH+ (100) |

-continued

| No. | Ki HA2A (nM) | Ki HA1 (nM) | selectivity (A1/A2a) | Structure | MW MS m/e (%) |
|---|---|---|---|---|---|
| 219 | 30.0 | 133.4 | 4.4 | 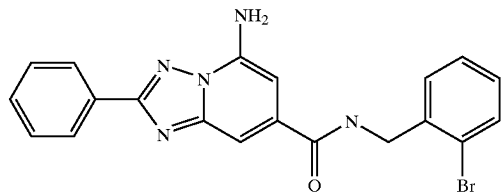 | 422.3 MH+ (100) |
| 220 | 29.2 | 48.3 | 1.7 | 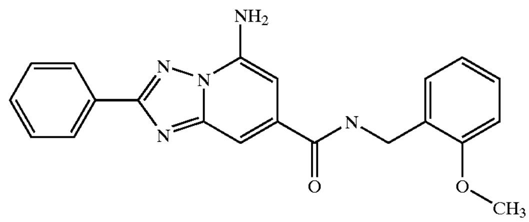 | 373.4 MH+ (100) |
| 221 | 308.0 | 2259.3 | 7.3 | 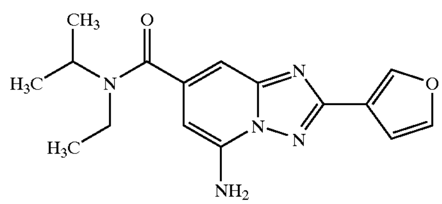 | 313.4 MH+ (100) |
| 222 | 240.7 | 2048.3 | 8.5 | 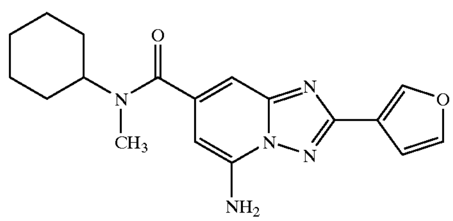 | 339.4 MH+ (100) |
| 223 | 44.1 | 414.0 | 9.4 | 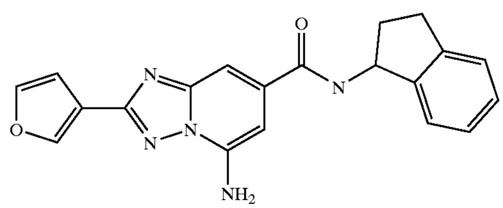 | 359.4 MH+ (100) |
| 224 | 47.4 | 215.7 | 4.5 | 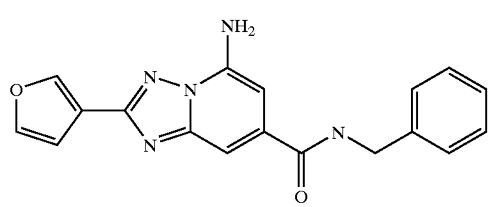 | 333.4 MH+ (100) |
| 225 | 103.4 | 124.8 | 1.2 | 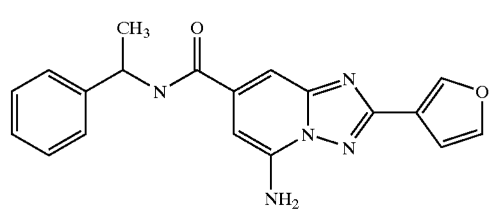 | 347.4 MH+ (100) |

-continued

| No. | Ki HA2A (nM) | Ki HA1 (nM) | selectivity (A1/A2a) | Structure | MW MS m/e (%) |
|---|---|---|---|---|---|
| 226 | 120.7 | 1011.7 | 8.4 | 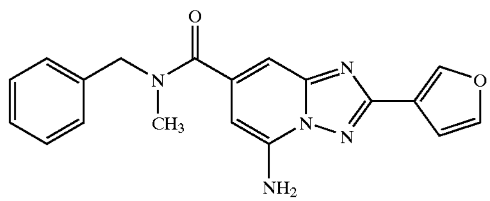 | 347.4 MH+ (100) |
| 227 | 192.5 | 735.5 | 3.8 | 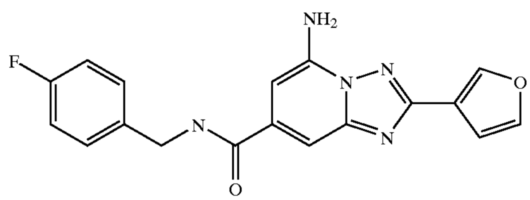 | 351.3 MH+ (100) |
| 228 | 30.5 | 163.9 | 5.4 | 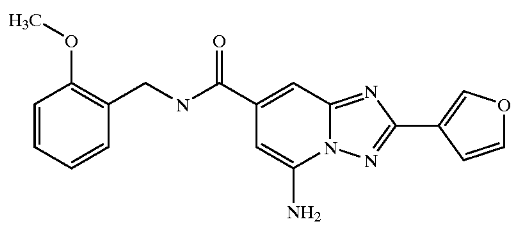 | 363.4 MH+ (100) |
| 229 | 384.1 | | 0.0 | 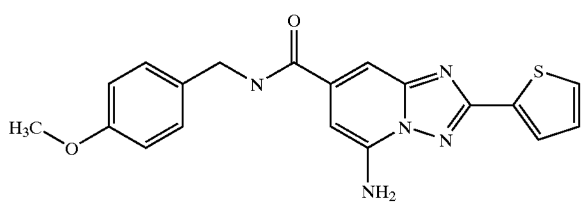 | 379.4 MH+ (100) |
| 230 | 328.8 | | 0.0 | 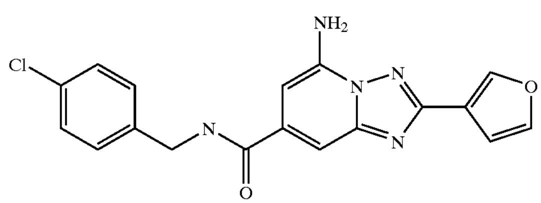 | 367.8 MH+ (100) |
| 231 | 364.6 | | 0.0 | 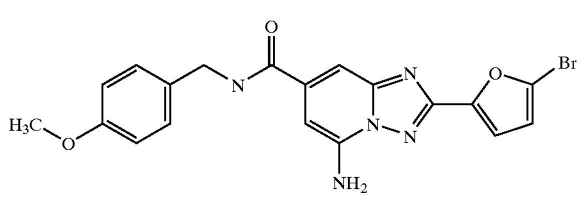 | 442.3 MH+ (100) |
| 232 | 374.6 | | 0.0 | 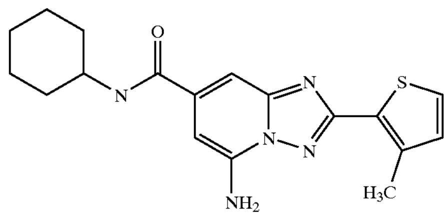 | 355.5 MH+ (100) |

-continued
| No. | Ki HA2A (nM) | Ki HA1 (nM) | selectivity (A1/A2a) | Structure | MW MS m/e (%) |
|---|---|---|---|---|---|
| 233 | 7.2 | 280.2 | 38.7 | 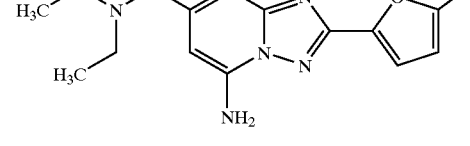 | 333.8 MH+ (100) |
| 234 | 69.5 | 455.3 | 6.6 | 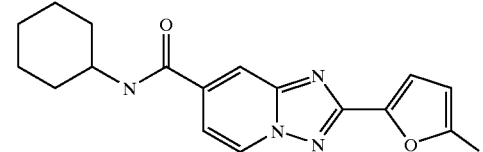 | 359.8 MH+ (100) |
| 235 | 18.1 | 769.7 | 42.5 | 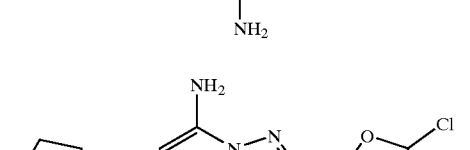 | 331.8 MH+ (100) |
| 236 | 9.2 | 324.6 | 35.2 | 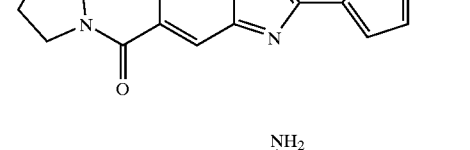 | 345.8 MH+ (100) |
| 237 | 52.3 | 707.6 | 13.5 | 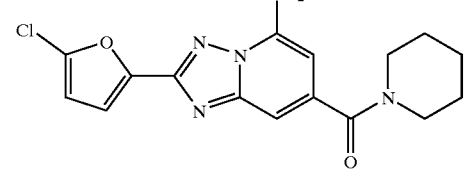 | 347.8 MH+ (100) |
| 238 | 40.4 | 94.3 | 2.3 | 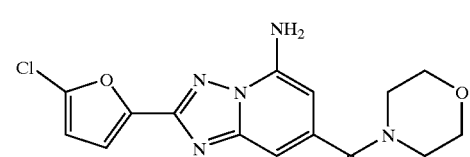 | 367.8 MH+ (100) |
| 239 | 1.7 | 25.1 | 14.6 | 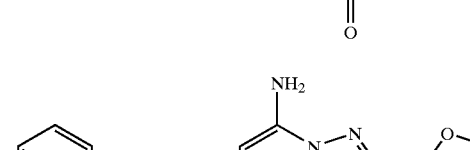 | 409.9 MH+ (100) |

-continued

| No. | Ki HA2A (nM) | Ki HA1 (nM) | selectivity (A1/A2a) | Structure | MW MS m/e (%) |
|---|---|---|---|---|---|
| 240 | 35.8 | 91.2 | 2.5 | 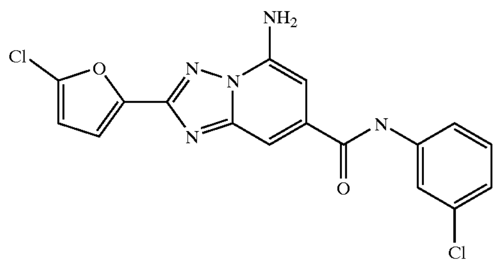 | 402.2 MH+ (100) |
| 241 | 26.5 | 70.6 | 2.7 | 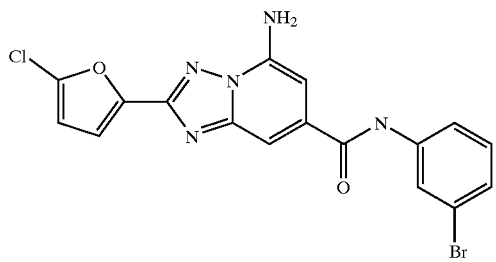 | 446.7 MH+ (100) |
| 242 | 6.5 | 124.4 | 19.0 | 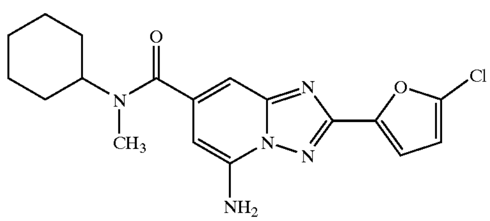 | 373.8 MH+ (100) |
| 243 | 3.3 | 95.6 | 28.6 | 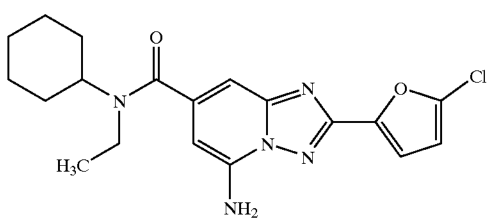 | 387.9 MH+ (100) |
| 244 | 217.7 | 190.2 | 0.9 | 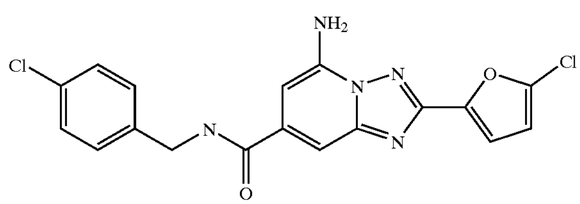 | 402.2 MH+ (100) |
| 245 | 155.4 | 288.9 | 1.9 | 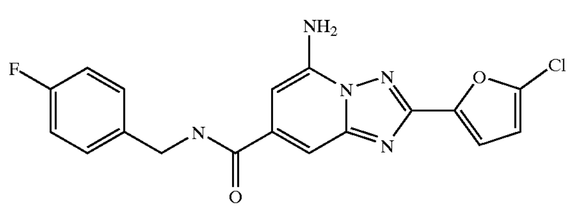 | 385.8 MH+ (100) |

-continued
| No. | Ki HA2A (nM) | Ki HA1 (nM) | selectivity (A1/A2a) | Structure | MW MS m/e (%) |
|---|---|---|---|---|---|
| 246 | 24.0 | 71.7 | 3.0 | 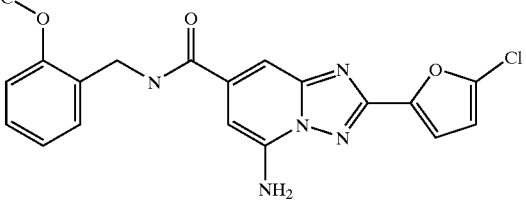 | 397.8 MH+ (100) |
| 247 | 9.2 | 161.4 | 17.6 | 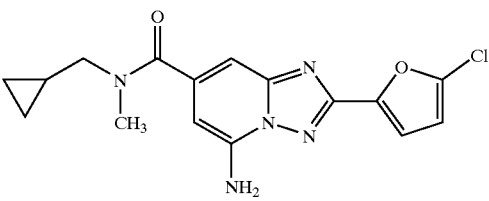 | 345.8 MH+ (100) |
| 248 | 44.3 | 601.4 | 13.6 | 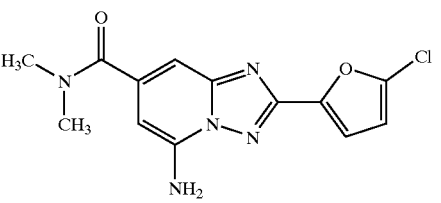 | 305.7 MH+ (100) |
| 249 | 2089.1 | 6206.9 | 3.0 | 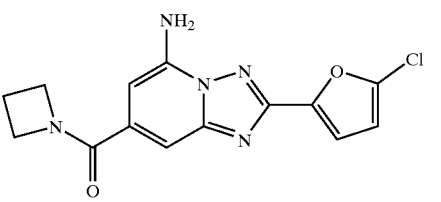 | 317.7 MH+ (100) |
| 250 | 19.1 | 458.7 | 24.0 | 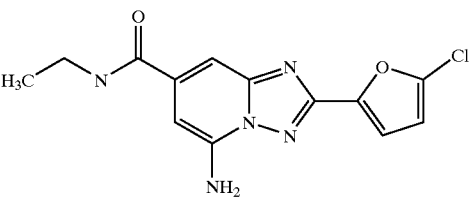 | 319.8 MH+ (100) |
| 251 | 14.7 | 360.0 | 24.5 | 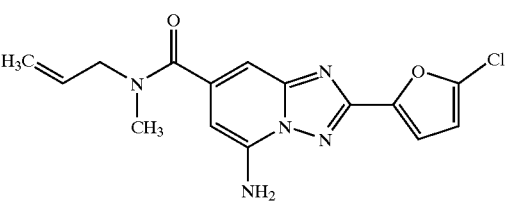 | 331.8 MH+ (100) |
| 252 | 15.5 | 437.9 | 28.3 | 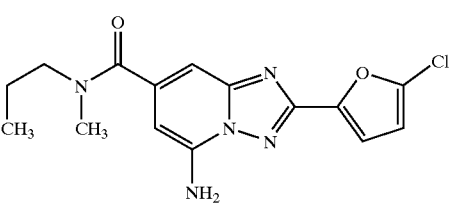 | 333.8 MH+ (100) |

-continued
| No. | Ki HA2A (nM) | Ki HA1 (nM) | selectivity (A1/A2a) | Structure | MW MS m/e (%) |
|---|---|---|---|---|---|
| 253 | 9.5 | 275.6 | 28.9 | 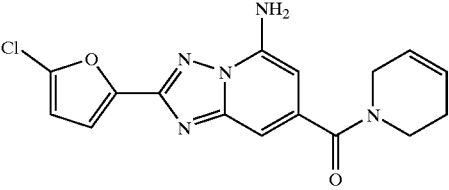 | 343.8 MH+ (100) |
| 254 | 11.2 | 502.8 | 44.8 | 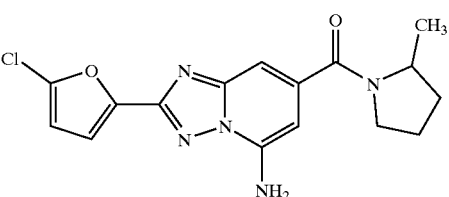 | 345.8 MH+ (100) |
| 255 | 3.2 | 92.5 | 28.9 | 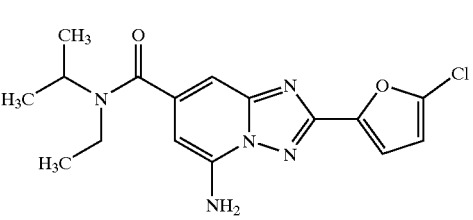 | 347.8 MH+ (100) |
| 256 | 24.4 | 430.1 | 17.7 | 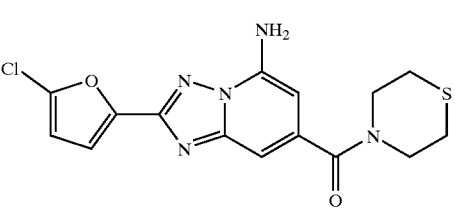 | 363.8 MH+ (100) |
| 257 | 28.9 | 819.3 | 28.3 | 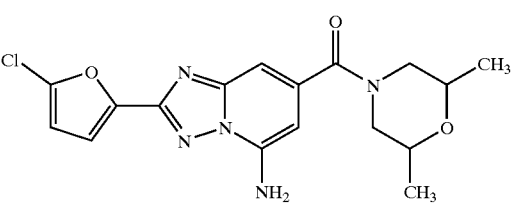 | 375.8 MH+ (100) |
| 258 | 7.2 | 220.7 | 30.6 | 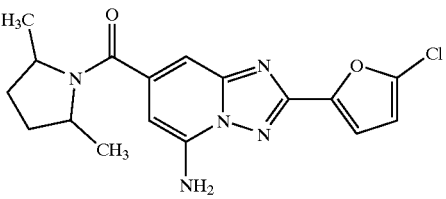 | 359.8 MH+ (100) |
| 259 | 119.2 | 540.3 | 4.5 | 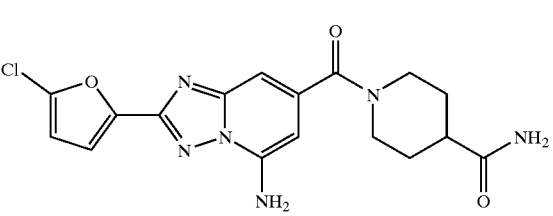 | 388.8 MH+ (100) |

-continued

| No. | Ki HA2A (nM) | Ki HA1 (nM) | selectivity (A1/A2a) | Structure | MW MS m/e (%) |
|---|---|---|---|---|---|
| 260 | 13.4 | 269.7 | 20.2 | 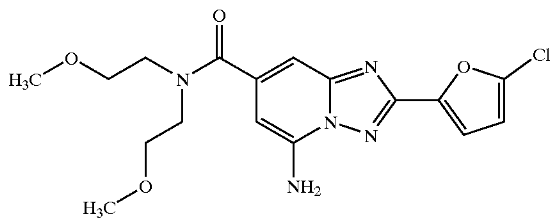 | 393.8 MH+ (100) |
| 261 | 2.6 | 37.7 | 14.7 | 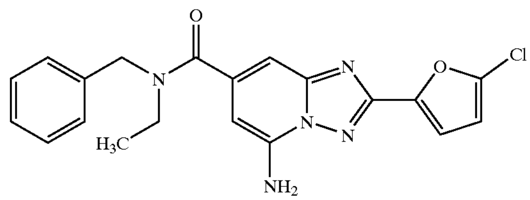 | 395.9 MH+ (100) |
| 262 | 2.9 | 106.8 | 36.8 | 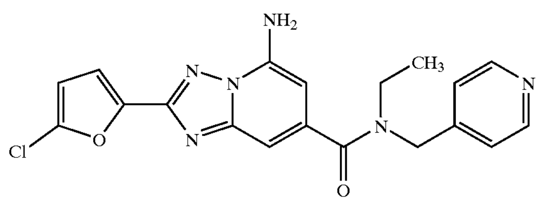 | 396.8 MH+ (100) |
| 263 | 39.8 | 304.1 | 7.6 | 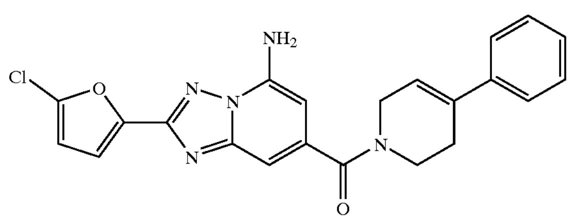 | 419.9 MH+ (100) |
| 264 | 6.5 | 277.4 | 42.7 | 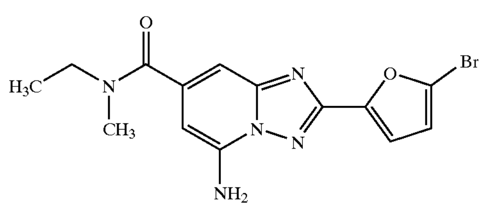 | 364.2 MH+ (100) |
| 265 | 7.4 | 563.9 | 76.2 | 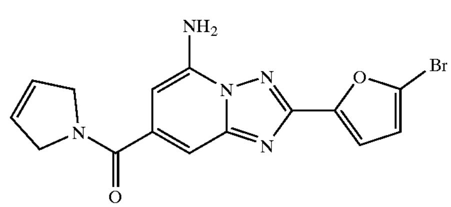 | 374.2 MH+ (100) |
| 266 | 3.1 | 246.1 | 79.4 | 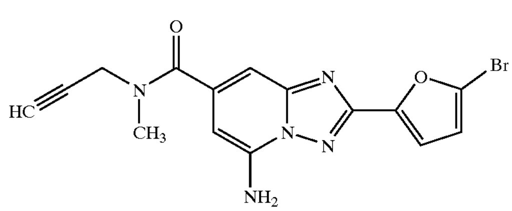 | 374.2 MH+ (100) |

-continued

| No. | Ki HA2A (nM) | Ki HA1 (nM) | selectivity (A1/A2a) | Structure | MW | MS m/e (%) |
|---|---|---|---|---|---|---|
| 267 | 4.3 | 180.6 | 42.0 | 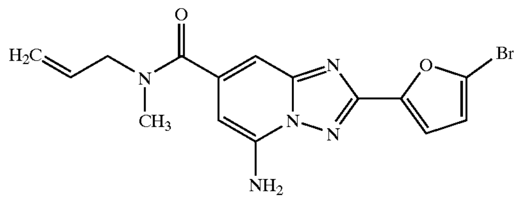 | 376.2 | MH+ (100) |
| 268 | 5.9 | 275.0 | 46.6 | 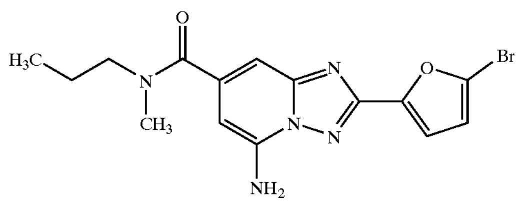 | 378.2 | MH+ (100) |
| 269 | 2.7 | 110.5 | 40.9 | 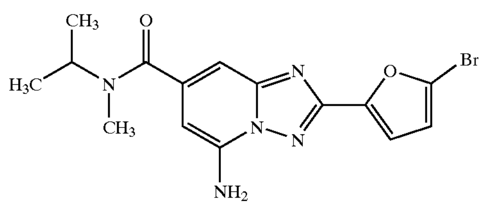 | 378.2 | MH+ (100) |
| 270 | 4.4 | 286.4 | 65.1 | 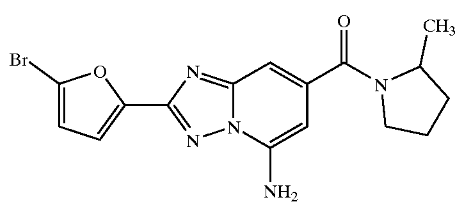 | 390.2 | MH+ (100) |
| 271 | 6.5 | 149.0 | 22.9 | 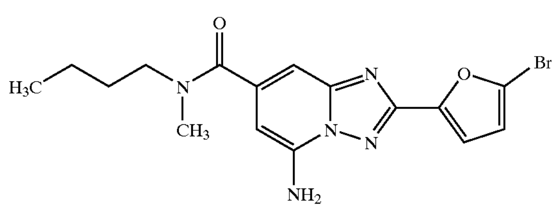 | 392.3 | MH+ (100) |
| 272 | 2.2 | 81.0 | 36.8 | 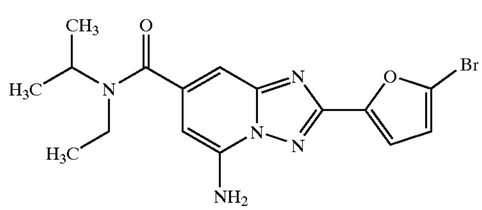 | 392.3 | MH+ (100) |
| 273 | 3.9 | 251.1 | 64.4 | 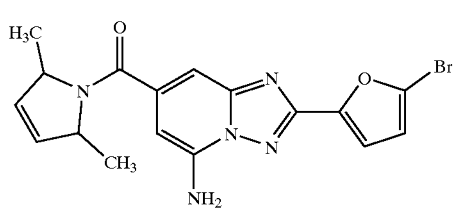 | 402.3 | MH+ (100) |

-continued

| No. | Ki HA2A (nM) | Ki HA1 (nM) | selectivity (A1/A2a) | Structure | MW MS m/e (%) |
|---|---|---|---|---|---|
| 274 | 2.8 | 116.4 | 41.6 | 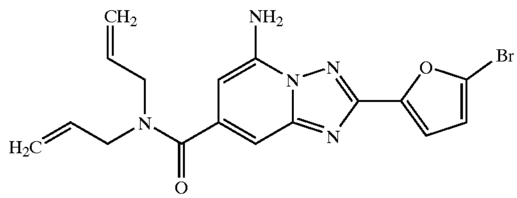 | 402.3 MH+ (100) |
| 275 | 5.4 | 208.9 | 38.7 | 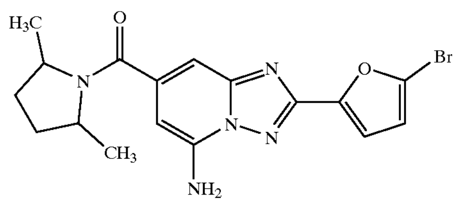 | 404.3 MH+ (100) |
| 276 | 10.1 | 228.7 | 22.6 | 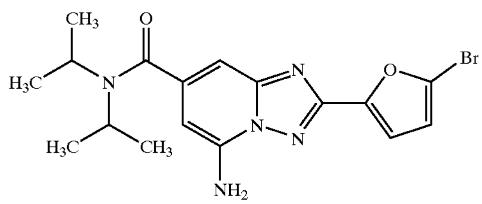 | 406.3 MH+ (100) |
| 277 | 3.2 | 128.8 | 40.3 | 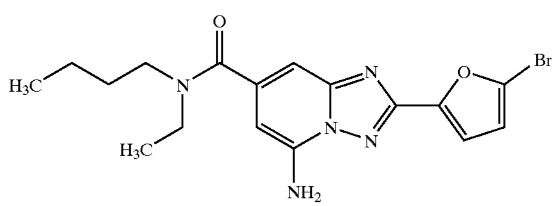 | 406.3 MH+ (100) |
| 278 | 5.6 | 94.3 | 16.8 | 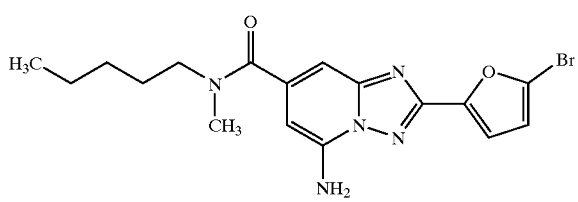 | 406.3 MH+ (100) |
| 279 | 124.4 | 1061.4 | 8.5 | 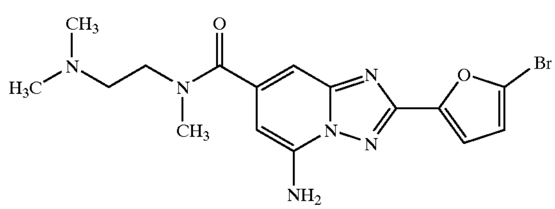 | 407.3 MH+ (100) |
| 280 | 157.1 | 6064.1 | 38.6 | 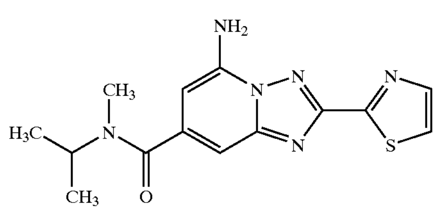 | 302.4 MH+ (100) |

-continued

| No. | Ki HA2A (nM) | Ki HA1 (nM) | selectivity (A1/A2a) | Structure | MW MS m/e (%) |
|---|---|---|---|---|---|
| 281 | 83.7 | 4341.7 | 51.9 | 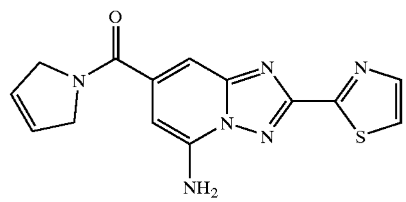 | 312.4 MH+ (100) |
| 282 | 85.2 | 4130.7 | 48.5 | 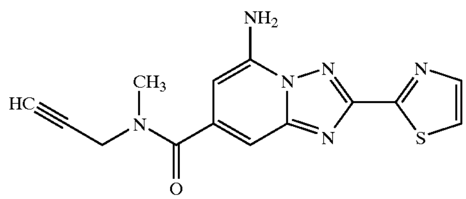 | 312.4 MH+ (100) |
| 283 | 116.1 | 3131.4 | 27.0 | 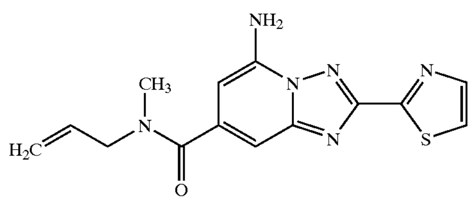 | 314.4 MH+ (100) |
| 284 | 131.7 | 3888.6 | 29.5 | 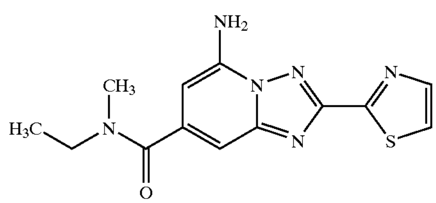 | 316.4 MH+ (100) |
| 285 | 83.5 | 2724.8 | 32.6 | 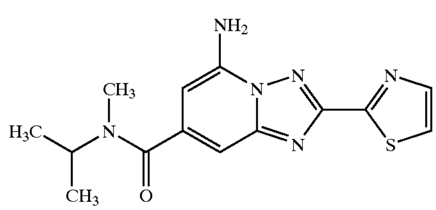 | 316.4 MH+ (100) |
| 286 | 32.4 | 2973.1 | 91.8 | 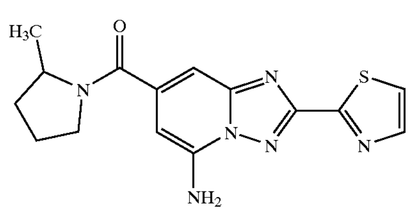 | 328.4 MH+ (100) |
| 287 | 142.3 | 2194.1 | 15.4 | 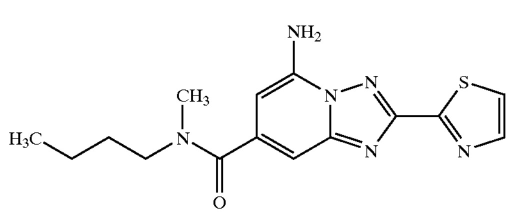 | 330.4 MH+ (100) |

-continued

| No. | Ki HA2A (nM) | Ki HA1 (nM) | selectivity (A1/A2a) | Structure | MW MS m/e (%) |
|---|---|---|---|---|---|
| 288 | 66.6 | 1396.6 | 21.0 | 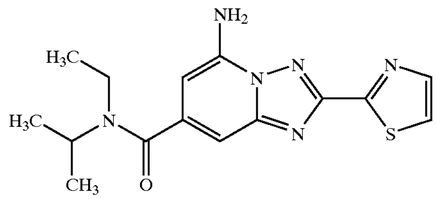 | 330.4 MH+ (100) |
| 289 | 55.3 | 2324.5 | 42.0 | 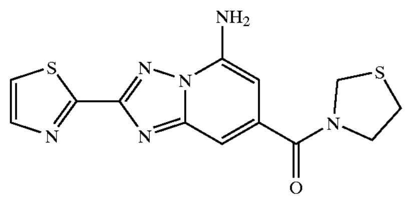 | 332.4 MH+ (100) |
| 290 | 57.6 | 1278.6 | 22.2 | 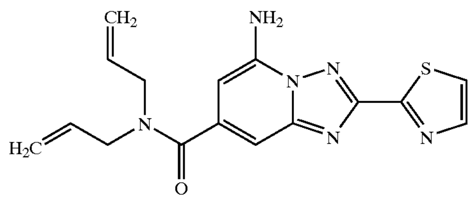 | 340.4 MH+ (100) |
| 291 | 89.5 | 1542.4 | 17.2 | 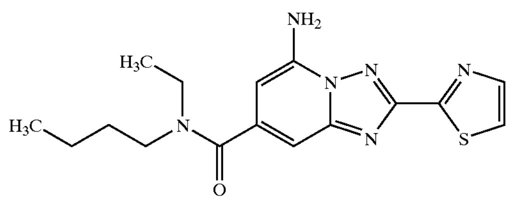 | 344.4 MH+ (100) |
| 292 | 108.1 | 1505.2 | 13.9 | 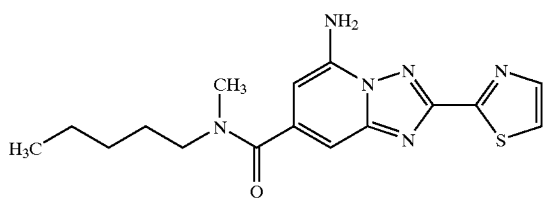 | 344.4 MH+ (100) |
| 293 | 24.1 | 527.9 | 21.9 | 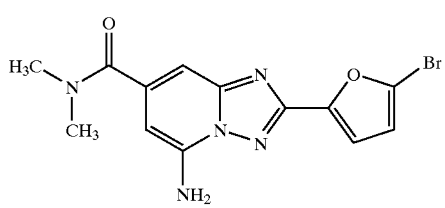 | 350.2 MH+ (100) |
| 294 | 4.1 | 143.4 | 35.0 | 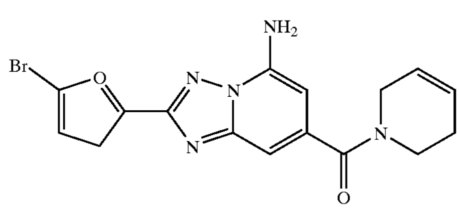 | 388.2 MH+ (100) |

-continued
| No. | Ki HA2A (nM) | Ki HA1 (nM) | selectivity (A1/A2a) | Structure | MW MS m/e (%) |
|---|---|---|---|---|---|
| 295 | 2.9 | 130.3 | 44.9 | 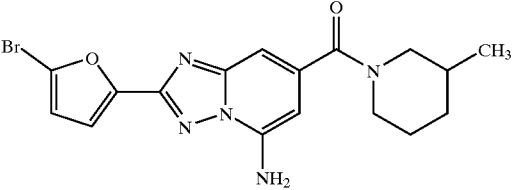 | 404.3 MH+ (100) |
| 296 | 1.7 | 52.7 | 31.0 | 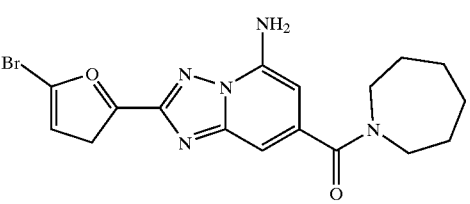 | 404.3 MH+ (100) |
| 297 | 9.1 | 252.6 | 27.8 | 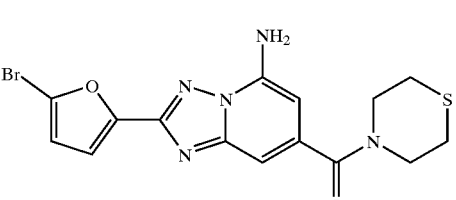 | 408.3 MH+ (100) |
| 298 | 2.2 | 94.0 | 42.7 | 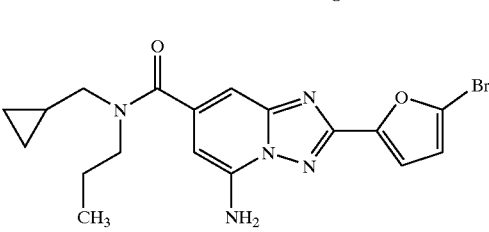 | 418.3 MH+ (100) |
| 299 | 123.4 | 1598.3 | 13.0 | 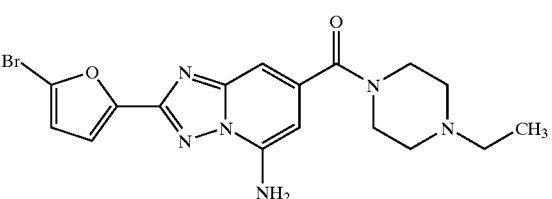 | 419.3 MH+ (100) |
| 300 | 74.7 | 385.4 | 5.2 | 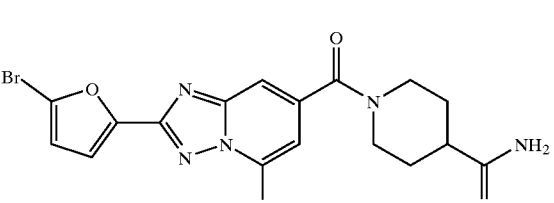 | 433.3 MH+ (100) |
| 301 | 62.1 | 1896.2 | 30.5 | 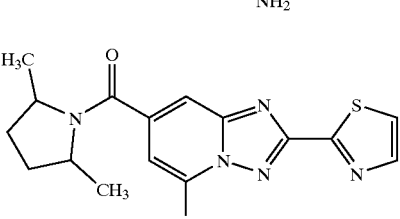 | 342.4 MH+ (100) |

-continued

| No. | Ki HA2A (nM) | Ki HA1 (nM) | selectivity (A1/A2a) | Structure | MW MS m/e (%) |
|---|---|---|---|---|---|
| 302 | 104.1 | 2023.4 | 19.4 | 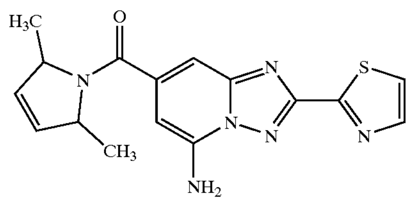 | 340.4 MH+ (100) |
| 303 | 148.8 | 1297.2 | 8.7 | 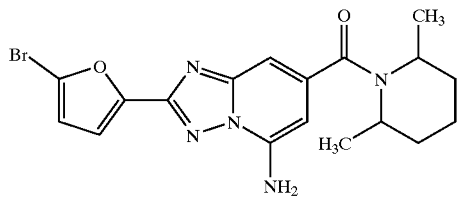 | 418.3 MH+ (100) |
| 304 | 9.3 | 381.7 | 41.0 | 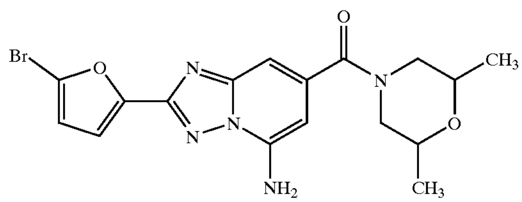 | 420.3 MH+ (100) |
| 305 | 5.2 | 139.3 | 26.8 | 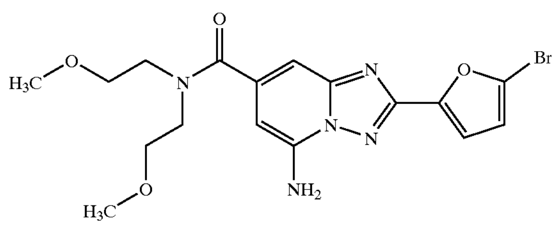 | 438.3 MH+ (100) |
| 306 | 4.8 | 87.8 | 18.3 | 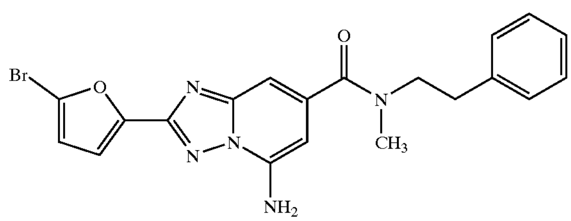 | 440.3 MH+ (100) |
| 307 | 1.7 | 21.2 | 12.5 | 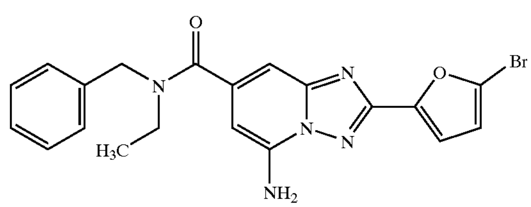 | 440.3 MH+ (100) |
| 308 | 9.8 | 463.0 | 47.2 | 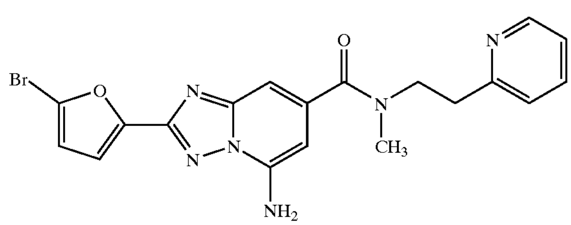 | 441.3 MH+ (100) |

-continued

| No. | Ki HA2A (nM) | Ki HA1 (nM) | selectivity (A1/A2a) | Structure | MW MS m/e (%) |
|---|---|---|---|---|---|
| 309 | 49.5 | 488.5 | 9.9 | 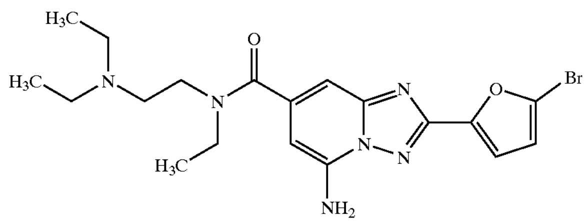 | 449.4 MH+ (100) |
| 310 | 147.8 | 313.8 | 2.1 | 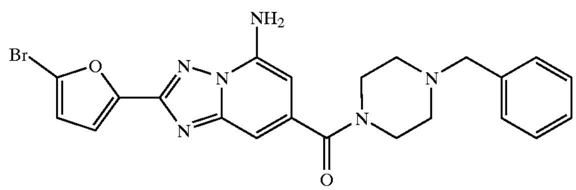 | 481.4 MH+ (100) |
| 311 | 25.8 | 576.6 | 22.3 | 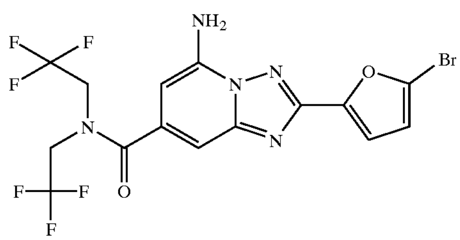 | 486.2 MH+ (100) |
| 312 | 21.8 | 227.2 | 10.4 | 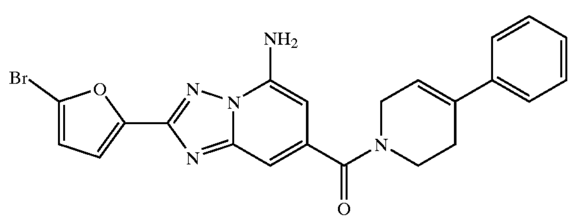 | 464.3 MH+ (100) |
| 313 | 1.2 | 17.8 | 14.8 | 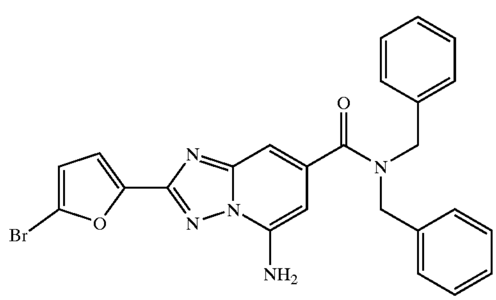 | 502.4 MH+ (100) |
| 314 | 1.2 | 59.1 | 49.3 | 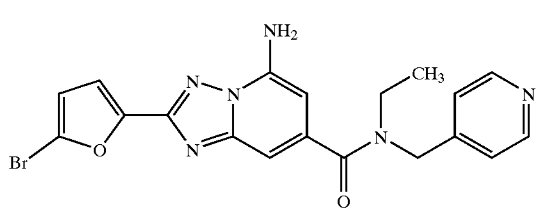 | 441.3 MH+ (100) |

| No. | Ki HA2A (nM) | Ki HA1 (nM) | selectivity (A1/A2a) | Structure | MW MS m/e (%) |
|---|---|---|---|---|---|
| 315 | 97.5 | 1989.3 | 20.4 | 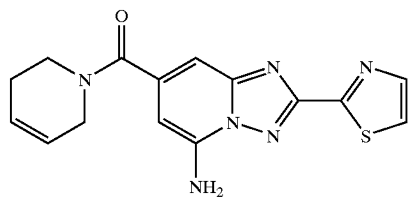 | 326.4 MH+ (100) |
| 316 | 72.3 | 2194.1 | 30.3 | 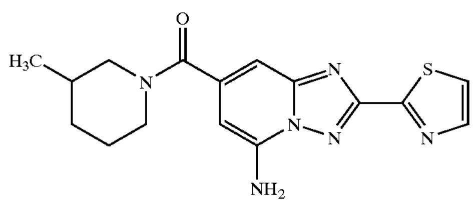 | 342.4 MH+ (100) |
| 317 | 34.5 | 1160.7 | 33.6 | 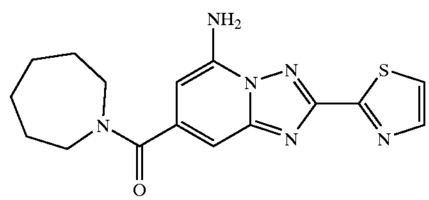 | 342.4 MH+ (100) |
| 318 | 331.6 | | | 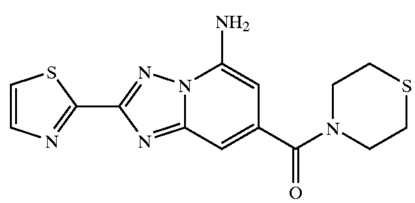 | 346.4 MH+ (100) |
| 319 | 87.0 | 1244.5 | 14.3 | 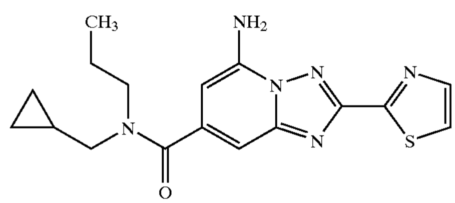 | 356.5 MH+ (100) |
| 320 | 82.7 | 613.9 | 7.4 | 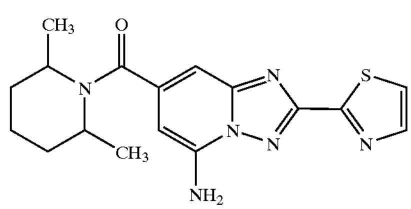 | 356.5 MH+ (100) |
| 321 | 319.0 | | | 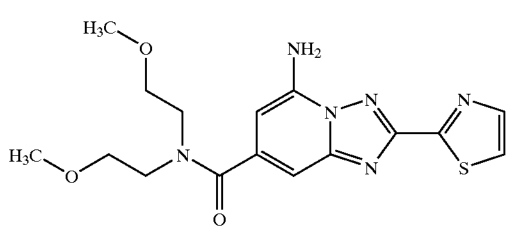 | 376.4 MH+ (100) |

-continued

| No. | Ki HA2A (nM) | Ki HA1 (nM) | selectivity (A1/A2a) | Structure | MW MS m/e (%) |
|---|---|---|---|---|---|
| 322 | 127.2 | 1216.6 | 9.6 | 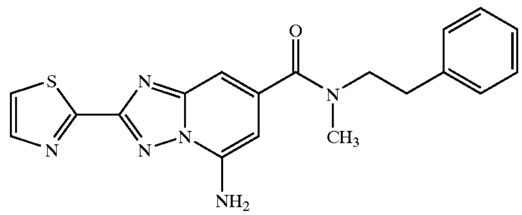 | 378.5 MH+ (100) |
| 323 | 25.2 | 342.0 | 13.6 | 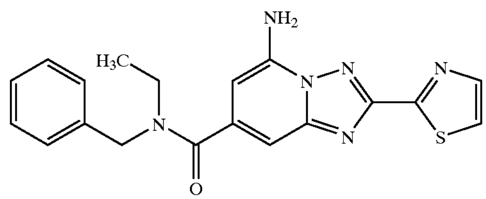 | 378.5 MH+ (100) |
| 324 | 295.4 | | | 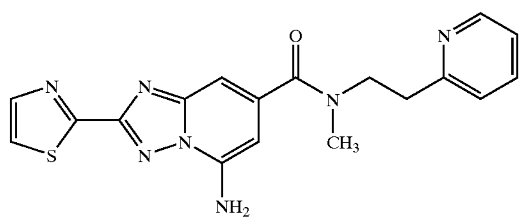 | 379.4 MH+ (100) |
| 325 | 37.6 | 1325.2 | 35.2 | 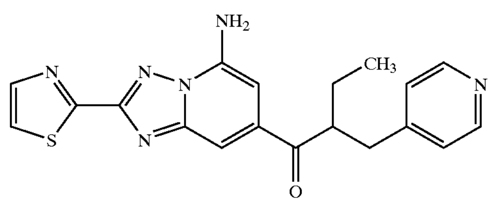 | 379.4 MH+ (100) |
| 326 | 372.8 | | | 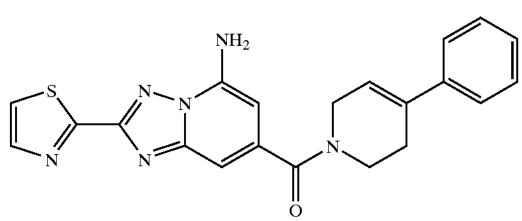 | 402.5 MH+ (100) |
| 327 | 5.8 | 128.5 | 22.2 | 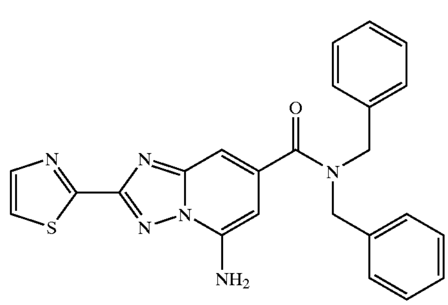 | 440.5 MH+ (100) |

-continued

| No. | Ki HA2A (nM) | Ki HA1 (nM) | selectivity (A1/A2a) | Structure | MW MS m/e (%) |
|---|---|---|---|---|---|
| 328 | 31.7 | 1238.3 | 39.1 | 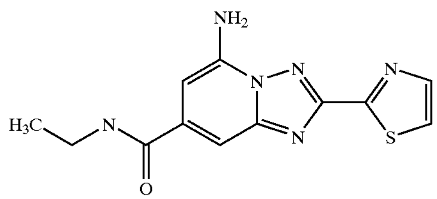 | 288.3 MH+ (100) |
| 329 | 47.3 | 1980.0 | 41.9 | 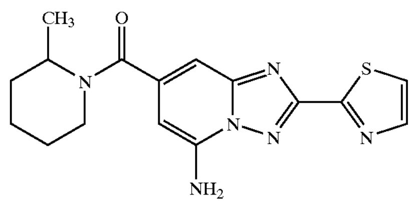 | 342.4 MH+ (100) |
| 330 | 64.4 | 2777.6 | 43.1 | 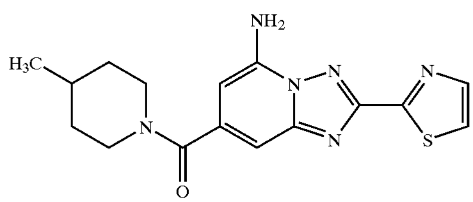 | 342.4 MH+ (100) |
| 331 | 87.5 | 2703.1 | 30.9 | 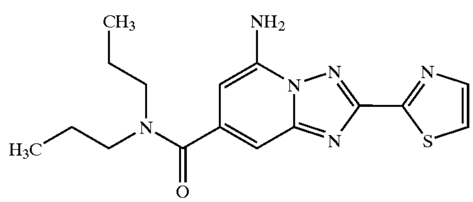 | 344.4 MH+ (100) |
| 332 | 17.2 | 844.1 | 49.1 | 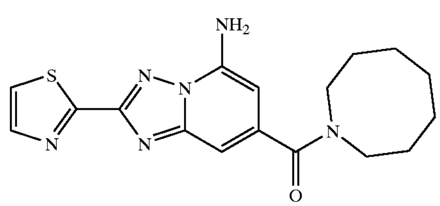 | 356.5 MH+ (100) |
| 333 | 36.1 | 1728.6 | 47.9 | 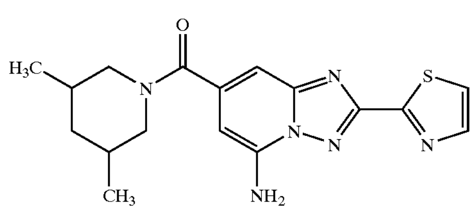 | 356.5 MH+ (100) |
| 334 | 98.0 | 1790.7 | 18.3 | 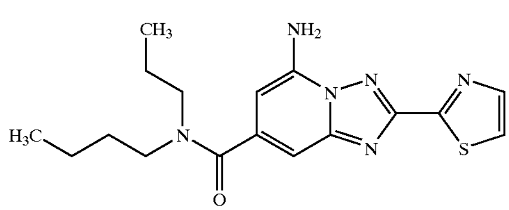 | 358.5 MH+ (100) |

| No. | Ki HA2A (nM) | Ki HA1 (nM) | selectivity (A1/A2a) | Structure | MW | MS m/e (%) |
|---|---|---|---|---|---|---|
| 335 | 25.2 | 355.3 | 14.1 | 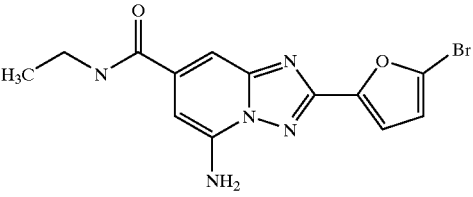 | 350.2 | MH+ (100) |
| 336 | 2.2 | 65.7 | 29.9 | 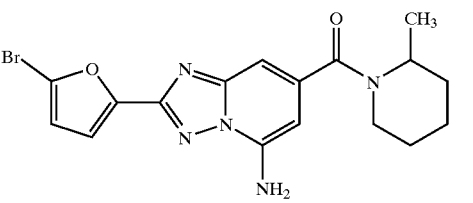 | 404.3 | MH+ (100) |
| 337 | 6.4 | 183.1 | 28.6 | 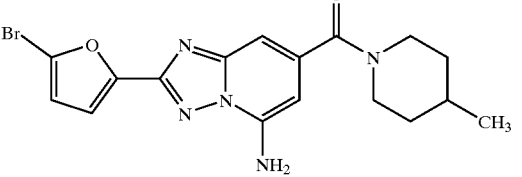 | 404.3 | MH+ (100) |
| 338 | 3.1 | 199.6 | 64.4 | 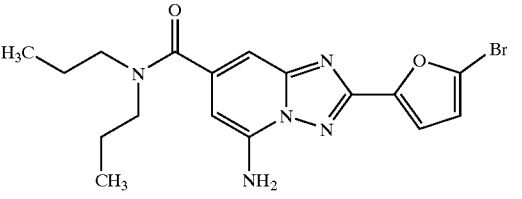 | 406.3 | MH+ (100) |
| 339 | 1.3 | 37.0 | 28.5 | 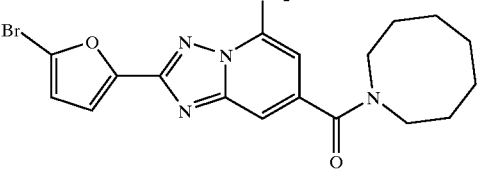 | 418.3 | MH+ (100) |
| 340 | 2.6 | 77.3 | 29.7 | 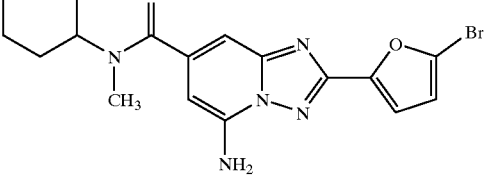 | 418.3 | MH+ (100) |
| 341 | 1.7 | 119.5 | 70.3 | 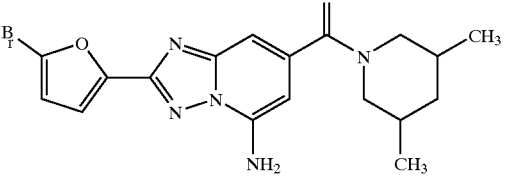 | 418.3 | MH+ (100) |

-continued

| No. | Ki HA2A (nM) | Ki HA1 (nM) | selectivity (A1/A2a) | Structure | MW | MS m/e (%) |
|---|---|---|---|---|---|---|
| 342 | 3.0 | 141.8 | 47.3 | 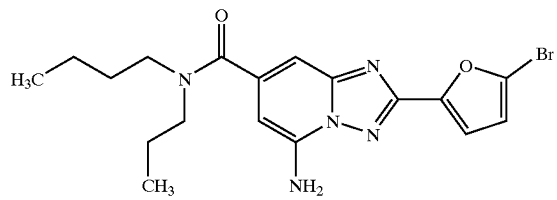 | 420.3 | MH+ (100) |
| 343 | 2.7 | 42.2 | 15.6 | 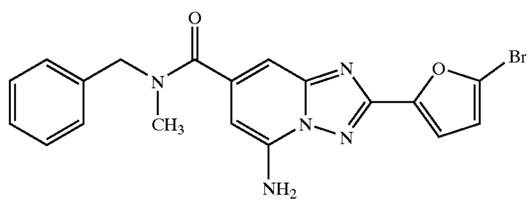 | 426.3 | MH+ (100) |
| 344 | 1.6 | 71.7 | 44.8 | 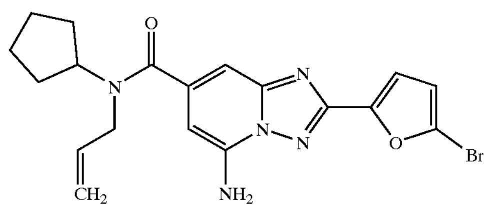 | 430.3 | MH+ (100) |
| 345 | 2.0 | 62.1 | 31.1 | 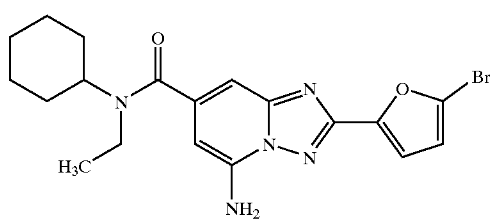 | 432.3 | MH+ (100) |
| 346 | 2.4 | 102.4 | 42.7 | 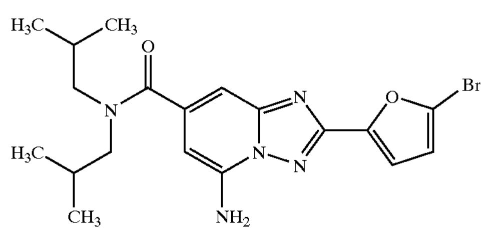 | 434.3 | MH+ (100) |
| 347 | 13.3 | 235.6 | 17.7 | 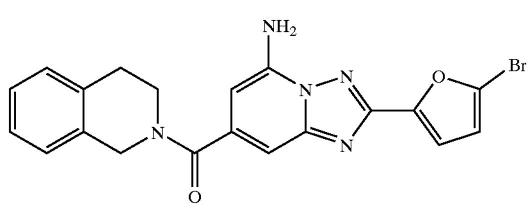 | 438.3 | MH+ (100) |
| 348 | 2.6 | 67.0 | 25.8 | 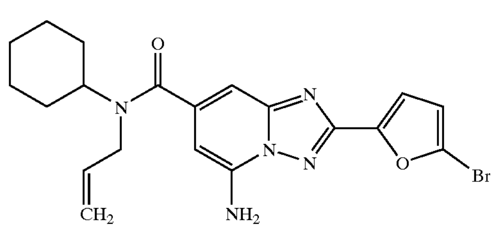 | 444.3 | MH+ (100) |

-continued

| No. | Ki HA2A (nM) | Ki HA1 (nM) | selectivity (A1/A2a) | Structure | MW MS m/e (%) |
|---|---|---|---|---|---|
| 349 | 2.9 | 64.7 | 22.3 | 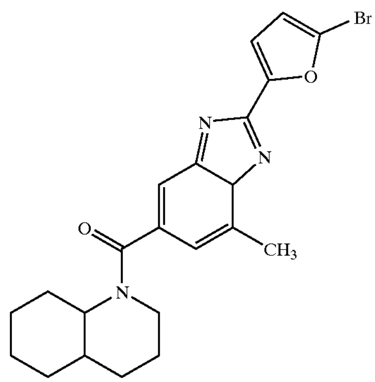 | 444.3 MH+ (100) |
| 350 | 5.8 | 167.0 | 28.8 | 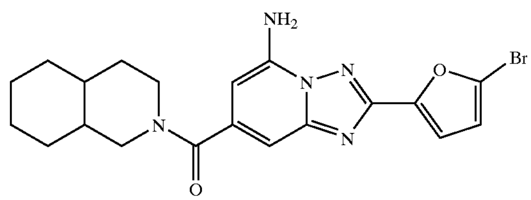 | 444.3 MH+ (100) |
| 351 | 2.9 | 77.3 | 26.7 | 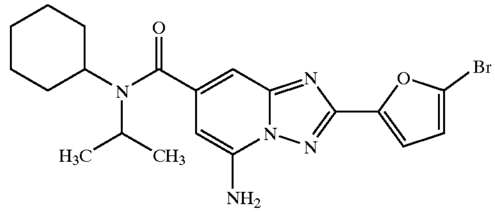 | 446.4 MH+ (100) |
| 352 | 4.0 | 143.7 | 35.9 | 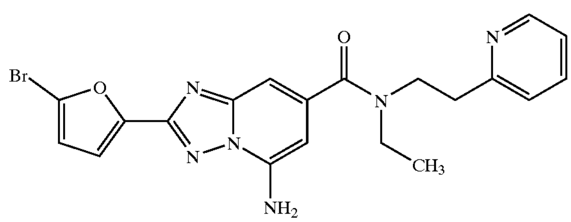 | 455.3 MH+ (100) |
| 353 | 81.5 | 1036.6 | 12.7 | 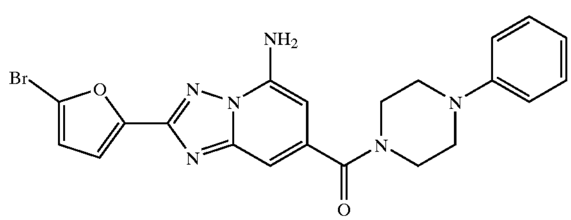 | 467.3 MH+ (100) |
| 354 | 2.9 | 45.5 | 15.7 | 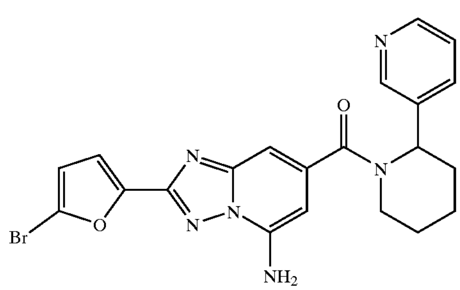 | 467.3 MH+ (100) |

-continued
| No. | Ki HA2A (nM) | Ki HA1 (nM) | selectivity (A1/A2a) | Structure | MW MS m/e (%) |
|---|---|---|---|---|---|
| 355 | 47.0 | 285.8 | 6.1 | 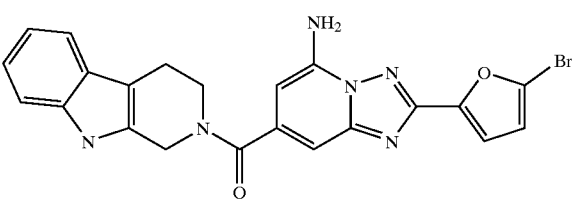 | 477.3 MH+ (100) |
| 356 | 8.5 | 1064.5 | 125.2 | 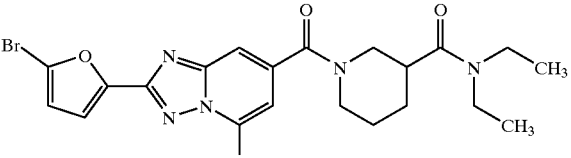 | 489.4 MH+ (100) |
| 357 | 145.3 | 4838.3 | 33.3 | Chiral 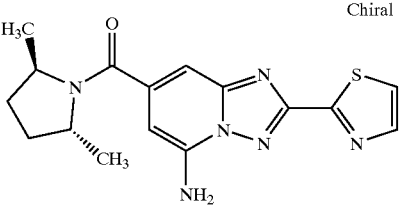 | 342.4 MH+ (100) |
| 358 | 74.7 | 1719.3 | 23.0 | 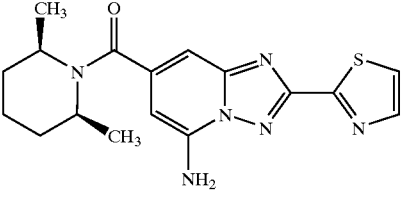 | 356.5 MH+ (100) |
| 359 | 7.3 | 934.1 | 128.0 | Chiral 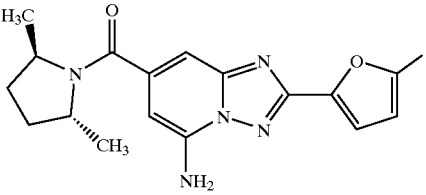 | 404.3 MH+ (100) |
| 360 | 7.7 | 422.4 | 54.9 | 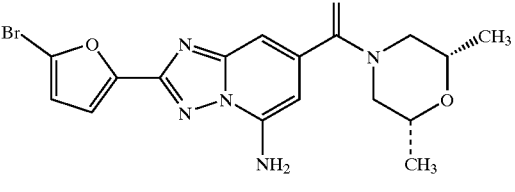 | 420.3 MH+ (100) |

This table lists the names of representative compounds, Examples 21 to 360, whose affinity values, selectivity ratio, structural formulae and characterization are given in the table above.

| Example No. | Name |
|---|---|
| 21 | 5-Amino-2-(5-bromo-furan-2-yl)-[1,2,4]triazolo[1,5-a]-pyridine-7-carboxylic acid diethylamide |
| 22 | [5-Amino-2-(5-bromo-furan-2-yl)-[1,2,4]triazolo[1,5-a]-pyridin-7-yl]-pyrrolidin-1-yl-methanone |
| 23 | [5-Amino-2-(5-bromo-furan-2-yl)-[1,2,4]triazolo[1,5-a]-pyridin-7-yl]-piperidin-1-yl-methanone |
| 24 | 5-Amino-2-(5-methyl-thiophen-2-yl)-[1,2,4]triazolo[1,5-a]-pyridine-7-carboxylic acid cyclohexyl-ethyl-amide |
| 25 | (5-Amino-2-thiazol-2-yl-[1,2,4]triazolo[1,5-a]pyridin-7-yl)-pyrrolidin-1-yl-methanone |
| 26 | 5-Amino-2-(5-bromo-furan-2-yl)-[1,2,4]triazolo[1,5-a]-pyridine-7-carboxylic acid benzyl-isopropyl-amide |
| 27 | [5-Amino-2-(5-methyl-furan-2-yl)-[1,2,4]triazolo[1,5-a]-pyridin-7-yl]-pyrrolidin-1-yl-methanone |
| 28 | [5-Amino-2-(5-methyl-furan-2-yl)-[1,2,4]triazolo[1,5-a]-pyridin-7-yl]-piperidin-1-yl-methanone |
| 29 | 5-Amino-2-pyridin-2-yl-[1,2,4]triazolo[1,5-a]pyridine-7-carboxylic acid benzyl-ethyl-amide |
| 30 | (5-Amino-2-pyridin-2-yl-[1,2,4]triazolo[1,5-a]pyridin-7-yl)-(3,4-dihydro-1H-isoquinolin-2-yl)-methanone |
| 31 | 5-Amino-2-pyridin-2-yl-[1,2,4]triazolo[1,5-a]pyridine-7-carboxylic acid cyclohexyl-ethyl-amide |
| 32 | 5-Amino-2-pyridin-2-yl-[1,2,4]triazolo[1,5-a]pyridine-7-carboxylic acid benzyl-methyl-amide |
| 33 | 5-Amino-2-pyridin-2-yl-[1,2,4]triazolo[1,5-a]pyridine-7-carboxylic acid cyclohexyl-methyl-amide |
| 34 | (5-Amino-2-pyridin-2-yl-[1,2,4]triazolo[1,5-a]pyridin-7-yl)-piperidin-1-yl-methanone |
| 35 | 5-Amino-2-pyridin-2-yl-[1,2,4]triazolo[1,5-a]pyridine-7-carboxylic acid diethylamide |
| 36 | 5-Amino-2-pyridin-2-yl-[1,2,4]triazolo[1,5-a]pyridine-7-carboxylic acid benzyl-butyl-amide |
| 37 | 5-Amino-2-(3-methyl-thiophen-2-yl)-[1,2,4]triazolo[1,5-a]-pyridine-7-carboxylic acid cyclohexylamide |
| 38 | 5-Amino-2-pyridin-2-yl-[1,2,4]triazolo[1,5-a]pyridine-7-carboxylic acid 2-bromo-benzylamide |
| 39 | 5-Amino-2-pyridin-2-yl-[1,2,4]triazolo[1,5-a]pyridine-7-carboxylic acid 2-chloro-benzylamide |
| 40 | 5-Amino-2-pyridin-2-yl-[1,2,4]triazolo[1,5-a]pyridine-7-carboxylic acid [2-(2-fluoro-phenyl)-ethyl]-amide |
| 41 | 5-Amino-2-pyridin-2-yl-[1,2,4]triazolo[1,5-a]pyridine-7-carboxylic acid 2-methoxy-benzylamide |
| 42 | 5-Amino-2-pyridin-2-yl-[1,2,4]triazolo[1,5-a]pyridine-7-carboxylic acid 4-methoxy-benzylamide |
| 43 | 5-Amino-2-pyridin-2-yl-[1,2,4]triazolo[1,5-a]pyridine-7-carboxylic acid 4-fluoro-benzylamide |
| 44 | 5-Amino-2-pyridin-2-yl-[1,2,4]triazolo[1,5-a]pyridine-7-carboxylic acid (1-phenyl-ethyl)-amide |
| 45 | 5-Amino-2-pyridin-2-yl-[1,2,4]triazolo[1,5-a]pyridine-7-carboxylic acid [2-(2-methoxy-phenyl)-ethyl]-amide |
| 46 | 5-Amino-2-pyridin-2-yl-[1,2,4]triazolo[1,5-a]pyridine-7-carboxylic acid benzylamide |
| 47 | 5-Amino-2-pyridin-2-yl-[1,2,4]triazolo[1,5-a]pyridine-7-carboxylic acid hexylamide |
| 48 | 5-Amino-2-pyridin-2-yl-[1,2,4]triazolo[1,5-a]pyridine-7-carboxylic acid cyclohexylamide |
| 49 | 5-Amino-2-pyridin-2-yl-[1,2,4]triazolo[1,5-a]pyridine-7-carboxylic acid butylamide |
| 50 | 5-Amino-2-pyridin-2-yl-[1,2,4]triazolo[1,5-a]pyridine-7-carboxylic acid [2-(2-chloro-phenyl)-ethyl]-amide |
| 51 | 5-Amino-2-(5-methoxy-thiophen-2-yl)-[1,2,4]triazolo[1,5-a]-pyridine-7-carboxylic acid dibenzylamide |
| 52 | 5-Amino-2-(5-methoxy-thiophen-2-yl)-[1,2,4]triazolo[1,5-a]-pyridine-7-carboxylic acid 2-bromo-benzylamide |
| 53 | 5-Amino-2-(5-methoxy-thiophen-2-yl)-[1,2,4]triazolo[1,5-a]-pyridine-7-carboxylic acid benzyl-(2-dimethylamino-ethyl)-amide |
| 54 | 5-Amino-2-(5-methoxy-thiophen-2-yl)-[1,2,4]triazolo[1,5-a]-pyridine-7-carboxylic acid [2-(2-methoxy-phenyl)-ethyl]-amide |
| 55 | 5-Amino-2-(5-methoxy-thiophen-2-yl)-[1,2,4]triazolo[1,5-a]-pyridine-7-carboxylic acid benzyl-isopropyl-amide |
| 56 | 5-Amino-2-(5-methoxy-thiophen-2-yl)-[1,2,4]triazolo[1,5-a]-pyridine-7-carboxylic acid 2-chloro-benzylamide |
| 57 | 5-Amino-2-(5-methoxy-thiophen-2-yl)-[1,2,4]triazolo[1,5-a]-pyridine-7-carboxylic acid [2-(2-fluoro-phenyl)-ethyl]-amide |
| 58 | 5-Amino-2-(5-methoxy-thiophen-2-yl)-[1,2,4]triazolo[1,5-a]-pyridine-7-carboxylic acid 2-methoxy-benzylamide |
| 59 | 5-Amino-2-(5-methoxy-thiophen-2-yl)-[1,2,4]triazolo[1,5-a]-pyridine-7-carboxylic acid benzyl-ethyl-amide |
| 60 | 5-Amino-2-(5-methoxy-thiophen-2-yl)-[1,2,4]triazolo[1,5-a]-pyridine-7-carboxylic acid (1-phenyl-ethyl)-amide |
| 61 | 5-Amino-2-(5-methoxy-thiophen-2-yl)-[1,2,4]triazolo[1,5-a]-pyridine-7-carboxylic acid (pyridin-3-ylmethyl)-amide |
| 62 | 5-Amino-2-(5-methoxy-thiophen-2-yl)-[1,2,4]triazolo[1,5-a]-pyridine-7-carboxylic acid benzylamide |
| 63 | 5-Amino-2-(5-methoxy-thiophen-2-yl)-[1,2,4]triazolo[1,5-a]-pyridine-7-carboxylic acid hexylamide |
| 64 | 5-Amino-2-(5-methoxy-thiophen-2-yl)-[1,2,4]triazolo[1,5-a]-pyridine-7-carboxylic acid cyclohexylamide |
| 65 | 5-Amino-2-(5-methoxy-thiophen-2-yl)-[1,2,4]triazolo[1,5-a]-pyridine-7-carboxylic acid ethyl-isopropyl-amide |
| 66 | [5-Amino-2-(5-methoxy-thiophen-2-yl)-[1,2,4]triazolo[1,5-a]-pyridin-7-yl]-piperidin-1-yl-methanone |
| 67 | 5-Amino-2-(5-methoxy-thiophen-2-yl)-[1,2,4]triazolo[1,5-a]-pyridine-7-carboxylic acid butylamide |
| 68 | 5-Amino-2-(5-methoxy-thiophen-2-yl)-[1,2,4]triazolo[1,5-a]-pyridine-7-carboxylic acid diethylamide |
| 69 | [5-Amino-2-(5-methoxy-thiophen-2-yl)-[1,2,4]triazolo[1,5-a]-pyridin-7-yl]-pyrrolidin-1-yl-methanone |
| 70 | 5-Amino-2-(5-methoxy-thiophen-2-yl)-[1,2,4]triazolo[1,5-a]-pyridine-7-carboxylic acid cyclobutylamide |
| 71 | 5-Amino-2-(5-methoxy-thiophen-2-yl)-[1,2,4]triazolo[1,5-a]-pyridine-7-carboxylic acid propylamide |
| 72 | 5-Amino-2-(5-methoxy-thiophen-2-yl)-[1,2,4]triazolo[1,5-a]-pyridine-7-carboxylic acid cyclopropylamide |
| 73 | 5-Amino-2-(5-methoxy-thiophen-2-yl)-[1,2,4]triazolo[1,5-a]-pyridine-7-carboxylic acid benzyl-butyl-amide |
| 74 | 5-Amino-2-(5-methoxy-thiophen-2-yl)-[1,2,4]triazolo[1,5-a]-pyridine-7-carboxylic acid cycloheptylamide |
| 75 | 5-Amino-2-(5-methoxy-thiophen-2-yl)-[1,2,4]triazolo[1,5-a]-pyridine-7-carboxylic acid benzyl-phenethyl-amide |
| 76 | 5-Amino-2-(5-methoxy-thiophen-2-yl)-[1,2,4]triazolo[1,5-a]-pyridine-7-carboxylic acid ethyl-(2-fluoro-benzyl)-amide |
| 77 | 5-Amino-2-(5-methoxy-thiophen-2-yl)-[1,2,4]triazolo[1,5-a]-pyridine-7-carboxylic acid methyl-phenethyl-amide |
| 78 | 5-Amino-2-(5-methoxy-thiophen-2-yl)-[1,2,4]triazolo[1,5-a]-pyridine-7-carboxylic acid [2-(2-chloro-phenyl)-ethyl]-amide |
| 79 | 5-Amino-2-pyridin-3-yl-[1,2,4]triazolo[1,5-a]pyridine-7-carboxylic acid 2-bromo-benzylamide |
| 80 | 5-Amino-2-pyridin-3-yl-[1,2,4]triazolo[1,5-a]pyridine-7-carboxylic acid butylamide |
| 81 | 5-Amino-2-pyridin-3-yl-[1,2,4]triazolo[1,5-a]pyridine-7-carboxylic acid cyclobutylamide |
| 82 | 5-Amino-2-pyridin-3-yl-[1,2,4]triazolo[1,5-a]pyridine-7-carboxylic acid propylamide |
| 83 | 5-Amino-2-(1H-pyrrol-2-yl)-[1,2,4]triazolo[1,5-a]pyridine-7-carboxylic acid 2-chloro-benzylamide |
| 84 | 5-Amino-2-(1H-pyrrol-2-yl)-[1,2,4]triazolo[1,5-a]pyridine-7-carboxylic acid benzyl-butyl-amide |
| 85 | 5-Amino-2-(1H-pyrrol-2-yl)-[1,2,4]triazolo[1,5-a]pyridine-7-carboxylic acid ethyl-(2-fluoro-benzyl)-amide |
| 86 | 5-Amino-2-pyridin-3-yl-[1,2,4]triazolo[1,5-a]pyridine-7-carboxylic acid benzyl-isopropyl-amide |
| 87 | 5-Amino-2-pyridin-3-yl-[1,2,4]triazolo[1,5-a]pyridine-7-carboxylic acid 2-methoxy-benzylamide |
| 88 | 5-Amino-2-pyridin-3-yl-[1,2,4]triazolo[1,5-a]pyridine-7-carboxylic acid benzyl-ethyl-amide |
| 89 | 5-Amino-2-pyridin-3-yl-[1,2,4]triazolo[1,5-a]pyridine-7-carboxylic acid benzyl-butyl-amide |
| 90 | 5-Amino-2-pyridin-3-yl-[1,2,4]triazolo[1,5-a]pyridine-7-carboxylic acid benzyl-phenethyl-amide |
| 91 | 5-Amino-2-pyridin-3-yl-[1,2,4]triazolo[1,5-a]pyridine-7-carboxylic acid ethyl-(2-fluoro-benzyl)-amide |
| 92 | 5-Amino-2-(1H-pyrrol-2-yl)-[1,2,4]triazolo[1,5-a]pyridine-7-carboxylic acid 2-bromo-benzylamide |

| Example No. | Name |
|---|---|
| 93 | 5-Amino-2-(1H-pyrrol-2-yl)-[1,2,4]triazolo[1,5-a]pyridine-7-carboxylic acid 2-methoxy-benzylamide |
| 94 | 5-Amino-2-(1H-pyrrol-2-yl)-[1,2,4]triazolo[1,5-a]pyridine-7-carboxylic acid benzyl-ethyl-amide |
| 95 | 5-Amino-2-(1H-pyrrol-2-yl)-[1,2,4]triazolo[1,5-a]pyridine-7-carboxylic acid cyclobutylamide |
| 96 | 5-Amino-2-(1H-pyrrol-2-yl)-[1,2,4]triazolo[1,5-a]pyridine-7-carboxylic acid benzyl-phenethyl-amide |
| 97 | 5-Amino-2-thiazol-2-yl-[1,2,4]triazolo[1,5-a]pyridine-7-carboxylic acid 3,4,5-trimethoxy-benzylamide |
| 98 | 5-Amino-2-furan-3-yl-[1,2,4]triazolo[1,5-a]pyridine-7-carboxylic acid butylamide |
| 99 | (5-Amino-2-furan-3-yl-[1,2,4]triazolo[1,5-a]pyridin-7-yl)-pyrrolidin-1-yl-methanone |
| 100 | 5-Amino-2-(5-methyl-furan-2-yl)-[1,2,4]triazolo[1,5-a]-pyridine-7-carboxylic acid cyclohexyl-methyl-amide |
| 101 | 5-Amino-2-(2-hydroxy-phenyl)-[1,2,4]triazolo[1,5-a]-pyridine-7-carboxylic acid diethylamide |
| 102 | [5-Amino-2-(2-hydroxy-phenyl)-[1,2,4]triazolo[1,5-a]-pyridin-7-yl]-piperidin-1-yl-methanone |
| 103 | (5-Amino-2-thiazol-2-yl-[1,2,4]triazolo[1,5-a]pyridin-7-yl)-piperidin-1-yl-methanone |
| 104 | 5-Amino-2-furan-2-yl-[1,2,4]triazolo[1,5-a]pyridine-7-carboxylic acid butylamide |
| 105 | 5-Amino-2-furan-2-yl-[1,2,4]triazolo[1,5-a]pyridine-7-carboxylic acid diethylamide |
| 106 | (5-Amino-2-furan-2-yl-[1,2,4]triazolo[1,5-a]pyridin-7-yl)-pyrrolidin-1-yl-methanone |
| 107 | (5-Amino-2-furan-2-yl-[1,2,4]triazolo[1,5-a]pyridin-7-yl)-piperidin-1-yl-methanone |
| 108 | (5-Amino-2-furan-2-yl-[1,2,4]triazolo[1,5-a]pyridin-7-yl)-morpholin-4-yl-methanone |
| 109 | 5-Amino-2-furan-2-yl-[1,2,4]triazolo[1,5-a]pyridine-7-carboxylic acid 2-chloro-benzylamide |
| 110 | 5-Amino-2-furan-2-yl-[1,2,4]triazolo[1,5-a]pyridine-7-carboxylic acid 2-bromo-benzylamide |
| 111 | 5-Amino-2-furan-2-yl-[1,2,4]triazolo[1,5-a]pyridine-7-carboxylic acid 3,4,5-trimethoxy-benzylamide |
| 112 | 5-Amino-2-(5-methyl-furan-2-yl)-[1,2,4]triazolo[1,5-a]-pyridine-7-carboxylic acid 3,4,5-trimethoxy-benzylamide |
| 113 | 5-Amino-2-(5-methyl-thiophen-2-yl)-[1,2,4]triazolo[1,5-a]-pyridine-7-carboxylic acid cyclohexyl-methyl-amide |
| 114 | [5-Amino-2-(5-methyl-thiophen-2-yl)-[1,2,4]triazolo[1,5-a]-pyridin-7-yl]-piperidin-1-yl-methanone |
| 115 | [5-Amino-2-(5-methyl-thiophen-2-yl)-[1,2,4]triazolo[1,5-a]-pyridin-7-yl]-morpholin-4-yl-methanone |
| 116 | 5-Amino-2-(5-methyl-thiophen-2-yl)-[1,2,4]triazolo-[1,5-a]pyridine-7-carboxylic acid benzyl-methyl-amide |
| 117 | 5-Amino-2-(5-methyl-thiophen-2-yl)-[1,2,4]triazolo-[1,5-a]pyridine-7-carboxylic acid benzyl-isopropyl-amide |
| 118 | [5-Amino-2-(2-hydroxy-phenyl)-[1,2,4]triazolo[1,5-a]-pyridin-7-yl]-pyrrolidin-1-yl-methanone |
| 119 | 5-Amino-2-thiazol-2-yl-[1,2,4]triazolo[1,5-a]-pyridine-7-carboxylic acid butylamide |
| 120 | 5-Amino-2-thiazol-2-yl-[1,2,4]triazolo[1,5-a]pyridine-7-carboxylic acid diethylamide |
| 121 | 5-Amino-2-(2-hydroxy-phenyl)-[1,2,4]triazolo[1,5-a]-pyridine-7-carboxylic acid benzyl-isopropyl-amide |
| 122 | 5-Amino-2-thiazol-2-yl-[1,2,4]triazolo[1,5-a]pyridine-7-carboxylic acid diisopropylamide |
| 123 | 5-Amino-2-thiazol-2-yl-[1,2,4]triazolo[1,5-a]pyridine-7-carboxylic acid cyclohexylamide |
| 124 | 5-Amino-2-thiazol-2-yl-[1,2,4]triazolo[1,5-a]pyridine-7-carboxylic acid cyclohexyl-methyl-amide |
| 125 | 5-Amino-2-thiazol-2-yl-[1,2,4]triazolo[1,5-a]pyridine-7-carboxylic acid indan-1-ylamide |
| 126 | 5-Amino-2-thiazol-2-yl-[1,2,4]triazolo[1,5-a]pyridine-7-carboxylic acid (1-phenyl-ethyl)-amide |
| 127 | 5-Amino-2-thiophen-2-yl-[1,2,4]triazolo[1,5-a]pyridine-7-carboxylic acid diethylamide |
| 128 | (5-Amino-2-thiophen-2-yl-[1,2,4]triazolo[1,5-a]pyridin-7-yl)-pyrrolidin-1-yl-methanone |
| 129 | (5-Amino-2-thiophen-2-yl-[1,2,4]triazolo[1,5-a]pyridin-7-yl)-piperidin-1-yl-methanone |
| 130 | 5-Amino-2-thiazol-2-yl-[1,2,4]triazolo[1,5-a]pyridine-7-carboxylic acid 2-methoxy-benzylamide |
| 131 | 5-Amino-2-(5-bromo-furan-2-yl)-[1,2,4]triazolo[1,5-a]-pyridine-7-carboxylic acid butylamide |
| 132 | [5-Amino-2-(5-bromo-furan-2-yl)-[1,2,4]triazolo[1,5-a]-pyridin-7-yl]-morpholin-4-yl-methanone |
| 133 | 5-Amino-2-(5-bromo-furan-2-yl)-[1,2,4]triazolo[1,5-a]-pyridine-7-carboxylic acid 3,4,5-trimethoxy-benzylamide |
| 134 | [5-Amino-2-(1-methyl-1H-pyrrol-2-yl)-[1,2,4]-triazolo[1,5-a]pyridin-7-yl]-pyrrolidin-1-yl-methanone |
| 135 | 5-Amino-2-(1-methyl-1H-pyrrol-2-yl)-[1,2,4]-triazolo[1,5-a]pyridine-7-carboxylic acid benzyl-isopropyl-amide |
| 136 | 5-Amino-2-furan-2-yl-[1,2,4]triazolo[1,5-a]pyridine-7-carboxylic acid benzyl-isopropyl-amide |
| 137 | 5-Amino-2-(5-methyl-furan-2-yl)-[1,2,4]triazolo[1,5-a]-pyridine-7-carboxylic acid butylamide |
| 138 | 5-Amino-2-(5-methyl-furan-2-yl)-[1,2,4]triazolo[1,5-a]-pyridine-7-carboxylic acid cyclohexylamide |
| 139 | [5-Amino-2-(5-methyl-furan-2-yl)-[1,2,4]triazolo[1,5-a]-pyridin-7-yl]-morpholin-4-yl-methanone |
| 140 | 5-Amino-2-(5-methyl-furan-2-yl)-[1,2,4]triazolo[1,5-a]-pyridine-7-carboxylic acid benzyl-methyl-amide |
| 141 | 5-Amino-2-(5-methyl-furan-2-yl)-[1,2,4]triazolo[1,5-a]-pyridine-7-carboxylic acid benzyl-isopropyl-amide |
| 142 | 5-Amino-2-(5-methyl-furan-2-yl)-[1,2,4]triazolo[1,5-a]-pyridine-7-carboxylic acid 3,4-dimethoxy-benzylamide |
| 143 | 5-Amino-2-(3-methyl-thiophen-2-yl)-[1,2,4]triazolo-[1,5-a]pyridine-7-carboxylic acid ethyl-isopropyl-amide |
| 144 | 5-Amino-2-(3-methyl-thiophen-2-yl)-[1,2,4]triazolo-[1,5-a]pyridine-7-carboxylic acid benzyl-isopropyl-amide |
| 145 | 5-Amino-2-phenyl-[1,2,4]triazolo[1,5-a]pyridine-7-carboxylic acid butylamide |
| 146 | 5-Amino-2-phenyl-[1,2,4]triazolo[1,5-a]pyridine-7-carboxylic acid diethylamide |
| 147 | 5-Amino-2-phenyl-[1,2,4]triazolo[1,5-a]pyridine-7-carboxylic acid cyclohexylamide |
| 148 | 5-Amino-2-phenyl-[1,2,4]triazolo[1,5-a]pyridine-7-carboxylic acid cyclohexyl-methyl-amide |
| 149 | 5-Amino-2-phenyl-[1,2,4]triazolo[1,5-a]pyridine-7-carboxylic acid indan-1-ylamide |
| 150 | (5-Amino-2-phenyl-[1,2,4]triazolo[1,5-a]pyridin-7-yl)-pyrrolidin-1-yl-methanone |
| 151 | (5-Amino-2-phenyl-[1,2,4]triazolo[1,5-a]pyridin-7-yl)-piperidin-1-yl-methanone |
| 152 | 5-Amino-2-phenyl-[1,2,4]triazolo[1,5-a]pyridine-7-carboxylic acid benzyl-methyl-amide |
| 153 | 5-Amino-2-furan-3-yl-[1,2,4]triazolo[1,5-a]pyridine-7-carboxylic acid diethylamide |
| 154 | 5-Amino-2-furan-3-yl-[1,2,4]triazolo[1,5-a]pyridine-7-carboxylic acid cyclohexylamide |
| 155 | (5-Amino-2-furan-3-yl-[1,2,4]triazolo[1,5-a]pyridin-7-yl)-piperidin-1-yl-methanone |
| 156 | 5-Amino-2-furan-3-yl-[1,2,4]triazolo[1,5-a]pyridine-7-carboxylic acid 2-chloro-benzylamide |
| 157 | 5-Amino-2-furan-3-yl-[1,2,4]triazolo[1,5-a]pyridine-7-carboxylic acid 2-bromo-benzylamide |
| 158 | 5-Amino-2-(2-hydroxy-phenyl)-[1,2,4]triazolo[1,5-a]-pyridine-7-carboxylic acid butylamide |
| 159 | 5-Amino-2-(2-hydroxy-phenyl)-[1,2,4]triazolo[1,5-a]-pyridine-7-carboxylic acid 2-chloro-benzylamide |
| 160 | 5-Amino-2-(2-hydroxy-phenyl)-[1,2,4]triazolo[1,5-a]-pyridine-7-carboxylic acid 2-bromo-benzylamide |
| 161 | 5-Amino-2-thiophen-2-yl-[1,2,4]triazolo[1,5-a]pyridine-7-carboxylic acid butylamide |
| 162 | 5-Amino-2-thiophen-2-yl-[1,2,4]triazolo[1,5-a]pyridine-7-carboxylic acid cyclohexylamide |
| 163 | 5-Amino-2-thiophen-2-yl-[1,2,4]triazolo[1,5-a]pyridine-7-carboxylic acid 2-chloro-benzylamide |
| 164 | 5-Amino-2-thiophen-2-yl-[1,2,4]triazolo[1,5-a]pyridine-7-carboxylic acid 2-bromo-benzylamide |
| 165 | 5-Amino-2-(5-bromo-furan-2-yl)-[1,2,4]triazolo[1,5-a]-pyridine-7-carboxylic acid cyclohexylamide |
| 166 | 5-Amino-2-(5-bromo-furan-2-yl)-[1,2,4]triazolo[1,5-a]-pyridine-7-carboxylic acid benzylamide |
| 167 | 5-Amino-2-(5-bromo-furan-2-yl)-[1,2,4]triazolo[1,5-a]-pyridine-7-carboxylic acid 2-bromo-benzylamide |

| Example No. | Name |
|---|---|
| 168 | 5-Amino-2-(4-bromo-furan-2-yl)-[1,2,4]triazolo[1,5-a]-pyridine-7-carboxylic acid butylamide |
| 169 | 5-Amino-2-(4-bromo-furan-2-yl)-[1,2,4]triazolo[1,5-a]-pyridine-7-carboxylic acid diethylamide |
| 170 | [5-Amino-2-(4-bromo-furan-2-yl)-[1,2,4]triazolo[1,5-a]-pyridin-7-yl]-pyrrolidin-1-yl-methanone |
| 171 | [5-Amino-2-(4-bromo-furan-2-yl)-[1,2,4]triazolo[1,5-a]-pyridin-7-yl]-piperidin-1-yl-methanone |
| 172 | 5-Amino-2-(4-bromo-furan-2-yl)-[1,2,4]triazolo[1,5-a]-pyridine-7-carboxylic acid benzylamide |
| 173 | 5-Amino-2-(4-bromo-furan-2-yl)-[1,2,4]triazolo[1,5-a]-pyridine-7-carboxylic acid benzyl-isopropyl-amide |
| 174 | 5-Amino-2-(4-bromo-furan-2-yl)-[1,2,4]triazolo[1,5-a]-pyridine-7-carboxylic acid 2-chloro-benzylamide |
| 175 | 5-Amino-2-(4-bromo-furan-2-yl)-[1,2,4]triazolo[1,5-a]-pyridine-7-carboxylic acid 2-bromo-benzylamide |
| 176 | 5-Amino-2-(4-bromo-furan-2-yl)-[1,2,4]triazolo[1,5-a]-pyridine-7-carboxylic acid 4-methoxy-benzylamide |
| 177 | 5-Amino-2-(4-bromo-furan-2-yl)-[1,2,4]triazolo[1,5-a]-pyridine-7-carboxylic acid 3,4,5-trimethoxy-benzylamide |
| 178 | 5-Amino-2-(1-methyl-1H-pyrrol-2-yl)-[1,2,4]triazolo[1,5-a]-pyridine-7-carboxylic acid butylamide |
| 179 | 5-Amino-2-(1-methyl-1H-pyrrol-2-yl)-[1,2,4]triazolo[1,5-a]-pyridine-7-carboxylic acid cyclohexylamide |
| 180 | 5-Amino-2-(1-methyl-1H-pyrrol-2-yl)-[1,2,4]triazolo[1,5-a]-pyridine-7-carboxylic acid benzylamide |
| 181 | 5-Amino-2-(1-methyl-1H-pyrrol-2-yl)-[1,2,4]triazolo[1,5-a]-pyridine-7-carboxylic acid 2-chloro-benzylamide |
| 182 | 5-Amino-2-(1-methyl-1H-pyrrol-2-yl)-[1,2,4]triazolo[1,5-a]-pyridine-7-carboxylic acid 2-bromo-benzylamide |
| 183 | 5-Amino-2-furan-2-yl-[1,2,4]triazolo[1,5-a]pyridine-7-carboxylic acid 4-methoxy-benzylamide |
| 184 | 5-Amino-2-(3-methyl-thiophen-2-yl)-[1,2,4]triazolo[1,5-a]-pyridine-7-carboxylic acid butylamide |
| 185 | 5-Amino-2-(3-methyl-thiophen-2-yl)-[1,2,4]triazolo[1,5-a]-pyridine-7-carboxylic acid diethylamide |
| 186 | 5-Amino-2-(3-methyl-thiophen-2-yl)-[1,2,4]triazolo[1,5-a]-pyridine-7-carboxylic acid diisopropylamide |
| 187 | 5-Amino-2-(3-methyl-thiophen-2-yl)-[1,2,4]triazolo[1,5-a]-pyridine-7-carboxylic acid indan-1-ylamide |
| 188 | [5-Amino-2-(3-methyl-thiophen-2-yl)-[1,2,4]triazolo[1,5-a]-pyridin-7-yl]-pyrrolidin-1-yl-methanone |
| 189 | [5-Amino-2-(3-methyl-thiophen-2-yl)-[1,2,4]triazolo[1,5-a]-pyridin-7-yl]-piperidin-1-yl-methanone |
| 190 | 5-Amino-2-(3-methyl-thiophen-2-yl)-[1,2,4]triazolo[1,5-a]-pyridine-7-carboxylic acid (1-phenyl-ethyl)-amide |
| 191 | 5-Amino-2-(3-methyl-thiophen-2-yl)-[1,2,4]triazolo[1,5-a]-pyridine-7-carboxylic acid 2-chloro-benzylamide |
| 192 | 5-Amino-2-(3-methyl-thiophen-2-yl)-[1,2,4]triazolo[1,5-a]-pyridine-7-carboxylic acid 2-methoxy-benzylamide |
| 193 | 5-Amino-2-(5-methyl-thiophen-2-yl)-[1,2,4]triazolo[1,5-a]-pyridine-7-carboxylic acid butylamide |
| 194 | 5-Amino-2-(5-methyl-thiophen-2-yl)-[1,2,4]triazolo[1,5-a]-pyridine-7-carboxylic acid ethyl-isopropyl-amide |
| 195 | 5-Amino-2-(5-methyl-thiophen-2-yl)-[1,2,4]triazolo[1,5-a]-pyridine-7-carboxylic acid cyclohexylamide |
| 196 | [5-Amino-2-(5-methyl-thiophen-2-yl)-[1,2,4]triazolo[1,5-a]-pyridin-7-yl]-pyrrolidin-1-yl-methanone |
| 197 | 5-Amino-2-(5-methyl-thiophen-2-yl)-[1,2,4]triazolo[1,5-a]-pyridine-7-carboxylic acid benzylamide |
| 198 | 5-Amino-2-(5-methyl-thiophen-2-yl)-[1,2,4]triazolo[1,5-a]-pyridine-7-carboxylic acid (1-phenyl-ethyl)-amide |
| 299 | 5-Amino-2-(5-methyl-thiophen-2-yl)-[1,2,4]triazolo[1,5-a]-pyridine-7-carboxylic acid 2-chloro-benzylamide |
| 200 | 5-Amino-2-(5-methyl-thiophen-2-yl)-[1,2,4]triazolo[1,5-a]-pyridine-7-carboxylic acid 2-bromo-benzylamide |
| 201 | 5-Amino-2-(5-methyl-thiophen-2-yl)-[1,2,4]triazolo[1,5-a]-pyridine-7-carboxylic acid 2-methoxy-benzylamide |
| 202 | 5-Amino-2-(5-methyl-thiophen-2-yl)-[1,2,4]triazolo[1,5-a]-pyridine-7-carboxylic acid 3,4,5-trimethoxy-benzylamide |
| 203 | 5-Amino-2-(5-methyl-thiophen-2-yl)-[1,2,4]triazolo[1,5-a]-pyridine-7-carboxylic acid indan-1-ylamide |
| 204 | 5-Amino-2-thiazol-2-yl-[1,2,4]triazolo[1,5-a]pyridine-7-carboxylic acid benzyl-methyl-amide |
| 205 | 5-Amino-2-thiazol-2-yl-[1,2,4]triazolo[1,5-a]pyridine-7-carboxylic acid 4-chloro-benzylamide |
| 206 | 5-Amino-2-thiazol-2-yl-[1,2,4]triazolo[1,5-a]pyridine-7-carboxylic acid 4-fluoro-benzylamide |
| 207 | 5-Amino-2-thiazol-2-yl-[1,2,4]triazolo[1,5-a]pyridine-7-carboxylic acid 4-methoxy-benzylamide |
| 208 | 5-Amino-2-thiazol-2-yl-[1,2,4]triazolo[1,5-a]pyridine-7-carboxylic acid 3,4-dimethoxy-benzylamide |
| 209 | 5-Amino-2-(5-methyl-furan-2-yl)-[1,2,4]triazolo[1,5-a]-pyridine-7-carboxylic acid indan-1-ylamide |
| 210 | 5-Amino-2-(5-methyl-furan-2-yl)-[1,2,4]triazolo[1,5-a]-pyridine-7-carboxylic acid benzylamide |
| 211 | 5-Amino-2-(5-methyl-furan-2-yl)-[1,2,4]triazolo[1,5-a]-pyridine-7-carboxylic acid (1-phenyl-ethyl)-amide |
| 212 | 5-Amino-2-(5-methyl-furan-2-yl)-[1,2,4]triazolo[1,5-a]-pyridine-7-carboxylic acid 4-chloro-benzylamide |
| 213 | 5-Amino-2-(5-methyl-furan-2-yl)-[1,2,4]triazolo[1,5-a]-pyridine-7-carboxylic acid 4-fluoro-benzylamide |
| 214 | 5-Amino-2-(5-methyl-furan-2-yl)-[1,2,4]triazolo[1,5-a]-pyridine-7-carboxylic acid 2-methoxy-benzylamide |
| 215 | 5-Amino-2-(5-methyl-furan-2-yl)-[1,2,4]triazolo[1,5-a]-pyridine-7-carboxylic acid 4-methoxy-benzylamide |
| 216 | 5-Amino-2-phenyl-[1,2,4]triazolo[1,5-a]-pyridine-7-carboxylic acid benzylamide |
| 217 | 5-Amino-2-phenyl-[1,2,4]triazolo[1,5-a]pyridine-7-carboxylic acid (1-phenyl-ethyl)-amide |
| 218 | 5-Amino-2-phenyl-[1,2,4]triazolo[1,5-a]pyridine-7-carboxylic acid 2-chloro-benzylamide |
| 219 | 5-Amino-2-phenyl-[1,2,4]triazolo[1,5-a]pyridine-7-carboxylic acid 2-bromo-benzylamide |
| 220 | 5-Amino-2-phenyl-[1,2,4]triazolo[1,5-a]pyridine-7-carboxylic acid 2-methoxy-benzylamide |
| 221 | 5-Amino-2-furan-3-yl-[1,2,4]triazolo[1,5-a]-pyridine-7-carboxylic acid ethyl-isopropyl-amide |
| 222 | 5-Amino-2-furan-3-yl-[1,2,4]triazolo[1,5-a]-pyridine-7-carboxylic acid cyclohexyl-methyl-amide |
| 223 | 5-Amino-2-furan-3-yl-[1,2,4]triazolo[1,5-a]-pyridine-7-carboxylic acid indan-1-ylamide |
| 224 | 5-Amino-2-furan-3-yl-[1,2,4]triazolo[1,5-a]-pyridine-7-carboxylic acid benzylamide |
| 225 | 5-Amino-2-furan-3-yl-[1,2,4]triazolo[1,5-a] pyridine-7-carboxylic acid (1-phenyl-ethyl)-amide |
| 226 | 5-Amino-2-furan-3-yl-[1,2,4]triazolo[1,5-a]-pyridine-7-carboxylic acid benzyl-methyl-amide |
| 227 | 5-Amino-2-furan-3-yl-[1,2,4]triazolo[1,5-a]-pyridine-7-carboxylic acid 4-fluoro-benzylamide |
| 228 | 5-Amino-2-furan-3-yl-[1,2,4]triazolo[1,5-a]-pyridine-7-carboxylic acid 2-methoxy-benzylamide |
| 229 | 5-Amino-2-thiophen-2-yl-[1,2,4]triazolo[1,5-a]-pyridine-7-carboxylic acid 4-methoxy-benzylamide |
| 230 | 5-Amino-2-furan-3-yl-[1,2,4]triazolo[1,5-a]-pyridine-7-carboxylic acid 4-chloro-benzylamide |
| 231 | 5-Amino-2-(5-bromo-furan-2-yl)-[1,2,4]triazolo-[1,5-a]pyridine-7-carboxylic acid 4-methoxy-benzylamide |
| 232 | 5-Amino-2-(3-methyl-thiophen-2-yl)-[1,2,4]triazolo-[1,5-a]pyridine-7-carboxylic acid cyclohexylamide |
| 233 | 5-Amino-2-(5-chloro-furan-2-yl)-[1,2,4]triazolo-[1,5-a]pyridine-7-carboxylic acid diethylamide |
| 234 | 5-Amino-2-(5-chloro-furan-2-yl)-[1,2,4]triazolo-[1,5-a]pyridine-7-carboxylic acid cyclohexylamide |
| 235 | [5-Amino-2-(5-chloro-furan-2-yl)-[1,2,4]triazolo-[1,5-a]pyridin-7-yl]-pyrrolidin-1-yl-methanone |
| 236 | [5-Amino-2-(5-chloro-furan-2-yl)-[1,2,4]triazolo-[1,5-a]pyridin-7-yl]-piperidin-1-yl-methanone |
| 237 | [5-Amino-2-(5-chloro-furan-2-yl)-[1,2,4]triazolo-[1,5-a]pyridin-7-yl]-morpholin-4-yl-methanone |
| 238 | 5-Amino-2-(5-chloro-furan-2-yl)-[1,2,4]triazolo-[1,5-a]pyridine-7-carboxylic acid benzylamide |
| 239 | 5-Amino-2-(5-chloro-furan-2-yl)-[1,2,4]triazolo-[1,5-a]pyridine-7-carboxylic acid benzyl-isopropyl-amide |
| 240 | 5-Amino-2-(5-chloro-furan-2-yl)-[1,2,4]triazolo-[1,5-a]pyridine-7-carboxylic acid 2-chloro-benzylamide |
| 241 | 5-Amino-2-(5-chloro-furan-2-yl)-[1,2,4]triazolo-[1,5-a]pyridine-7-carboxylic acid 2-bromo-benzylamide |
| 242 | 5-Amino-2-(5-chloro-furan-2-yl)-[1,2,4]triazolo-[1,5-a]pyridine-7-carboxylic acid cyclohexyl-methyl-amide |

-continued

| Example No. | Name |
|---|---|
| 243 | +5-Amino-2-(5-chloro-furan-2-yl)-[1,2,4]triazolo[1,5-a]-pyridine-7-carboxylic acid cyclohexyl-ethyl-amide |
| 244 | 5-Amino-2-(5-chloro-furan-2-yl)-[1,2,4]triazolo[1,5-a]-pyridine-7-carboxylic acid 4-chloro-benzylamide |
| 245 | 5-Amino-2-(5-chloro-furan-2-yl)-[1,2,4]triazolo[1,5-a]-pyridine-7-carboxylic acid 4-fluoro-benzylamide |
| 246 | 5-Amino-2-(5-chloro-furan-2-yl)-[1,2,4]triazolo[1,5-a]-pyridine-7-carboxylic acid 2-methoxy-benzylamide |
| 247 | 5-Amino-2-(5-chloro-furan-2-yl)-[1,2,4]triazolo[1,5-a]-pyridine-7-carboxylic acid cyclopropylmethyl-methyl-amide |
| 248 | 5-Amino-2-(5-chloro-furan-2-yl)-[1,2,4]triazolo[1,5-a]-pyridine-7-carboxylic acid dimethylamide |
| 249 | [5-Amino-2-(5-chloro-furan-2-yl)-[1,2,4]triazolo[1,5-a]-pyridin-7-yl]-azetidin-1-yl-methanone |
| 250 | 5-Amino-2-(5-chloro-furan-2-yl)-[1,2,4]triazolo[1,5-a]-pyridine-7-carboxylic acid ethyl-methyl-amide |
| 251 | 5-Amino-2-(5-chloro-furan-2-yl)-[1,2,4]triazolo[1,5-a]-pyridine-7-carboxylic acid allyl-methyl-amide |
| 252 | 5-Amino-2-(5-chloro-furan-2-yl)-[1,2,4]triazolo[1,5-a]-pyridine-7-carboxylic acid methyl-propyl-amide |
| 253 | [5-Amino-2-(5-chloro-furan-2-yl)-[1,2,4]triazolo[1,5-a]-pyridin-7-yl]-(3,6-dihydro-2H-pyridin-1-yl-methanone |
| 254 | [5-Amino-2-(5-chloro-furan-2-yl)-[1,2,4]triazolo[1,5-a]-pyridin-7-yl]-(2-methyl-pyrrolidin-1-yl)-methanone |
| 255 | 5-Amino-2-(5-chloro-furan-2-yl)-[1,2,4]triazolo[1,5-a]-pyridine-7-carboxylic acid ethyl-isopropyl-amide |
| 256 | [5-Amino-2-(5-chloro-furan-2-yl)-[1,2,4]triazolo[1,5-a]-pyridin-7-yl]-thiomorpholin-4-yl-methanone |
| 257 | [5-Amino-2-(5-chloro-furan-2-yl)-[1,2,4]triazolo[1,5-a]-pyridin-7-yl]-(2,6-dimethyl-morpholin-4-yl)-methanone |
| 258 | [5-Amino-2-(5-chloro-furan-2-yl)-[1,2,4]triazolo[1,5-a]-pyridin-7-yl]-(2,5-dimethyl-pyrrolidin-1-yl)-methanone |
| 259 | 1-[5-Amino-2-(5-chloro-furan-2-yl)-[1,2,4]triazolo[1,5-a]-pyridine-7-carbonyl]-piperidine-4-carboxylic acid amide |
| 260 | 5-Amino-2-(5-chloro-furan-2-yl)-[1,2,4]triazolo[1,5-a]-pyridine-7-carboxylic acid bis-(2-methoxy-ethyl)-amide |
| 261 | 5-Amino-2-(5-chloro-furan-2-yl)-[1,2,4]triazolo[1,5-a]-pyridine-7-carboxylic acid benzyl-ethyl-amide |
| 262 | 5-Amino-2-(5-chloro-furan-2-yl)-[1,2,4]triazolo[1,5-a]-pyridine-7-carboxylic acid ethyl-pyridin-4-ylmethyl-amide |
| 263 | [5-Amino-2-(5-chloro-furan-2-yl)-[1,2,4]triazolo[1,5-a]-pyridin-7-yl]-(4-phenyl-3,6-dihydro-2H-pyridin-1-yl)-methanone |
| 264 | 5-Amino-2-(5-bromo-furan-2-yl)-[1,2,4]triazolo[1,5-a]-pyridine-7-carboxylic acid ethyl-methyl-amide |
| 265 | [5-Amino-2-(5-bromo-furan-2-yl)-[1,2,4]triazolo[1,5-a]-pyridin-7-yl]-(2,5-dihydro-pyrrol-1-yl)-methanone |
| 266 | 5-Amino-2-(5-bromo-furan-2-yl)-[1,2,4]triazolo[1,5-a]-pyridine-7-carboxylic acid methyl-prop-2-ynyl-amide |
| 267 | 5-Amino-2-(5-bromo-furan-2-yl)-[1,2,4]triazolo[1,5-a]-pyridine-7-carboxylic acid allyl-methyl-amide |
| 268 | 5-Amino-2-(5-bromo-furan-2-yl)-[1,2,4]triazolo[1,5-a]-pyridine-7-carboxylic acid methyl-propyl-amide |
| 269 | 5-Amino-2-(5-bromo-furan-2-yl)-[1,2,4]triazolo[1,5-a]-pyridine-7-carboxylic acid isopropyl-methyl-amide |
| 270 | [5-Amino-2-(5-bromo-furan-2-yl)-[1,2,4]triazolo[1,5-a]-pyridin-7-yl]-(2-methyl-pyrrolidin-1-yl)-methanone |
| 271 | 5-Amino-2-(5-bromo-furan-2-yl)-[1,2,4]triazolo[1,5-a]-pyridine-7-carboxylic acid butyl-methyl-amide |
| 272 | 5-Amino-2-(5-bromo-furan-2-yl)-[1,2,4]triazolo[1,5-a]-pyridine-7-carboxylic acid ethyl-isopropyl-amide |
| 273 | [5-Amino-2-(5-bromo-furan-2-yl)-[1,2,4]triazolo[1,5-a]-pyridin-7-yl]-(2,5-dimethyl-2,5-dihydro-pyrrol-1-yl)-methanone |
| 274 | 5-Amino-2-(5-bromo-furan-2-yl)-[1,2,4]triazolo[1,5-a]-pyridine-7-carboxylic acid diallylamide |
| 275 | [5-Amino-2-(5-bromo-furan-2-yl)-[1,2,4]triazolo[1,5-a]-pyridin-7-yl]-(2,5-dimethyl-pyrrolidin-1-yl)-methanone |
| 276 | 5-Amino-2-(5-bromo-furan-2-yl)-[1,2,4]triazolo[1,5-a]-pyridine-7-carboxylic acid diisopropylamide |
| 277 | 5-Amino-2-(5-bromo-furan-2-yl)-[1,2,4]triazolo[1,5-a]-pyridine-7-carboxylic acid butyl-ethyl-amide |
| 278 | 5-Amino-2-(5-bromo-furan-2-yl)-[1,2,4]triazolo[1,5-a]-pyridine-7-carboxylic acid methyl-pentyl-amide |
| 279 | 5-Amino-2-(5-bromo-furan-2-yl)-[1,2,4]triazolo[1,5-a]-pyridine-7-carboxylic acid (2-dimethylamino-ethyl)-methyl-amide |
| 280 | 5-Amino-2-thiazol-2-yl-[1,2,4]triazolo[1,5-a]-pyridine-7-carboxylic acid ethyl-methyl-amide |
| 281 | (5-Amino-2-thiazol-2-yl-[1,2,4]triazolo[1,5-a]-pyridin-7-yl)-(2,5-dihydro-pyrrol-1-yl)-methanone |
| 282 | 5-Amino-2-thiazol-2-yl-[1,2,4]triazolo[1,5-a]-pyridine-7-carboxylic acid methyl-prop-2-ynyl-amide |
| 283 | 5-Amino-2-thiazol-2-yl-[1,2,4]triazolo[1,5-a]-pyridine-7-carboxylic acid allyl-methyl-amide |
| 284 | 5-Amino-2-thiazol-2-yl-[1,2,4]triazolo[1,5-a]-pyridine-7-carboxylic acid methyl-propyl-amide |
| 285 | 5-Amino-2-thiazol-2-yl-[1,2,4]triazolo[1,5-a]-pyridine-7-carboxylic acid isopropyl-methyl-amide |
| 286 | (5-Amino-2-thiazol-2-yl-[1,2,4]triazolo[1,5-a]-pyridin-7-yl)-(2-methyl-pyrrolidin-1-yl)-methanone |
| 287 | 5-Amino-2-thiazol-2-yl-[1,2,4]triazolo[1,5-a]-pyridine-7-carboxylic acid butyl-methyl-amide |
| 288 | 5-Amino-2-thiazol-2-yl-[1,2,4]triazolo[1,5-a]-pyridine-7-carboxylic acid ethyl-isopropyl-amide |
| 289 | (5-Amino-2-thiazol-2-yl-[1,2,4]triazolo[1,5-a]-pyridin-7-yl)-thiazolidin-3-yl-methanone |
| 290 | 5-Amino-2-thiazol-2-yl-[1,2,4]triazolo[1,5-a]-pyridine-7-carboxylic acid diallylamide |
| 291 | 5-Amino-2-thiazol-2-yl-[1,2,4]triazolo[1,5-a]-pyridine-7-carboxylic acid butyl-ethyl-amide |
| 292 | 5-Amino-2-thiazol-2-yl-[1,2,4]triazolo[1,5-a]-pyridine-7-carboxylic acid methyl-pentyl-amide |
| 293 | 5-Amino-2-(5-bromo-furan-2-yl)-[1,2,4]triazolo[1,5-a]-pyridine-7-carboxylic acid dimethylamide |
| 294 | [5-Amino-2-(5-bromo-furan-2-yl)-[1,2,4]triazolo[1,5-a]-pyridin-7-yl]-(3,6-dihydro-2H-pyridin-1-yl)-methanone |
| 295 | [5-Amino-2-(5-bromo-furan-2-yl)-[1,2,4]triazolo[1,5-a]-pyridin-7-yl]-(3,-methyl-piperidin-1-yl)-methanone |
| 296 | [5-Amino-2-(5-bromo-furan-2-yl)-[1,2,4]triazolo[1,5-a]-pyridin-7-yl]-azepan-1-yl)-methanone |
| 297 | [5-Amino-2-(5-bromo-furan-2-yl)-[1,2,4]triazolo[1,5-a]-pyridin-7-yl]-thiomorpholin-4-yl-methanone |
| 298 | 5-Amino-2-(5-bromo-furan-2-yl)-[1,2,4]triazolo[1,5-a]-pyridine-7-carboxylic acid cyclopropylmethyl-propyl-amide |
| 299 | [5-Amino-2-(5-bromo-furan-2-yl)-[1,2,4]triazolo[1,5-a]-pyridin-7-yl]-(4-ethyl-piperazin-1-yl)-methanone |
| 300 | 1-[5-Amino-2-(5-bromo-furan-2-yl)-[1,2,4]triazolo[1,5-a]-pyridine-7-carbonyl]-piperidine-4-carboxylic acid amide |
| 301 | (5-Amino-2-thiazol-2-yl-[1,2,4]triazolo[1,5-a]-pyridin-7-yl)-2,5-dimethyl-pyrrolidin-1-yl)-methanone |
| 302 | (5-Amino-2-thiazol-2-yl-[1,2,4]triazolo[1,5-a]-pyridin-7-yl)-2,5-dimethyl-2,5-dihydro-pyrrol-1-yl)-methanone |
| 303 | [5-Amino-2-(5-bromo-furan-2-yl)-[1,2,4]triazolo[1,5-a]-pyridin-7-yl]-(2,6-dimethyl-piperidin-1-yl)-methanone |
| 304 | [5-Amino-2-(5-bromo-furan-2-yl)-[1,2,4]triazolo[1,5-a]-pyridin-7-yl]-(2,6-dimethyl-morpholin-4-yl)-methanone |
| 305 | 5-Amino-2-(5-bromo-furan-2-yl)-[1,2,4]triazolo[1,5-a]-pyridine-7-carboxylic acid bis-(2-methoxy-ethyl)-amide |
| 306 | 5-Amino-2-(5-bromo-furan-2-yl)-[1,2,4]triazolo[1,5-a]-pyridine-7-carboxylic acid methyl-phenethyl-amide |
| 307 | 5-Amino-2-(5-bromo-furan-2-yl)-[1,2,4]triazolo[1,5-a]-pyridine-7-carboxylic acid benzyl-ethyl-amide |
| 308 | 5-Amino-2-(5-bromo-furan-2-yl)-[1,2,4]triazolo[1,5-a]-pyridine-7-carboxylic acid methyl-(2-pyridin-2-yl-ethyl)-amide |
| 309 | 5-Amino-2-(5-bromo-furan-2-yl)-[1,2,4]triazolo[1,5-a]-pyridine-7-carboxylic acid (2-diethylamino-ethyl)-ethyl-amide |
| 310 | [5-Amino-2-(5-bromo-furan-2-yl)-[1,2,4]triazolo[1,5-a]-pyridin-7-yl]-(4-benzyl-piperazin-1-yl)-methanone |
| 311 | 5-Amino-2-(5-bromo-furan-2-yl)-[1,2,4]triazolo[1,5-a]-pyridine-7-carboxylic acid bis-(2,2,2-trifluoro-ethyl)-amide |
| 312 | [5-Amino-2-(5-bromo-furan-2-yl)-[1,2,4]triazolo[1,5-a]-pyridin-7-yl]-(4-phenyl-3,6-dihydro-2H-pyridin-1-yl)-methanone |
| 313 | 5-Amino-2-(5-bromo-furan-2-yl)-[1,2,4]triazolo[1,5-a]-pyridine-7-carboxylic acid dibenzylamide |
| 314 | 5-Amino-2-(5-bromo-furan-2-yl)-[1,2,4]triazolo[1,5-a]-pyridine-7-carboxylic acid ethyl-pyridin-4-ylmethyl-amide |

-continued

| Example No. | Name |
|---|---|
| 315 | (5-Amino-2-thiazol-2-yl-[1,2,4]triazolo[1,5-a]-pyridin-7-yl)-(3,6-dihydro-2H-pyridin-1-yl)-methanone |
| 316 | (5-Amino-2-thiazol-2-yl-[1,2,4]triazolo[1,5-a]-pyridin-7-yl)-(3,methyl-piperidin-1-yl)-methanone |
| 317 | (5-Amino-2-thiazol-2-yl-[1,2,4]triazolo[1,5-a]-pyridin-7-yl)-azepan-1-yl-methanone |
| 318 | (5-Amino-2-thiazol-2-yl-[1,2,4]triazolo[1,5-a]-pyridin-7-yl)-thiomorpholin-4-yl-methanone |
| 319 | 5-Amino-2-thiazol-2-yl-[1,2,4]triazolo[1,5-a]-pyridine-7-carboxylic acid cyclopropylmethyl-propyl-amide |
| 320 | 5-Amino-2-thiazol-2-yl-[1,2,4]triazolo[1,5-a]pyridin-7-yl)-(2,6-dimethyl-piperidin-1-yl)-methanone |
| 321 | 5-Amino-2-thiazol-2-yl-[1,2,4]triazolo[1,5-a]-pyridine-7-carboxylic acid bis-(2-methoxy-ethyl)-amide |
| 322 | 5-Amino-2-thiazol-2-yl-[1,2,4]triazolo[1,5-a]-pyridine-7-carboxylic acid methyl-phenethyl-amide |
| 323 | 5-Amino-2-thiazol-2-yl-[1,2,4]triazolo[1,5-a]-pyridine-7-carboxylic acid benzyl-ethyl-amide |
| 324 | 5-Amino-2-thiazol-2-yl-[1,2,4]triazolo[1,5-a]-pyridine-7-carboxylic acid methyl-(2-pyridin-2-yl-ethyl)-amide |
| 325 | 5-Amino-2-thiazol-2-yl-[1,2,4]triazolo[1,5-a]-pyridine-7-carboxylic acid ethyl-pyridin-4-ylmethyl-amide |
| 326 | (5-Amino-2-thiazol-2-yl-[1,2,4]triazolo[1,5-a]-pyridin-7-yl)-(4-phenyl-3,6-dihydro-2H-pyridin-1-yl)-methanone |
| 327 | 5-Amino-2-thiazol-2-yl-[1,2,4]triazolo[1,5-a]-pyridine-7-carboxylic acid dibenzylamide |
| 328 | 5-Amino-2-thiazol-2-yl-[1,2,4]triazolo[1,5-a]-pyridine-7-carboxylic acid ethylamide |
| 329 | (5-Amino-2-thiazol-2-yl-[1,2,4]triazolo[1,5-a]-pyridin-7-yl)-(2-methyl-piperidin-1-yl)-methanone |
| 330 | (5-Amino-2-thiazol-2-yl-[1,2,4]triazolo[1,5-a]-pyridin-7-yl)-(4-methyl-piperidin-1-yl)-methanone |
| 331 | 5-Amino-2-thiazol-2-yl-[1,2,4]triazolo[1,5-a]-pyridine-7-carboxylic acid dipropylamide |
| 332 | (5-Amino-2-thiazol-2-yl-[1,2,4]triazolo[1,5-a]-pyridin-7-yl)-azocan-1-yl-methanone |
| 333 | (5-Amino-2-thiazol-2-yl-[1,2,4]triazolo[1,5-a]-pyridin-7-yl)-(3,5-dimethyl-piperidin-1-yl)-methanone |
| 334 | 5-Amino-2-thiazol-2-yl-[1,2,4]triazolo[1,5-a]-pyridine-7-carboxylic acid butyl-propyl-amide |
| 335 | 5-Amino-2-(5-bromo-furan-2-yl)-[1,2,4]triazolo[1,5-a]-pyridine-7-carboxylic acid ethylamide |
| 336 | [5-Amino-2-(5-bromo-furan-2-yl)-[1,2,4]triazolo[1,5-a]-pyridin-7-yl]-(2-methyl-piperidin-1-yl)-methanone |
| 337 | [5-Amino-2-(5-bromo-furan-2-yl)-[1,2,4]triazolo[1,5-a]-pyridin-7-yl]-(4-methyl-piperidin-1-yl)-methanone |
| 338 | 5-Amino-2-(5-bromo-furan-2-yl)-[1,2,4]triazolo[1,5-a]-pyridine-7-carboxylic acid dipropylamide |
| 339 | [5-Amino-2-(5-bromo-furan-2-yl)-[1,2,4]triazolo[1,5-a]-pyridin-7-yl]-azocan-1-yl-methanone |
| 340 | 5-Amino-2-(5-bromo-furan-2-yl)-[1,2,4]triazolo[1,5-a]-pyridine-7-carboxylic acid cyclohexyl-methyl-amide |
| 341 | [5-Amino-2-(5-bromo-furan-2-yl)-[1,2,4]triazolo[1,5-a]-pyridin-7-yl]-(3,5-dimethyl-piperidin-1-yl)-methanone |
| 342 | 5-Amino-2-(5-bromo-furan-2-yl)-[1,2,4]triazolo[1,5-a]-pyridine-7-carboxylic acid butyl-propyl-amide |
| 343 | 5-Amino-2-(5-bromo-furan-2-yl)-[1,2,4]triazolo[1,5-a]-pyridine-7-carboxylic acid benzyl-methyl-amide |
| 344 | 5-Amino-2-(5-bromo-furan-2-yl)-[1,2,4]triazolo[1,5-a]-pyridine-7-carboxylic acid allyl-cyclopentyl-amide |
| 345 | 5-Amino-2-(5-bromo-furan-2-yl)-[1,2,4]triazolo[1,5-a]-pyridine-7-carboxylic acid cyclohexyl-ethyl-amide |
| 346 | 5-Amino-2-(5-bromo-furan-2-yl)-[1,2,4]triazolo[1,5-a]-pyridine-7-carboxylic acid diisobutylamide |
| 347 | [5-Amino-2-(5-bromo-furan-2-yl)-[1,2,4]triazolo[1,5-a]-pyridin-7-yl]-(3,4-dihydro-1H-isoquinolin-2-yl)-methanone |
| 348 | 5-Amino-2-(5-bromo-furan-2-yl)-[1,2,4]triazolo[1,5-a]-pyridine-7-carboxylic acid allyl-cyclohexyl-amide |
| 349 | [5-Amino-2-(5-bromo-furan-2-yl)-[1,2,4]triazolo[1,5-a]-pyridin-7-yl]-(octoahydro-quinolin-1-yl)-methanone |
| 350 | [5-Amino-2-(5-bromo-furan-2-yl)-[1,2,4]triazolo[1,5-a]-pyridin-7-yl]-(octoahydro-quinolin-2-yl)-methanone |
| 351 | 5-Amino-2-(5-bromo-furan-2-yl)-[1,2,4]triazolo[1,5-a]-pyridine-7-carboxylic acid cyclohexyl-isopropyl-amide |

-continued

| Example No. | Name |
|---|---|
| 352 | 5-Amino-2-(5-bromo-furan-2-yl)-[1,2,4]triazolo[1,5-a]-pyridine-7-carboxylic acid ethyl-(2-pyridin-2-yl-ethyl)-amide |
| 353 | [5-Amino-2-(5-bromo-furan-2-yl)-[1,2,4]triazolo[1,5-a]-pyridin-7-yl]-(4-phenyl-piperazin-1-yl)-methanone |
| 354 | [5-Amino-2-(5-bromo-furan-2-yl)-[1,2,4]triazolo[1,5-a]-pyridin-7-yl]-(3,4,5,6-tetrahydro-2H-[2,3']bipyridinyl-1-yl)-methanone |
| 355 | [5-Amino-2-(5-bromo-furan-2-yl)-[1,2,4]triazolo[1,5-a]-pyridin-7-yl]-(1,3,4,9-tetrahydro-b-carbolin-2-yl)-methanone |
| 356 | 1-[5-Amino-2-(5-bromo-furan-2-yl)-[1,2,4]triazolo[1,5-a]-pyridin-7-carbonyl]-piperidine-3-carboxylic acid diethylamide |
| 357 | (5-Amino-2-thiazol-2-yl-[1,2,4]triazolo[1,5-a]-pyridin-7-yl)-(2,6-dimethyl-piperidin-1-yl)-methanone |
| 358 | (5-Amino-2-thiazol-2-yl-[1,2,4]triazolo[1,5-a]-pyridin-7-yl)-(cis-2,6-dimethyl-piperidin-1-yl)-methanone |
| 359 | [5-Amino-2-(5-bromo-furan-2-yl)-[1,2,4]triazolo[1,5-a]-pyridin-7-yl]-[(2R,5R)-trans-2,5-dimethyl-pyrrolidin-1-yl]-methanone |
| 360 | [5-Amino-2-(5-bromo-furan-2-yl)-[1,2,4]triazolo[1,5-a]-pyridin-7-yl]-(cis-2,6-dimethyl-morpholin-4-yl)-methanone |

EXAMPLE 361

2,6-Diamino-isonicotinamide

A solution of 3.9 g (20 mmol) 2,6-diamino-isonicotinic acid methyl ester in 200 ml methanol was treated for 1 at 0° C. with gaseous ammonia. The mixture was heated for 36 h at 62° C. in an autoclave (4 bar) and afterwards filtered through decalite and evaporated to dryness. 3.5 g (quant.) of the title compound was obtained as a yellow solid.

An analytical sample was further purified through column chromatography on silica eluting with DCM/MeOH/NH$_3$aq. 30:10.1 to yield pure material.

MS m/e (%): 152 (M+H$^+$, 100). 1-H-NMR (400 MHz, DMSO-d$_6$): δ=7.65 (s, br, 1H, CONH$_2$), 7.16 (s, br, 1H, CONH$_2$), 5.93 (s, 2H, Ar—H), 5.50 (s, br, 4H, NH$_2$). Elemental analysis: calc.: C, 47.36, H, 5.30, N, 36.82. found.: C, 46.79, H, 5.33, N, 36.01.

EXAMPLE 362

4-Aminomethyl-pyridine-2,6-diamine

To a refluxing suspension of 0.5 g (3.29 mmol) 2,6-diamino-isonicotinamide in 3 ml THF was added dropwise 0.455 ml (4.8 mmol) boran-dimethylsulfide-complex and the mixture was refluxed for 4 d. After cooling to room temperature 0.548 ml 6N HCl was added and the mixture was neutralized with 2N NaOH. The mixture was concentrated under reduced pressure and the residue was purified by column chromatography on silica eluting with DCM:MeOH:NH$_3$aq. 100:100:1 to yield 166 mg (36%) of the title compound as yellow solid.

MS m/e (%): 139.2 (M+H$^+$, 100). 1-H-NMR (400 MHz, DMSO-d$_6$): δ=5.62 (s, 2H, H3/H5), 5.21 (s, br, 4H, 2×NH$_2$), 3.41 (s, 2H, CH$_2$), 2.00 (s, br, 2H, NH$_2$).

EXAMPLE 363

2-Bromo-N-(2,6-diamino-pyridin-4-ylmethyl)-benzamide

A solution of 172.5 mg (1.25 mmol) 4-aminomethyl-pyridine-2,6-diamine in 5 ml pyridine was treated with 275 mg (1.25 mmol) o-bromobenzoylchloride and a catalytic amount 4-dimethylaminopyridine and stirred for 2.5 h at room temperature. The mixture was evaporated to dryness and the residue was purified by column chromatography on silica eluting with dichloromethane/methanol 9/1 to yield 81 mg (20%) of the title compound.

MS: m/z (%): 321.2 ((M–H)$^+$, 100). 1-H-NMR (400 MHz, DMSO-d$_6$): δ=8.77 (t, J=6 Hz, 1H, NH), 7.66 (d, J=8 Hz, 1H, Ph (3-H)), 7.44 (m, 2H, Ph (4-H, 6-H)), 7.38 (m, 1H, Ph (5-H)), 5.65 (s, 2H, (3-H, 5-H)), 5.31 (s, br, 4H, NH$_2$), 4.13 (d, J=6 Hz, 2H, CH$_2$). Elemental analysis: calc.: C, 48.62, H, 4.08, N, 17.45, Br, 24.88. found.: C, 48.93, H, 4.09, N, 17.18, Br, 24.83.

EXAMPLE 364

Cyclopentanecarboxylic Acid (2,6-Diamino-pyridin-4-ylmethyl)-amide

A solution of 205.6 mg (1.49 mmol) 4-aminomethyl-pyridine-2,6-diamine in 5 ml pyridine was treated with 198 mg (1.49 mmol) cyclopentane carboxylic acid chloride and a catalytic amount 4-dimethylaminopyridine and stirred for 2.5 h at room temperature. The mixture was evaporated to dryness and the residue was purified by column chromatography on silica eluting with dichloromethane/methanol 9/1 to yield 93 mg (26%) of the title compound.

MS: m/z (%): 235.3 ((M–H)$^+$, 100). 1-H-NMR (400 MHz, DMSO-d$_6$): δ=8.09 (t, J=6 Hz, 1H, NH), 5.50 (s, 2H, (3-H, 5-H)), 5.29 (s, br, 4H, NH$_2$), 3.95 (d, J=6 Hz, 2H, CH$_2$), 2.59 (m, 1H, Cyclopentyl (1-H)), 1.75 (m, 2H, Cyclopentyl-H), 1.64 (m, 4H, Cyclopentyl-H), 1.50 (m, 2H, Cyclopentyl-H). Elemental analysis: calc.: C, 61.52, H, 7.74, N, 23.91. found.: C, 61.26, H, 7.74, N, 23.61.

EXAMPLE 365

Cyclopentanecarboxylic Acid [5-Amino-2-(5-bromo-furan-2-yl)-[1,2,4]triazolo[1,5-a]pyridin-7-ylmethyl]-amide To a solution of 39 mg (0.17 mmol) cyclopentanecarboxylic acid (2,6-diamino-pyridin-4-ylmethyl)-amide in 1.4 ml dioxane was added 40.2 mg (0.187 mmol, 1.1 eq.) o-mesitylenesulfonylhydroxylamine and after 2h 38.6 mg (0.221 mmol, 1.3 eq.) 5-bromo-2-furaldehyde. The mixture was heated to 100° C. for 2.5 h and afterwards 0.17 ml 1N KOH in MeOH was added. Opening of the reaction vessel and stirring of the mixture at room temperature for 16 h preceded the evaporation to dryness. The residue was taken up in 4.5 ml water and the aqueous phase was extracted with dichloromethane. The combined organic layers were dried with MgSO$_4$ and evaporated. Purification of the residue with column chromatography on silica eluting with yielded the 12 mg (21%) of the title compound.

MS: m/z (%): [404.3 (96), 406.3 (100), (M–H)$^+$]. 1-H-NMR (400 MHz, DMSO-d$_6$): δ=8.38 (t, J=6 Hz, 1H, NH), 7.15 (d, J=3.6 Hz, 1H, Furanyl (3-H)), 7.07 (s, br, 2H, NH$_2$), 6.81 (d, J=3.6 Hz, 1H, Furanyl (4-H)), 6.72 (s, 1H, 8-H), 6.13 (s, 1H, 6-H), 4.27 (d, J=6 Hz, 2H, CH$_2$), 2.67 (m, 1H, Cyclopentyl (1-H)), 1.80 (m, 2H, Cyclopentyl), 1.65 (m, 4H, Cyclopentyl), 1.54 (m, 2H, Cyclopentyl).

EXAMPLE 366

Cyclopentanecarboxylic Acid [5-Amino-2-(5-methyl-furan-2-yl)-[1,2,4]triazolo[1,5-a]pyridin-7-ylmethyl]-amide The title compound was prepared in accordance with the general method of example 365 from cyclopentanecarboxylic acid (2,6-diamino-pyridin-4-ylmethyl)-amide, o-mesitylene-sulfonylhydroxylamine, and 5-methyl-2-furaldehyde. The purification was performed with column chromatography on silica eluting with dichloromethane/ ethylacetate 1:2.

Yield: 27%. MS: m/z (%): 404 (M+H$^+$, 100). 1-H-NMR (400 MHz, DMSO-d$_6$): δ=8.37 (t, J-6 Hz, 1H, NH), 7.01 (s, br, 2H, NH$_2$), 6.98 (d, J=3 Hz, 1H, Furanyl (3-H)), 6.69 (s, 1H, 8-H), 6.29 (d, J=3 Hz, 1H, Furanyl (4-H)), 6.09 (s, 1H, 6-H), 4.26 (d, J=6 Hz, 2H, CH$_2$), 2.64 (m, 1H, Cyclopentyl (1-H)), 2.38 (s, 3H, CH$_3$), 1.80 (m, 2H, Cyclopentyl), 1.68 (m, 4H, Cyclopentyl), 1.52 (m, 2H, Cyclopentyl).

EXAMPLE 367

N-[5-Amino-2-(5-bromo-furan-2-yl)-[1 2,4]triazolo[1,5-a]pyridin-7-ylmethyl]-2-bromo-benzamide The title compound was prepared in accordance with the general method of example 365 from 2-bromo-N-(2,6-diamino-pyridin-4-ylmethyl)-benzamide, o-mesitylene-sulfonylhydroxylamine, and 5-bromo-2-furaldehyde. The purification was performed with column chromatography on silica eluting with dichloromethane/ethylacetate 1:2.

Yield: 24%. MS: m/z (%): [490.0 (39), 492.0 (100), 494.0 (49), (M–H)$^+$]. 1-H-NMR (400 MHz, DMSO-d$_6$): δ=9.05 (t, J=6 Hz, 1H, NH), 7.69 (d, J=7.6 Hz, 1H, Ph (3-H)), 7.47 (m, 2H, Ph (4-H, 6-H)), 7.39 (m, 1H, Ph (5-H)), 7.16 (d, J=3.6 Hz, 1H, Furanyl (3-H)), 7.12 (s, br, 2H, NH$_2$), 6.89 (s, 1H, 8-H), 6.82 (d, J=3.6 Hz, 1H, Furanyl (4-H)), 6.28 (s, 1H, 6-H), 4.46 (d, J=6 Hz, 2H, CH$_2$).

EXAMPLE 368

N-[5-Amino-2-(5-methyl-furan-2-yl)-[1,2,4]triazolo[1,5-a]pyridin-7-ylmethyl]-2-bromo-benzamide The title compound was prepared in accordance with the general method of example 365 from 2-bromo-N-(2,6-diamino-pyridin-4-ylmethyl)-benzamide, o-mesitylene-sulfonylhydroxylamine, and 5-methyl-2-furaldehyde. The purification was performed with column chromatography on silica eluting with dichloromethane/ethylacetate 1:2.

Yield: 21%. MS m/z (%): [426.3 (100), 428.3 (86), (M–H)$^+$]. 1-H-NMR (400 MHz, DMSO-d$_6$): δ=9.05 (t, J=6 Hz, 1H, NH), 7.68 (m, 1H, Ph), 7.48 (m, 2H, Ph), 7.38 (m, 1H, Ph), 7.05 (s, br, 2H, NH$_2$), 7.00 (d, J=3 Hz, 1H, Furanyl (3-H)), 6.85 (s, 1H, 8-H), 6.30 (d, J=3 Hz, 1H, Furanyl (4-H)), 6.24 (s, 1H, 6-H), 4.46 (d, J=6 Hz, 2H, CH$_2$), 2.38 (s, 3H, CH$_3$).

EXAMPLE 369

2,6-Bis-acetylamino-isonicotinic Acid Methyl Ester

A mixture of 3 g (17.95 mmol) 2,6-diamino-isonicotinic acid methyl ester, 10 ml pyridine and 7.46 ml (78.9 mmol) acetic anhydride was stirred for 1 h at room temperature and subsequently 1 h at 80° C. Volatiles were removed under reduced pressure and the residue was taken up in ethylacetate and Na$_2$CO$_3$ solution. The aqueous pahes was extracted with ethylacetate and the combined organic phases were dried with MgSO$_4$ and concentrated to yield 3.79 g (84%) of the title compound as white crystals.

1-H-NMR (250 MHz, DMSO-d$_6$): δ=8.22 (s, 2H, H3/H5), 3.88 (s, 3H, OCH$_3$), 2.13 (s, 6H, CH$_3$). MS m/z (%): 251.1 (M+H$^+$, 100). Elemental analysis: calculated C, 52.59, H, 5.22, N, 16.73. found C, 52.40, H, 5.17, N, 16.74.

EXAMPLE 370

2,6-Bis-acetylamino-N-methoxy-N-methyl-isonicotinamide

A mixture of 5.33 g (54.7 mmol) N,O,-dimethylhydroxylamine in 40 ml DCM was treated at 0° C. with a 2M solution of trimethylaluminium in toluene and stirred for an additional hour at 0° C. 4.48 g (18.23 mmol) 2,6-bis-acetylamino-N-methoxy-N-methyl-isonicotinamide was added slowly and subsequently 8.65 ml pyridine. The mixture was allowed to stir to room temperature and subsequently for 16 h at room temperature. 10 ml 37% HCL was added and the mixture was poured into 300 ml MeOH. Decalite was added, the mixture was filtered and the filtrate was evaporated to dryness. The residue was further purified by column chromatography on silica eluting with DCM-:MeOH gradient to yield 3.48 g (49%) the title compound.

MS m/z (%): 281.2 (M+H$^+$, 100).

EXAMPLE 371

(2,6-Diamino-pyridin-4-yl)-(4-fluoro-phenyl)-methanone

To a solution of 0.5 g (1.78 mmol) 2,6-bis-acetylamino-N-methoxy-N-methyl-isonicotinamide in 8 ml THF was added at room temperature 7.14 ml (7.14 mmol) of a 1M solution of 4-fluorophenylmagnesium bromide in THF and stirred for 80 min at room temperature and subsequently for 2 h at 40° C. After cooling to room temperature 0.8 ml 37% HCl was added and the mixture was evaporated to dryness. The residue was taken up in ethyl acetate and 2M Na$_2$CO$_3$. The aqueous phase was extracted with ethyl acetate and the combined organic fraction were dried with MgSO$_4$ and evaporated to dryness. The residue was taken up in 3 ml MeOH and 1 ml 37% HCl and heated to reflux for 4 h. After evaporation to dryness the residue was taken up in ethyl acetate and 2M Na$_2$CO$_3$. The aqueous phase was extracted with ethyl acetate and the combined organic fraction were dried with MgSO$_4$ and evaporated to dryness. The title compound was further purified by reversed phase HPLC eluting with an acetonitrile/water gradient and yielded 131 mg (32%) yellow crystals.

1-H-NMR (300 MHz, DMSO-d$_6$): δ=8.13 (s, 1H, H3), 7.83 (m, 2H, phenyl H3/H5) 7.38 (m, 2H, phenyl H2/H6), 5.80 (s, 1H, H5), 5.71 (s, br, 4H, NH$_2$). MS m/z (%): 231.1 (M+H$^+$, 100).

EXAMPLE 372

(2,6-Diamino-Pyridin-4-yl)-phenyl-methanone

The title compound was prepared in accordance with the general method of example 371 from 2,6-bis-acetylamino-N-methoxy-N-methyl-isonicotinamide and phenylmagnesium bromide. The purification was performed by reversed phase HPLC eluting with an acetonitrile/water gradient Yield: 37%.

1-H-NMR (300 MHz, DMSO-d$_6$): δ=8.13 (s, 1H, H3), 7.73 (m, 2H, phenyl H2/H6), 7.64 (m, 1H, phenyl H4), 7.55 (m, 2H, phenyl H3/H5), 5.82 (s, 1H, H5), 5.70 (s, br, 4H, NH$_2$). MS m/z (%): 213.1 (M+H$^+$, 100).

EXAMPLE 373

[5-Amino-2-(5-bromo-furan-2-yl)-[1,2 4]triazolo[1,5-a]pyridin-7-yl]-(4-fluoro-phenyl)-methanone To a solution of 43 mg (0.177 mmol) (2,6-diamino-pyridin-4-yl)-(4-fluoro-phenyl)-methanone in 0.5 ml dioxane at room temperature was added 38.7 mg (0.194 mmol, 1.1 eq.) o-mesitylenesulfonylhydroxylamine and after 1 h 40 mg (0.23 mmol, 1.3 eq.) 5-bromo-2-furaldehyde and stirred for 30 min at 80° C. After the addition of 1N KOH the mixture was stirred at room temperature for 12 h. The mixture was purified by preparative reversed phase HPLC eluting with a gradient of acetonitrile/water to yield 4.5 mg (11%) of the title compound.

EXAMPLE 374

(5-Amino-2-thiazol-2-yl-[1,2,4]triazolo[1,5-a]pyridin-7-yl)-(4-fluoro-phenyl)-methanone The title compound, MS m/e (%): 340 (M+H$^+$, 100), was prepared in accordance with the general method of example 373 from (2,6-diamino-pyridin-4-yl)-(4-fluoro-phenyl)-methanone, o-mesitylene-sulfonylhydroxylamine, and thiazole-2-carbaldehyde. The purification was performed with reversed phase HPLC eluting with an acetonitrile/water gradient.

EXAMPLE 375

(5-Amino-2-pyridin-2-yl-[1,2,4]triazolo[1,5-al]pyridin-7-yl)-(4-fluoro-phenyl)-methanone The title compound, MS m/e (%): 334 (M+H$^+$, 100), was prepared in accordance with the general method of example 373 from (2,6-diamino-pyridin-4-yl)-(4-fluoro-phenyl)-methanone, o-mesitylene-sulfonylhydroxylamine, and pyridine-2-carbaldehyde. The purification was performed with reversed phase HPLC eluting with an acetonitrile/water gradient.

EXAMPLE 376

[5-Amino-2-(5-bromo-furan-2-yl)-[1,2,4]triazolo[1,5-a]pyridin-7-yl]-phenyl-methanone The title compound, MS m/e (%): 383 (M+H$^+$, 100), was prepared in accordance with the general method of example 373 from (2,6-diamino-pyridin-4-yl)-phenyl-methanone, o-mesitylene-sulfonylhydroxylamine, and 5-bromo-2-furaldehyde. The purification was performed with reversed phase HPLC eluting with an acetonitrile/water gradient.

EXAMPLE 377

(5-Amino-2-thiazol-2-yl-[1,2,4]triazolo[1,5-a]pyridin-7-yl)-phenyl-methanone The title compound, MS m/e (%): 322 (M+H$^+$, 100), was prepared in accordance with the general method of example 373 from (2,6-diamino-pyridin-4-yl)-phenyl-methanone, o-mesitylene-sulfonylhydroxylamine, and thiazole-2-carbaldehyde. The purification was performed with reversed phase HPLC eluting with an acetonitrile/water gradient.

EXAMPLE 378

(5-Amino-2-pyridin-2-yl-[1,2,4]triazolo[1,5-a]pyridin-7-yl)-phenyl-methanone The title compound, MS m/e (%): 316 (M+H$^+$, 100), was prepared in accordance with the general method of example 373 from (2,6-diamino-pyridin-4-yl)-phenyl-methanone, o-mesitylene-sulfonylhydroxylamine, and pyridine-2-carbaldehyde. The purification was performed with reversed phase HPLC eluting with an acetonitrile/water gradient.

According to example 20 the following triazolopyridine carboxamide derivatives have been synthesised. The results, including receptor affinity values, calculated receptor selectivity ratios, structural formulae and characterization as described above are compiled in the following list comprising example 379 to example 435.

| No. | Ki hA2A (nM) | Ki hA1 (nM) | selectivity (A1/A2a) | Structure | MW | MS m/e (%) |
|---|---|---|---|---|---|---|
| 379 | 33.5 | 576.9 | 17.2 | 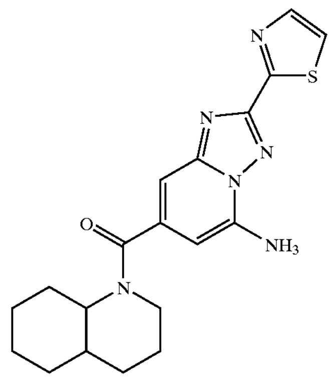 | 382.5 | MH+ (100) |
| 380 | 76.9 | 1908.6 | 24.8 | 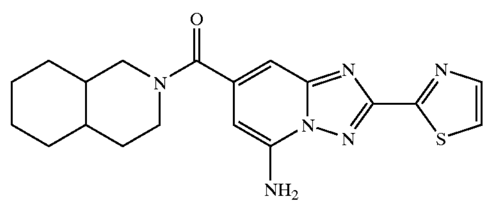 | 382.5 | MH+ (100) |
| 381 | 179.7 | 2048.3 | 11.4 | 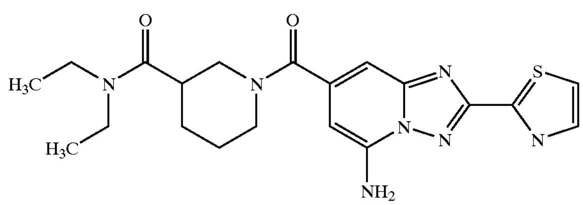 | 427.5 | MH+ (100) |
| 382 | 54.6 | 729.3 | 13.4 | 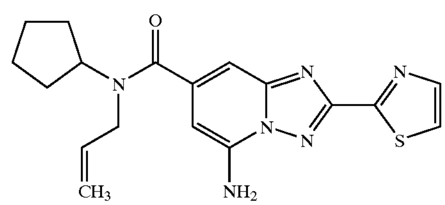 | 368.5 | MH+ (100) |
| 383 | 81.2 | 1126.6 | 13.9 | 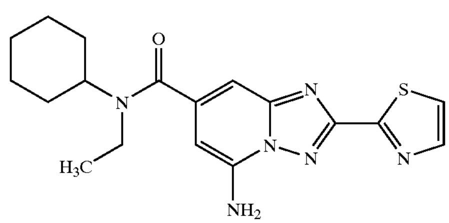 | 370.5 | MH+ (100) |
| 384 | 3.2 | 710.7 | 222.1 | 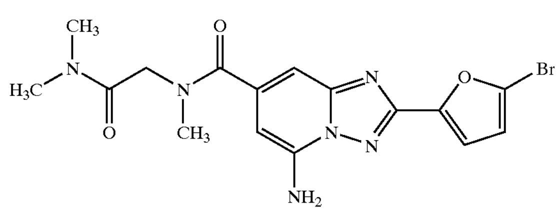 | 421.3 | MH+ (100) |

-continued

| No. | Ki hA2A (nM) | Ki hA1 (nM) | selectivity (A1/A2a) | Structure | MW | MS m/e (%) |
|---|---|---|---|---|---|---|
| 385 | 11.7 | 615.7 | 52.6 | (5-bromofuran-2-yl)-[1,2,4]triazolo[1,5-a]pyridine with 5-NH2, 7-carbonyl-(2-methoxymethyl)pyrrolidine, Chiral | 420.3 | MH+ (100) |
| 386 | 2.4 | 292.3 | 121.8 | (5-bromofuran-2-yl)-[1,2,4]triazolo[1,5-a]pyridine with 5-NH2, 7-carbonyl-(2-methoxymethyl)pyrrolidine, Chiral (opposite enantiomer) | 420.3 | MH+ (100) |
| 387 | 118.2 | 2535.5 | 21.5 | (5-bromofuran-2-yl)-[1,2,4]triazolo[1,5-a]pyridine with 5-NH2, 7-carbonyl-(2,5-bis(methoxymethyl))pyrrolidine, Chiral | 464.3 | MH+ (100) |
| 388 | 26.7 | 330.5 | 12.4 | (5-bromofuran-2-yl)-[1,2,4]triazolo[1,5-a]pyridine with 5-NH2, 7-carbonyl-prolinamide, Chiral | 419.2 | MH+ (100) |
| 389 | 9.8 | 383.3 | 39.1 | (5-bromofuran-2-yl)-[1,2,4]triazolo[1,5-a]pyridine with 5-NH2, 7-carbonyl-prolinamide, Chiral (opposite enantiomer) | 419.2 | MH+ (100) |

-continued
| No. | Ki hA2A (nM) | Ki hA1 (nM) | selectivity (A1/A2a) | Structure | MW | MS m/e (%) |
|---|---|---|---|---|---|---|
| 390 | 8.3 | 813.1 | 98 | 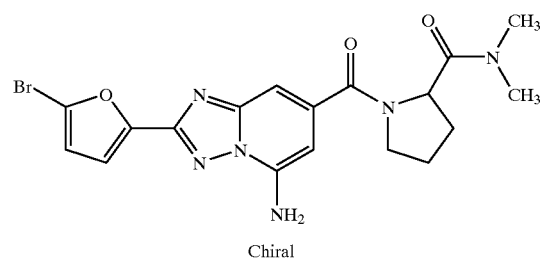 Chiral | 447.3 | MH+ (100) |
| 391 | 53 | 1464.8 | 27.6 | 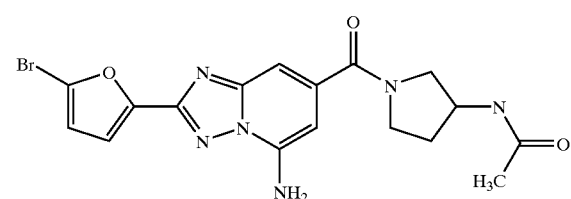 | 433.3 | MH+ (100) |
| 392 | 34.7 | 1775.2 | 51.2 | 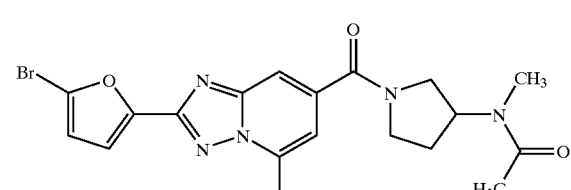 | 447.3 | MH+ (100) |
| 393 | 2.9 | 95.3 | 32.9 | 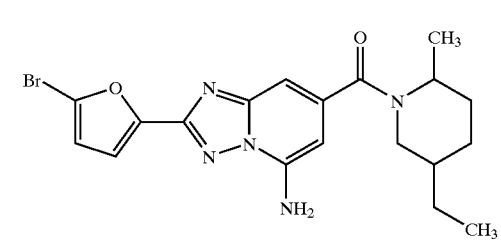 | 432.3 | MH+ (100) |
| 394 | 11 | 417.1 | 37.9 | 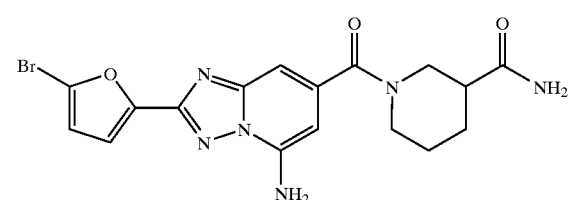 | 433.3 | MH+ (100) |
| 395 | 6.7 | 295.1 | 44 | 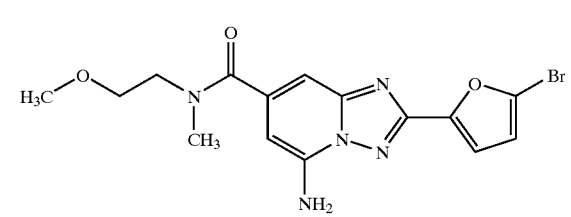 | 394.2 | MH+ (100) |
| 396 | 3.5 | 170.4 | 48.7 | 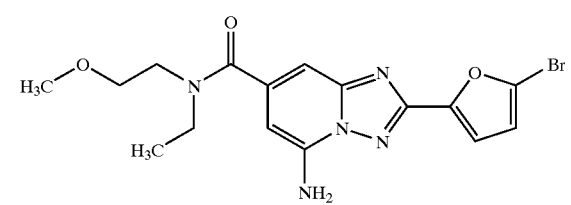 | 408.3 | MH+ (100) |

-continued

| No. | Ki hA2A (nM) | Ki hA1 (nM) | selectivity (A1/A2a) | Structure | MW | MS m/e (%) |
|---|---|---|---|---|---|---|
| 397 | 298.4 | 5490 | 18.4 | 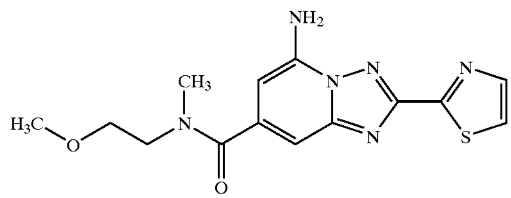 | 332.4 | MH+ (100) |
| 498 | 189.8 | 3991 | 21 | 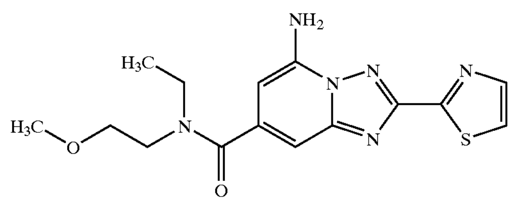 | 346.4 | MH+ (100) |
| 399 | 101.1 | 6206.9 | 61.4 | 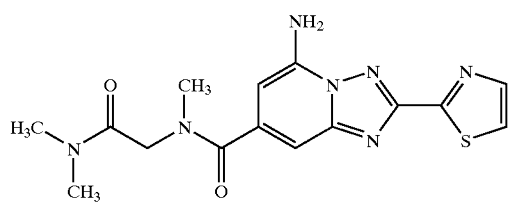 | 359.4 | MH+ (100) |
| 400 | 83.7 | 4462.8 | 53.3 | Chiral | 358.4 | MH+ (100) |
| 401 | 51.9 | 3444.8 | 66.4 | Chiral | 358.4 | MH+ (100) |
| 402 | 292.6 | 6206.9 | 21.2 | Chiral | 385.5 | MH+ (100) |

-continued

| No. | Ki hA2A (nM) | Ki hA1 (nM) | selectivity (A1/A2a) | Structure | MW | MS m/e (%) |
|---|---|---|---|---|---|---|
| 403 | 397.7 | 6206.9 | 15.6 | 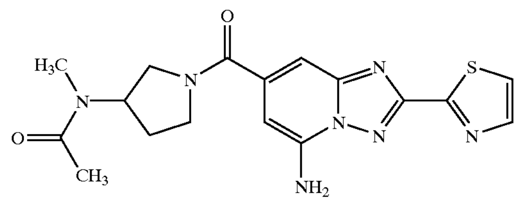 | 385.5 | MH+ (100) |
| 404 | 94.3 | 1253.8 | 13.3 | 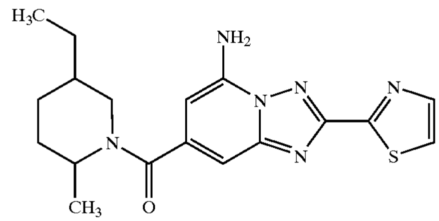 | 370.5 | MH+ (100) |
| 405 | 43.3 | 1002.4 | 23.2 | 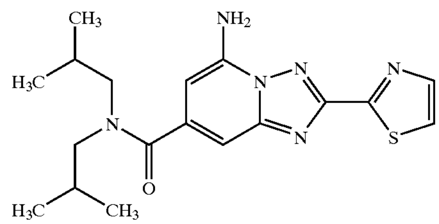 | 372.5 | MH+ (100) |
| 406 | 146.8 | 3929 | 26.8 | 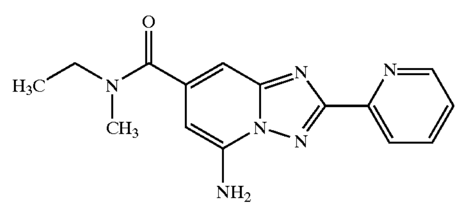 | 296.3 | MH+ (100) |
| 407 | 69.1 | 1827.9 | 26.5 | 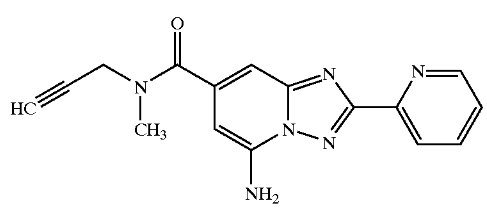 | 306.3 | MH+ (100) |
| 408 | 91.8 | 1368.6 | 14.9 | 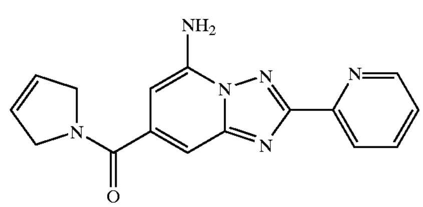 | 306.3 | MH+ (100) |
| 409 | 99.8 | 1651 | 16.5 | 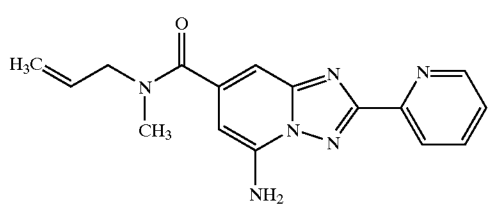 | 308.3 | MH+ (100) |

-continued

| No. | Ki hA2A (nM) | Ki hA1 (nM) | selectivity (A1/A2a) | Structure | MW | MS m/e (%) |
|---|---|---|---|---|---|---|
| 410 | 56.8 | 1449.3 | 25.5 | 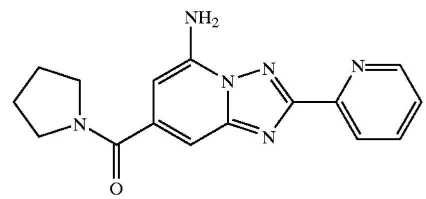 | 308.3 | MH+ (100) |
| 411 | 62.3 | 1405.9 | 22.6 | 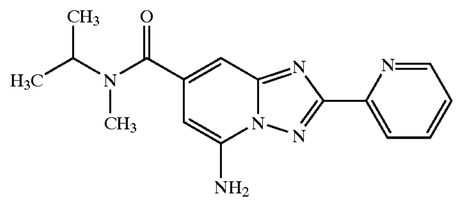 | 310.4 | MH+ (100) |
| 412 | 118.7 | 3019.7 | 25.4 | 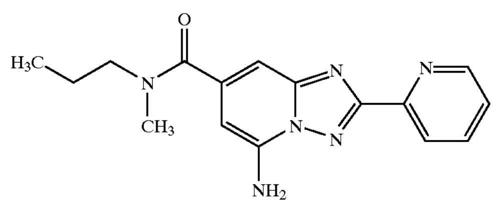 | 310.4 | MH+ (100) |
| 413 | 37.8 | 1427.6 | 37.8 | 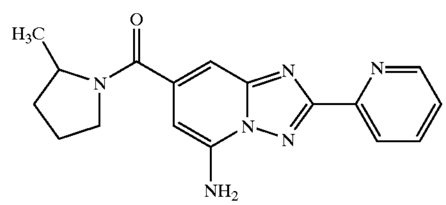 | 322.4 | MH+ (100) |
| 414 | 56 | 884.5 | 15.8 | 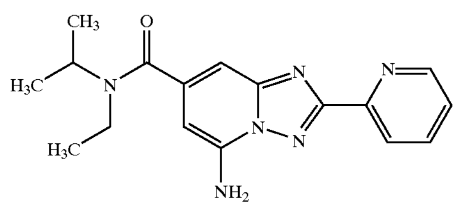 | 324.4 | MH+ (100) |
| 415 | 75.4 | 274 | 3.6 | 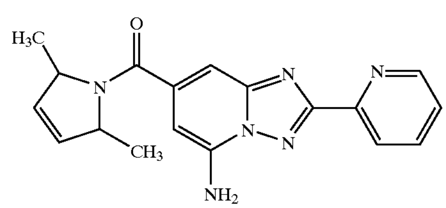 | 334.4 | MH+ (100) |
| 416 | 48.1 | 834.8 | 17.4 | 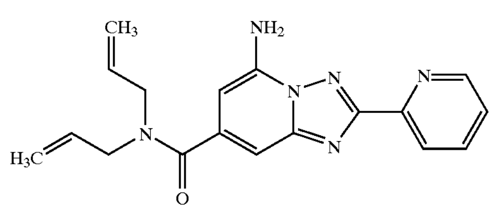 | 334.4 | MH+ (100) |

-continued

| No. | Ki hA2A (nM) | Ki hA1 (nM) | selectivity (A1/A2a) | Structure | MW | MS m/e (%) |
|---|---|---|---|---|---|---|
| 417 | 16.9 | 532.2 | 31.5 | 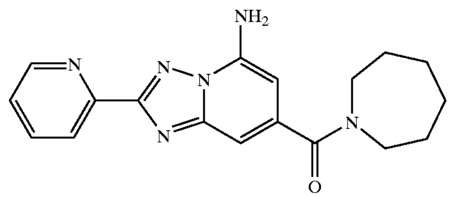 | 336.4 | MH+ (100) |
| 418 | 42.4 | 1024.1 | 24.2 | 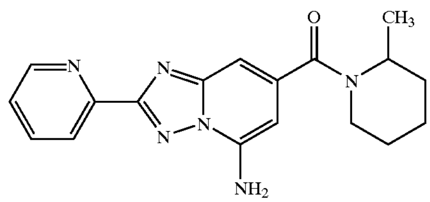 | 336.4 | MH+ (100) |
| 419 | 44.9 | 1595.2 | 35.5 | 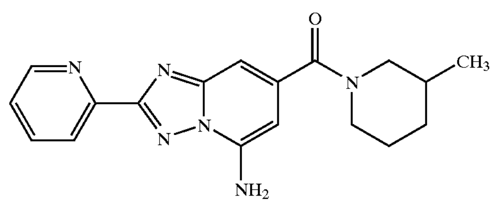 | 336.4 | MH+ (100) |
| 420 | 103.3 | 1812.4 | 17.5 | 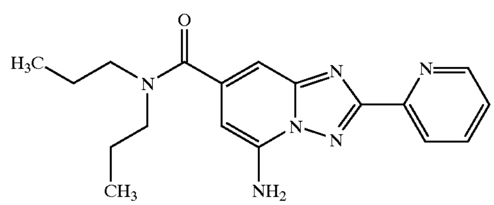 | 338.4 | MH+ (100) |
| 421 | 85.7 | 1362.4 | 15.9 | 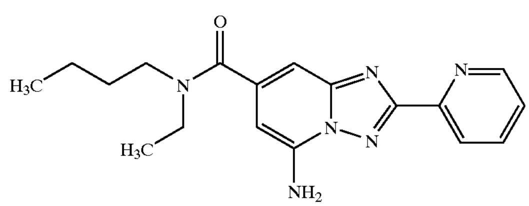 | 338.4 | MH+ (100) |
| 422 | 17.4 | 372.4 | 21.4 | 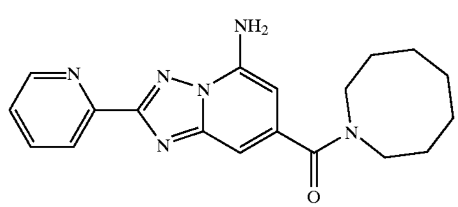 | 350.4 | MH+ (100) |
| 423 | 33.8 | 831.7 | 24.6 | 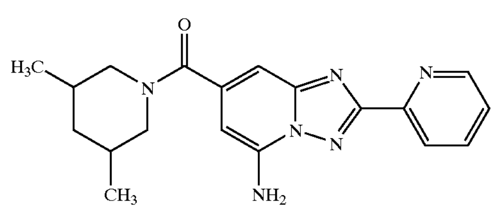 | 350.4 | MH+ (100) |

-continued

| No. | Ki hA2A (nM) | Ki hA1 (nM) | selectivity (A1/A2a) | Structure | MW | MS m/e (%) |
|---|---|---|---|---|---|---|
| 424 | 49.6 | 878.3 | 17.7 | 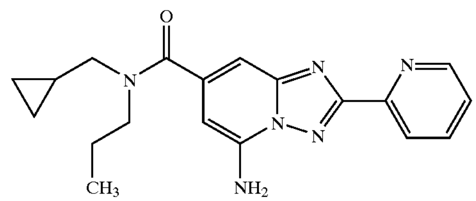 | 350.4 | MH+ (100) |
| 425 | 40.8 | 1294.1 | 31.7 | Chiral | 352.4 | MH+ (100) |
| 426 | 119.4 | 2051.4 | 17.2 | Chiral | 352.4 | MH+ (100) |
| 427 | 101.8 | 1191.7 | 11.7 | 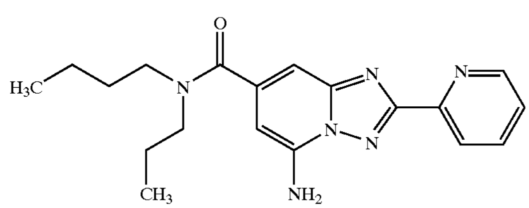 | 352.4 | MH+ (100) |
| 428 | 116.9 | 6206.9 | 53.1 | 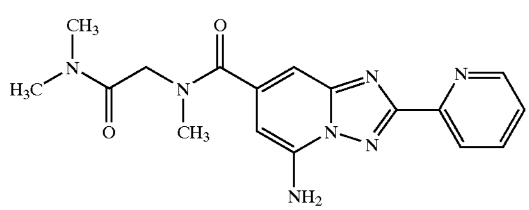 | 353.4 | MH+ (100) |
| 429 | 31 | 473.9 | 15.3 | 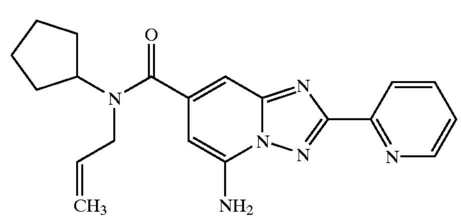 | 362.4 | MH+ (100) |

-continued

| No. | Ki hA2A (nM) | Ki hA1 (nM) | selectivity (A1/A2a) | Structure | MW | MS m/e (%) |
|---|---|---|---|---|---|---|
| 430 | 63.6 | 689 | 10.8 | 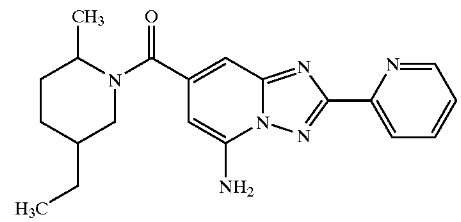 | 364.5 | MH+ (100) |
| 431 | 33.1 | 1033.4 | 31.2 | 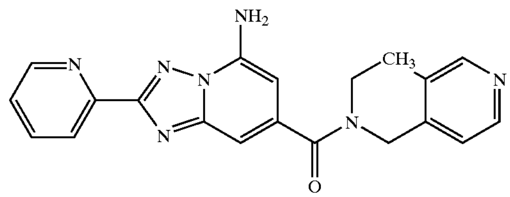 | 373.4 | MH+ (100) |
| 432 | 88 | 2395.9 | 27.2 | Chiral | 379.4 | MH+ (100) |
| 433 | 15.6 | 184.7 | 11.8 | 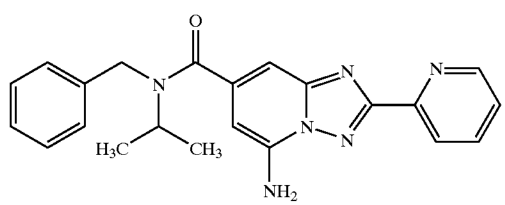 | 386.5 | MH+ (100) |
| 434 | 117.9 | 6206.9 | 52.6 | 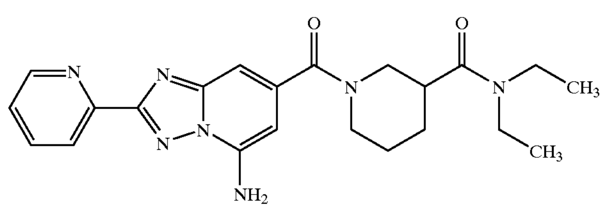 | 421.5 | MH+ (100) |
| 435 | 6.4 | 121.3 | 19 | 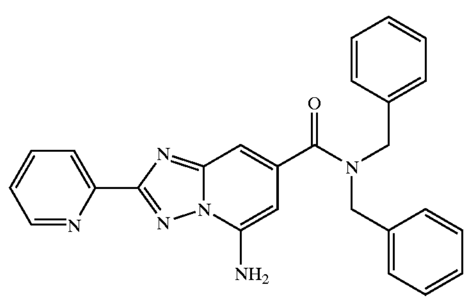 | 434.5 | MH+ (100) |

Names for representative compounds, Examples 379 to 435, are given in the table below.

| Example No. | Name |
|---|---|
| 379 | (5-Amino-2-thiazol-2-yl-[1,2,4]triazolo[1,5-a]pyridin-7-yl)-(octahydro-quinolin-1-yl)-methanone |
| 380 | (5-Amino-2-thiazol-2-yl-[1,2,4]triazolo[1,5-a]pyridin-7-yl)-(octahydro-isoquinolin-2-yl)-methanone |
| 381 | 1-(5-Amino-2-thiazol-2-yl-[1,2,4]triazolo[1,5-a]pyridine-7-carbonyl)-piperidine-3-carboxylic acid diethylamide |
| 382 | 5-Amino-2-thiazol-2-yl-[1,2,4]triazolo[1,5-a]pyridine-7-carboxylic acid allyl-cyclopentyl-amide |
| 383 | 5-Amino-2-thiazol-2-yl-[1,2,4]triazolo[1,5-a]pyridine-7-carboxylic acid cyclohexyl-ethyl-amide |
| 384 | 5-Amino-2-(5-bromo-furan-2-yl)-[1,2,4]triazolo[1,5-a]pyridine-7-carboxylic acid dimethylcarbamoylmethyl-methyl-amide |
| 385 | [5-Amino-2-(5-bromo-furan-2-yl)-[1,2,4]triazolo[1,5-a]pyridin-7-yl]-(S-2-methoxymethyl-pyrrolidin-1-yl)-methanone |
| 386 | [5-Amino-2-(5-bromo-furan-2-yl)-[1,2,4]triazolo[1,5-a]pyridin-7-yl]-(R-2-methoxymethyl-pyrrolidin-1-yl)-methanone |
| 387 | [5-Amino-2-(5-bromo-furan-2-yl)-[1,2,4]triazolo[1,5-a]pyridin-7-yl]-(S,S-2,5-bis-methoxymethyl-pyrrolidin-1-yl)-methanone |
| 388 | 1-[5-Amino-2-(5-bromo-furan-2-yl)-[1,2,4]triazolo[1,5-a]pyridine-7-carbonyl]-L-pyrrolidine-2-carboxylic acid amide |
| 389 | 1-[5-Amino-2-(5-bromo-furan-2-yl)-[1,2,4]triazolo[1,5-a]pyridine-7-carbonyl]-D-pyrrolidine-2-carboxylic acid amide |
| 390 | 1-[5-Amino-2-(5-bromo-furan-2-yl)-[1,2,4]triazolo[1,5-a]pyridine-7-carbonyl]-pyrrolidine-2-carboxylic acid dimethylamide |
| 391 | N-{1-[5-Amino-2-(5-bromo-furan-2-yl)-[1,2,4]triazolo[1,5-a]pyridine-7-carbonyl]-pyrrolidin-3-yl}-acetamide |
| 392 | N-{1-[5-Amino-2-(5-bromo-furan-2-yl)-[1,2,4]triazolo[1,5-a]pyridine-7-carbonyl]-pyrrolidin-3-yl}-N-methyl-acetamide |
| 393 | [5-Amino-2-(5-bromo-furan-2-yl)-[1,2,4]triazolo[1,5-a]pyridin-7-yl]-(5-ethyl-2-methyl-piperidin-1-yl)-methanone |
| 394 | 1-[5-Amino-2-(5-bromo-furan-2-yl)-[1,2,4]triazolo[1,5-a]pyridine-7-carbonyl]-piperidine-3-carboxylic acid amide |
| 395 | 5-Amino-2-(5-bromo-furan-2-yl)-[1,2,4]triazolo[1,5-a]pyridine-7-carboxylic acid (2-methoxy-ethyl)-methyl-amide |
| 396 | 5-Amino-2-(5-bromo-furan-2-yl)-[1,2,4]triazolo[1,5-a]pyridine-7-carboxylic acid ethyl-(2-methoxy-ethyl)-amide |
| 397 | 5-Amino-2-thiazol-2-yl-[1,2,4]triazolo[1,5-a]pyridine-7-carboxylic acid (2-methoxy-ethyl)-methyl-amide |
| 398 | 5-Amino-2-thiazol-2-yl-[1,2,4]triazolo[1,5-a]pyridine-7-carboxylic acid ethyl-(2-methoxy-ethyl)-amide |
| 399 | 5-Amino-2-thiazol-2-yl-[1,2,4]triazolo[1,5-a]pyridine-7-carboxylic acid dimethylcarbamoylmethyl-methyl-amide |
| 400 | (5-Amino-2-thiazol-2-yl-[1,2,4]triazolo[1,5-a]pyridin-7-yl)-(S-2-methoxymethyl-pyrrolidin-1-yl)-methanone |
| 401 | (5-Amino-2-thiazol-2-yl-[1,2,4]triazolo[1,5-a]pyridin-7-yl)-(R-2-methoxymethyl-pyrrolidin-1-yl)-methanone |
| 402 | 1-(5-Amino-2-thiazol-2-yl-[1,2,4]triazolo[1,5-a]pyridine-7-carbonyl)-pyrrolidine-2-carboxylic acid dimethylamide |
| 403 | N-[1-(5-Amino-2-thiazol-2-yl-[1,2,4]triazolo[1,5-a]pyridine-7-carbonyl)-pyrrolidin-3-yl]-N-methyl-acetamide |
| 404 | (5-Amino-2-thiazol-2-yl-[1,2,4]triazolo[1,5-a]pyridin-7-yl)-(5-ethyl-2-methyl-piperidin-1-yl)-methanone |
| 405 | 5-Amino-2-thiazol-2-yl-[1,2,4]triazolo[1,5-a]pyridine-7-carboxylic acid diisobutylamide |
| 406 | 5-Amino-2-pyridin-2-yl-[1,2,4]triazolo[1,5-a]pyridine-7-carboxylic acid ethyl-methyl-amide[5-amino-2-(5-bromo-furan-2-yl)-[1,2,4 |
| 407 | 5-Amino-2-pyridine-2-yl-[1,2,4]triazolo[1,5-a]pyridine-7-carboxylic acid methyl-prop-2-ynyl-amide |
| 408 | (5-Amino-2-pyridin-2-yl-[1,2,4]triazolo[1,5-a]pyridin-7-yl)-(2,5-dihydro-pyrrol-1-yl)-methanone |
| 409 | 5-Amino-2-pyridin-2-yl-[1,2,4]triazolo[1,5-a]pyridine-7-carboxylic acid allyl-methyl-amide |
| 410 | (5-Amino-2-pyridin-2-yl-[1,2,4]triazolo[1,5-a]pyridin-7-yl)-pyrrolidin-1-yl-methanone |
| 411 | 5-Amino-2-pyridin-2-yl-[1,2,4]triazolo[1,5-a]pyridine-7-carboxylic acid isopropyl-methyl-amide |
| 412 | 5-Amino-2-pyridin-2-yl-[1,2,4]triazolo[1,5-a]pyridine-7-carboxylic acid methyl-propyl-amide |
| 413 | (5-Amino-2-pyridin-2-yl-[1,2,4]triazolo[1,5-a]pyridin-7-yl)-(2-methyl-pyrrolidin-1-yl)-methanone |
| 414 | 5-Amino-2-pyridin-2-yl-[1,2,4]triazolo[1,5-a]pyridine-7-carboxylic acid ethyl-isopropyl-amide |
| 415 | (5-Amino-2-pyridin-2-yl-[1,2,4]triazolo[1,5-a]pyridin-7-yl)-(2,5-dimethyl-2,5-dihydro-pyrrol-1-yl)-methanone |
| 416 | 5-Amino-2-pyridin-2-yl-[1,2,4]triazolo[1,5-a]pyridine-7-carboxylic acid diallylamide |
| 417 | (5-Amino-2-pyridin-2-yl-[1,2,4]triazolo[1,5-a]pyridin-7-yl)-azepan-1-yl-methanone |
| 418 | (5-amino-2-pyridin-2-yl-[1,2,4]triazolo[1,5-a]pyridin-7-yl)-(2-methyl-piperidin-1-yl)-methanone |
| 419 | (5-Amino-2-pyridin-2-yl-[1,2,4]triazolo[1,5-a]pyridin-7-yl)-(3-methyl-piperidin-1-yl)-methanone |
| 420 | 5-Amino-2-pyridin-2-yl-[1,2,4]triazolo[1,5-a]pyridine-7-carboxylic acid dipropylamide |
| 421 | 5-Amino-2-pyridin-2-yl-[1,2,4]triazolo[1,5-a]pyridine-7-carboxylic acid butyl-ethyl-amide |
| 422 | (5-Amino-2-pyridin-2-yl-[1,2,4]triazolo[1,5-a]pyridin-7-yl)-azocan-1-yl-methanone |
| 423 | (5-Amino-2-pyridin-2-yl-[1,2,4]triazolo[1,5-a]pyridin-7-yl)-(3,5-dimethyl-piperidin-1-yl)-methanone |
| 424 | 5-Amino-2-pyridin-2-yl-[1,2,4]triazolo[1,5-a]pyridine-7-carboxylic acid cyclopropylmethyl-propyl-amide |
| 425 | (5-Amino-2-pyridin-2-yl-[1,2,4]triazolo[1,5-a]pyridin-7-yl)-(R-2-methoxymethyl-pyrrolidin-1-yl)-methanone |
| 426 | (5-Amino-2-pyridin-2-yl-[1,2,4]triazolo[1,5-a]pyridin-7-yl)-(S-2-methoxymethyl-pyrrolidin-1-yl)-methanone |
| 427 | 5-Amino-2-pyridin-2-yl-[1,2,4]triazolo[1,5-a]pyridine-7-carboxylic acid butyl-propyl-amide |
| 428 | 5-Amino-2-pyridin-2-yl-[1,2,4]triazolo[1,5-a]pyridine-7-carboxylic acid dimethylcarbamoylmethyl-methyl-amide |
| 429 | 5-Amino-2-pyridin-2-yl-[1,2,4]triazolo[1,5-a]pyridine-7-carboxylic acid allyl-cyclopentyl-amide |
| 430 | (5-Amino-2-pyridin-2-yl-[1,2,4]triazolo[1,5-a]pyridin-7-yl)-(5-ethyl-2-methyl-piperidin-1-yl)-methanone |
| 431 | 5-Amino-2-pyridin-2-yl-[1,2,4]triazolo[1,5-a]pyridine-7-carboxylic acid ethyl-pyridin-4-ylmethyl-amide |
| 432 | 1-(5-Amino-2-pyridin-2-yl-[1,2,4]triazolo[1,5-a]pyridine-7-carbonyl)-pyrrolidine-2-carboxylic acid dimethyl amide |
| 433 | 5-Amino-2-pyridin-2-yl-[1,2,4]triazolo[1,5-a]pyridine-7-carboxylic acid benzyl-isopropyl-amide |
| 434 | 1-(5-Amino-2-pyridin-2-yl-[1,2,4]triazolo[1,5-a]pyridine-7-carbonyl)-piperidine-3-carboxylic acid diethylamide |
| 435 | 5-Amino-2-pyridin-2-yl-[1,2,4]triazolo[1,5-a]pyridine-7-carboxylic acid dibenzylamide |

What is claimed is:
1. A compound of the formula

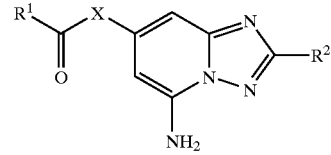

I wherein
R¹ is unsubstituted lower alkoxy, cycloalkyl or aryl, or lower alkoxy, cycloalkyl or aryl substituted by halogen or lower alkoxy, or is —NR'R", wherein R' and R" are, independently selected from, hydrogen, lower alkyl, lower alkenyl, lower alkynyl, unsubstituted —$(CR_2)_n$-aryl, or —$(CR_2)_n$-aryl substituted by one to three substituents, selected from the group, consisting of halogen or lower alkoxy, or are —$(CH_2)_{n+1}NR^a{}_2$, —$(CH_2)_n$-pyridinyl, —$(CH_2)_n$-indanyl, —$(CH_2)_n$-cycloalkyl, —$(CH_2)_n$—O-lower alkyl, —$(CH_2)_n$—C(O)—$NR^b{}_2$, —$(CH_2)_n$—$CF_3$, or R' and R" are together with the N atom to which they are attached form unsubstituted pyrrolidin-1-yl, piperidin-1-yl, 3,4- dihydro-1H-isoquinolin-2-yl, morpholinyl, azatidin-1-yl, 3,6-dihydro-2H-pyridin-1-yl, thiomorpholinyl, 2,5-dihydro-pyrrol-1-yl, thiazolidin-3-yl, piperazinyl, azocan-1-yl, azepan-1-yl, octahydroquinolin-1-yl, octahydroquinolin-2-yl, 1,3,4,9-tetrahydro-b-carbolin-2-yl, or pyrrolidin-1-yl, piperidin-1-yl, 3,4-dihydro-1H-isoquinolin-2-yl, morpholinyl, azatidin-1-yl, 3,6-dihydro-2H-pyridin-1-yl, thiomorpholinyl, 2,5-dihydro-pyrrol-1-yl, thiazolidin-3-yl, piperazinyl, azocan-1-yl, azepan-1-yl, octahydroquinolin-1-yl, octahydroquinolin-2-yl, 1,3,4,9-tetrahydro-b-carbolin-2-yl substituted by one to three substituents, selected from the group consisting of lower alkyl, phenyl, benzyl, pyridyl, —C(O)—NR$^c_2$, —(CH$_2$)$_n$—O-lower alkyl or —NR$^d$—(C(O)-lower alkyl;

$R_2$ is unsubstituted aryl or a 5 or 6 membered heteroaryl group, or aryl or a 5 or 6 membered heteroaryl group substituted by lower alkyl, halogen, hydroxy or lower alkoxy;

X is a bond or —N(R$^e$)CH$_2$—;

R, R$^a$, R$^b$, R$^c$, R$^d$, R$^e$ are independently selected from hydrogen or lower alkyl;

n is 0, 1, 2, 3, 4, 5 or 6;

or a pharmaceutically acceptable salt thereof.

2. A compound of the formula

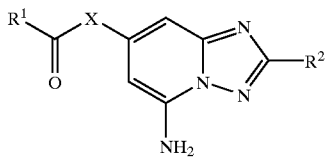

wherein $R^1$ is lower alkoxy, cycloalkyl or aryl, unsubstituted or substituted by halogen or lower alkoxy, or is —NR'R", wherein R' and R" are independently from each other hydrogen, lower alkyl, lower alkenyl, lower alkinyl, unsubstituted —(CR$_2$)$_n$-aryl, or —(CR$_2$)$_n$-aryl, substituted by one to three substituents, selected from the group, consisting of halogen or lower alkoxy, or are —(CH$_2$)$_{n+1}$NR$^a_2$, —(CH$_2$)$_n$-pyridinyl, —(CH$_2$)$_n$-indanyl, —(CH$_2$)$_n$-cycloalkyl, —(CH$_2$)$_n$—O-lower alkyl, —(CH$_2$)$_n$—CF$_3$, or R' and R" are together with the N atom to which they are attached form unsubstituted pyrrolidin-1-yl, piperidin-1-yl, 3,4-dihydro-1H-isoquinolin-2-yl, morpholinyl, azatidin-1-yl, 3,6-dihydro-2H-pyridin-1-yl, thiomorpholinyl, 2,5-dihydro-pyrrol-1-yl, thiazolidin-3-yl, piperazinyl, azocan-1-yl, octahydroquinolin-1-yl, octahydroquinolin-2-yl, 1,3,4,9-tetrahydro-b-carbolin-2-yl, or pyrrolidin-1-yl, piperidin-1-yl, 3,4-dihydro-1H-isoquinolin-2-yl, morpholinyl, azatidin-1-yl, 3,6-dihydro-2H-pyridin-1-yl, thiomorpholinyl, 2,5-dihydro-pyrrol-1-yl, thiazolidin-3-yl, piperazinyl, azocan-1-yl, octahydroquinolin-1-yl, octahydroquinolin-2-yl, 1,3,4,9-tetrahydro-b-carbolin-2-yl substituted by one to three substituents, selected from the group, consisting of lower alkyl, phenyl, benzyl or pyridyl;

$R_2$ is unsubstituted aryl or a 5 or 6 membered unsubstituted heteroaryl group, or an aryl or a 5 or 6 membered heteroaryl group substituted by lower alkyl, halogen, hydroxy or lower alkoxy;

X is a bond or —N(R$^e$)CH$_2$—;

R, R$^a$, R$^e$ are independently, are hydrogen or lower alkyl;

n is 0, 1, 2, 3, 4, 5 or 6;

or a pharmaceutically acceptable salt thereof.

3. The compound of formula I in accordance with claim 1 wherein X is a bond.

4. The compound of formula I in accordance with claim 3, wherein $R^1$ is NR'R' and R' and R" are independently selected from hydrogen, lower alkyl, lower alkenyl, lower alkinyl, —(CH$_2$)$_n$—C(O)—N(CH$_3$)$_2$, —(CH$_2$)$_n$—OCH$_3$, —(CH$_2$)$_n$-cycloalkyl or —(CH$_2$)$_n$-pyridin-2-yl and $R^2$ is unsubstituted furyl or thiophenyl, or furyl or thiophenyl substituted by halogen or lower alkyl.

5. The compound of formula I in accordance with claim 4 wherein one of R' and R" is hydrogen and the other is lower alkyl.

6. The compound of claim 5 wherein the compound is 5-Amino-2-furan-2-yl-[1,2,4]triazolo[1,5-a]pyridine-7-carboxylic acid butylamide.

7. The compound of formula I in accordance with claim 4 wherein both R' and R" are lower alkyl.

8. The compound claim 7 wherein the compound is selected from the group consisting of 5-Amino-2-(5-bromo-furan-2-yl)-[1,2,4]triazolo[1,5-a]pyridine-7-carboxylic acid diethylamide;

5-Amino-2-(5-chloro-furan-2-yl)-[1,2,4]triazolo[1,5-a]pyridine-7-carboxylic acid methyl-propyl-amide;

5-Amino-2-(5-chloro-furan-2-yl)-[1,2,4]triazolo[1,5-a]pyridine-7-carboxylic acid ethyl-isopropyl-amide;

5-Amino-2-(5-bromo-furan-2-yl)-[1,2,4]triazolo[1,5-a]pyridine-7-carboxylic acid ethyl-methyl-amide;

5-Amino-2-furan-2-yl-[1,2,4]triazolo[1,5-a]pyridine-7-carboxylic acid diethylamide 5-Amino-2-(5-bromo-furan-2-yl)-[1,2,4]triazolo[1,5-a]pyridine-7-carboxylic acid isopropyl-methyl-amide;

5-Amino-2-(5-bromo-furan-2-yl)-[1,2,4]triazolo[1,5-a]pyridine-7-carboxylic acid butyl-methyl-amide;

5-Amino-2-(5-bromo-furan-2-yl)-[1,2,4]triazolo[1,5-a]pyridine-7-carboxylic acid ethyl-isopropyl-amide;

5-Amino-2-(5-bromo-furan-2-yl)-[1,2,4]triazolo[1,5-a]pyridine-7-carboxylic acid diisopropylamide;

5-Amino-2-(5-bromo-furan-2-yl)-[1,2,4]triazolo[1,5-a]pyridine-7-carboxylic acid butyl-ethyl-amide;

5-Amino-2-(5-bromo-furan-2-yl)-[1,2,4]triazolo[1,5-a]pyridine-7-carboxylic acid methyl-pentyl-amide;

5-Amino-2-(5-bromo-furan-2-yl)-[1,2,4]triazolo[1,5-a]pyridine-7-carboxylic acid dipropylamide; and 5-Amino-2-(5-bromo-furan-2-yl)-[1,2,4]triazolo[1,5-a]pyridine-7-carboxylic acid diisobutylamide.

9. The compound of formula I in accordance with claim 4 wherein one of R' and R" is —(CH$_2$)$_n$-cycloalkyl and the other is hydrogen, or one of R' and R" is —(CH$_2$)$_n$-cycloalkyl and the other is lower alkyl, or both R' and R" are —(CH$_2$)$_n$-cycloalkyl and wherein n is 0, 1, 2, 3, 4, 5 or 6.

10. The compound claim 9, wherein the compound is selected from the group consisting of 5-Amino-2-(5-methyl-thiophen-2-yl)-[1,2,4]triazolo[1,5-a]pyridine-7-carboxylic acid cyclohexyl-ethyl-amide;

5-Amino-2-(5-methyl-furan-2-yl)-[1,2,4]triazolo[1,5-a]pyridine-7-carboxylic acid cyclohexyl-methyl-amide;

5-Amino-2-(5-bromo-furan-2-yl)-[1,2,4]triazolo[1,5-a]pyridine-7-carboxylic acid cyclopropylmethyl-propyl-amide; and 5-Amino-2-(5-bromo-furan-2-yl)-[1,2,4]triazolo[1,5-a]pyridine-7-carboxylic acid cyclohexyl-ethyl-amide.

11. The compound of formula I in accordance with claim 4 wherein one of R' and R" lower alkyl and the other is lower alkinyl.

12. The compound of formula I in accordance with claim 11 wherein the compound is 5-Amino-2-(5-bromo-furan-2-yl)-[1,2,4]triazolo[1,5-a]pyridine-7-carboxylic acid methyl-prop-2-ynyl-amide.

13. The compound of formula I in accordance with claim 4 wherein one of R' and R" lower alkyl and the other is lower alkenyl, or one is —(CH$_2$)$_n$-cycloalkyl and the other is lower alkenyl, or both R',and R" are lower alkenyl, and wherein n is 0, 1, 2, 3, 4, 5 or 6.

14. The compound of formula I in accordance with claim 13 wherein the compound is 5-Amino-2-(5-bromo-furan-2-yl)-[1,2,4]triazolo[1,5-a]pyridine-7-carboxylic acid allyl-methyl-amide;

5-Amino-2-(5-bromo-furan-2-yl)-[1,2,4]triazolo[1,5-a]pyridine-7-carboxylic acid methyl-propyl-amide;

5-Amino-2-(5-bromo-furan-2-yl)-[1,2,4]triazolo[1,5-a]pyridine-7-carboxylic acid diallylamide; or

[5-Amino-2-(5-bromo-furan-2-yl)-[1,2,4]triazolo[1,5-a]pyridin-7-yl]-phenyl-methanone.

15. The compound of formula I in accordance with claim 4 wherein one of R' and R" —(CH$_2$)$_n$-pyridinyl and the other is lower alkyl, and wherein n is 0, 1, 2, 3, 4, 5 or 6.

16. The compound of formula I in accordance with claim 15 wherein the compound is 5-Amino-2-(5-bromo-furan-2-yl)-[1,2,4]triazolo[1,5-a]pyridine-7-carboxylic acid methyl-(2-pyridin-2-yl-ethyl)-amide; or 5-Amino-2-(5-bromo-furan-2-yl)-[1,2,4]triazolo[1,5-a]pyridine-7-carboxylic acid ethyl-(2-pyridin-2-yl-ethyl)-amide.

17. The compound of formula I in accordance with claim 4 wherein one of R' and R" is —(CH$_2$)$_n$—OCH$_3$ and the other is lower alkyl, and wherein n is 0, 1, 2, 3, 4, 5 or 6.

18. The compound of formula I in accordance with claim 17 wherein the compound is 5-Amino-2-(5-bromo-furan-2-yl)-[1,2,4]triazolo[1,5-a]pyridine-7-carboxylic acid (2-methoxy-ethyl)-methyl-amide or 5-Amino-2-(5-bromo-furan-2-yl)-[1,2,4]triazolo[1,5-a]pyridine-7-carboxylic acid ethyl-(2-methoxy-ethyl)-amide.

19. The compound of formula I in accordance with claim 4 wherein one of R' and R" is —(CH$_2$)$_n$—N—(CH$_3$)$_2$ and the other is lower alkyl, and wherein n is 0, 1, 2, 3, 4, 5 or 6.

20. The compound of claim 19 wherein the compound is 5-Amino-2-(5-bromo-furan-2-yl)-[1,2,4]triazolo[1,5-a]pyridine-7-carboxylic acid (2-dimethylamino-ethyl)-methyl-amide.

21. The compound of formula I in accordance with claim 4 wherein one of R' and R" is —(CH$_2$)$_n$—C(O)—N(CH$_3$)$_2$ and the other is lower alkyl, and wherein n is 0, 1, 2, 3, 4, 5 or 6.

22. The compound of claim 21 wherein the compound is 5-Amino-2-(5-bromo-furan-2-yl)-[1,2,4]triazolo[1,5-a]pyridine-7-carboxylic acid dimethylcarbamoylmethyl-methyl-amide.

23. The compound of formula I in accordance with claim 3, wherein R' and R" are independently from each other hydrogen, lower alkyl, lower alkenyl, lower alkinyl, and R$_2$ is thiazol-2-yl.

24. The compound of formula I in accordance with claim 23 wherein one of R' and R" is hydrogen and the other is lower alkyl.

25. A compound of claim 24 wherein the compound is 5-Amino-2-thiazol-2-yl-[1,2,4]triazolo[1,5-a]pyridine-7-carboxylic acid butylamide; or 5-Amino-2-thiazol-2-yl-[1,2,4]triazolo[1,5-a]pyridine-7-carboxylic acid ethylamide.

26. The compound of formula I in accordance with claim 23 wherein R' and R" are lower alkyl.

27. The compound of claim 26 wherein the compound is selected from the group consisting of 5-Amino-2-thiazol-2-yl-[1,2,4]triazolo[1,5-a]pyridine-7-carboxylic acid diethylamide;

5-Amino-2-thiazol-2-yl-[1,2,4]triazolo[1,5-a]pyridine-7-carboxylic acid ethyl-methyl-amide;

5-Amino-2-thiazol-2-yl-[1,2,4]triazolo[1,5-a]pyridine-7-carboxylic acid methyl-propyl-amide;

5-Amino-2-thiazol-2-yl-[1,2,4]triazolo[1,5-a]pyridine-7-carboxylic acid isopropyl-methyl-amide;

5-Amino-2-thiazol-2-yl-[1,2,4]triazolo[1,5-a]pyridine-7-carboxylic acid butyl-methyl-amide;

5-Amino-2-thiazol-2-yl-[1,2,4]triazolo[1,5-a]pyridine-7-carboxylic acid dipropylamide; and 5-Amino-2-thiazol-2-yl-[1,2,4]triazolo[1,5-a]pyridine-7-carboxylic acid diisobutylamide.

28. The compound of formula I in accordance with claim 23 wherein one of R' and R" is lower alkyl and the other is lower alkenyl.

29. The compound of claim 28 wherein the compound is 5-Amino-2-thiazol-2-yl-[1,2,4]triazolo[1,5-a]pyridine-7-carboxylic acid allyl-methyl-amide.

30. The compound of formula I in accordance with claim 23 wherein one of R' and R" is lower alkyl and the other is lower alkinyl.

31. The compound of claim 29 wherein the compound is 5-Amino-2-thiazol-2-yl-[1,2,4]triazolo[1,5-a]pyridine-7-carboxylic acid methyl-prop-2-ynyl-amide.

32. The compound of formula 1 in accord with claim 23 wherein one of R' and R" is —(CH$_2$)$_n$-pyridinyl and the other is lower alkyl and wherein n is 0, 1, 2, 3, 4, 5 or 6.

33. The compound of claim 32 wherein the compound is 5-Amino-2-thiazol-2-yl-[1,2,4]triazolo[1,5-a]pyridine-7-carboxylic acid ethyl-pyridin-4-ylmethyl-amide.

34. The compound of formula I in accordance with claim 23 wherein R' and R" are both —(CH$_2$)$_n$-aryl and wherein n is 0, 1, 2, 3, 4, 5 or 6.

35. The compound of claim 34 wherein the compound is 5-Amino-2-thiazol-2-yl-[1,2,4]triazolo[1,5-a]pyridine-7-carboxylic acid dibenzylamide.

36. The compound of formula I in accordance with claim 3, wherein R' and R" are together with the N atom to which they are attached form unsubstituted pyrrolidinyl, piperidinyl, morpholinyl, 3,6-dihydro-2H-pyridin-1-yl, 2,5-dihydro-pyrrol-1-yl, azocan-1-yl; or pyrrolidinyl, piperidinyl, morpholinyl, 3,6-dihydro-2H-pyridin-1-yl, 2,5-dihydro-pyrrol-1-yl, azocan-1-yl, substituted by lower alkyl, lower alkoxy, —C(O)NH$_2$, —C(O)N(CH$_3$)$_2$, or —N(CH$_3$)—C(O)—CH$_3$ and R$^2$ is unsubstituted furyl or furyl substituted by halogen.

37. The compound of claim 36 wherein R' and R" are together with the N atom to which they are attached form unsubsituted pyrrolidinyl, piperidinyl, or morpholinyl.

38. The compound of claim 37 wherein the compound is selected from the group consisting of [5-Amino-2-(5-bromo-furan-2-yl)-[1,2,4]triazolo[1,5-a]pyridin-7-yl]-pyrrolidin-1-yl-methanone;

[5-Amino-2-(5-bromo-furan-2-yl)-[1,2,4]triazolo[1,5-a]pyridin-7-yl]-piperidin-1yl-methanone;

(5-Amino-2-furan-2-yl-[1,2,4]triazolo[1,5-a]pyridin-7-yl)-pyrrolidin-1-yl-methanone;

(5-Amino-2-furan-2-yl-[1,2,4]triazolo[1,5-a]pyridin-7-yl)-piperidin-1-yl-methanone;

(5-Amino-2-furan-2-yl-[1,2,4]triazolo[1,5-a]pyridin-7-yl)-morpholin-4-yl-methanone;

[5-Amino-2-(5-chloro-furan-2-yl)-[1,2,4]triazolo[1,5-a]pyridin-7-yl]-pyrrolidin-1-yl-methanone;

[5-Amino-2-(5-chloro-furan-2-yl)-[1,2,4]triazolo[1,5-a]pyridin-7-yl]-piperidine-1-yl-methanone;

[5-Amino-2-(5-chloro-furan-2-yl)-[1,2,4]triazolo[1,5-a]pyridin-7-yl]-morpholin-4-yl-methanone;

[5-Amino-2-(5-chloro-furan-2-yl)-[1,2,4]triazolo[1,5-a]pyridin-7-yl]-(3,6-dihydro-2H-pyridin-1-yl)-methanone;

[5-Amino-2-(5-bromo-furan-2-yl)-[1,2,4]triazolo[1,5-a]pyridin-7-yl]-(2,5-dihydro-pyrrol-1-yl)-methanone; and

[5-Amino-2-(5-bromo-furan-2-yl)-[1,2,4]triazolo[1,5-a]pyridin-7-yl]-azocan-1-yl-methanone.

39. The compound of formula I in accordance with claim 36 wherein R' and R" are together with the N atom to which they are attached form substituted pyrrolidinyl, piperidinyl, morpholinyl, 3,6-dihydro-2H-pyridin-1-yl, 2,5-dihydro-pyrrol-1-yl, or azocan-1-yl; substituted by lower alkyl, lower alkoxy, —C(O)NH$_2$, —C(O)N(CH$_3$)$_2$, or —N(CH$_3$)—C(O)—CH$_3$.

40. The compound of claim 39 wherein the compound is selected from the group consisting of [5-Amino-2-(5-chloro-furan-2-yl)-[1,2,4]triazolo[1,5-a]pyridin-7-yl]-methyl-pyrrolidin-1-yl)-methanone;

[5-Amino-2-(5-bromo-furan-2-yl)-[1,2,4]triazolo[1,5-a]pyridin-7-yl]-(2-methyl-pyrrolidin-1-yl)-methanone;

[5-Amino-2-(5-bromo-furan-2-yl)-[1,2,4]triazolo[1,5-a]pyridin-7-yl]-(2,5-dimethyl-2,5-dihydro-pyrrol-1-yl)-methanone;

[5-Amino-2-(5-bromo-furan-2-yl)-[1,2,4]triazolo[1,5-a]pyridin-7-yl]-(2,5-dimethyl-pyrrolidin-1-yl)-methanone;

[5-Amino-2-(5-bromo-furan-2-yl)-[1,2,4]triazolo[1,5-a]pyridin-7-yl]-(2,6-dimethyl-morpholin-4-yl)-methanone;

[5-Amino-2-(5-bromo-furan-2-yl)-[1,2,4]triazolo[1,5-a]pyridin-7-yl]-(2-methyl-piperidin-1-yl)-methanone

[5-Amino-2-(5-bromo-furan-2-yl)-[1,2,4]triazolo[1,5-a]pyridin-7-yl]-(4-methyl-piperidin-1-yl)-methanone;

[5-Amino-2-(5-bromo-furan-2-yl)-[1,2,4]triazolo[1,5-a]pyridin-7-yl]-(3,5-dimethyl-piperidin-1-yl)-methanone;

1-[5-Amino-2-(5-bromo-furan-2-yl)-[1,2,4]triazolo[1,5-a]pyridine-7-carbonyl]-piperidine-3-carboxylic acid diethylamide;

[5-Amino-2-(5-bromo-furan-2-yl)-[1,2,4]triazolo[1,5-a]pyridin-7-yl]-[(2R,5R)-trans-2,5-dimethyl-pyrrolidin-1-yl]-methanone;

[5-Amino-2-(5-bromo-furan-2-yl)-[1,2,4]triazolo[1,5-a]pyridin-7-yl]-(cis-2,6-dimethyl-morpholin-4-yl)-methanone;

[5-Amino-2-(5-bromo-furan-2-yl)-[1,2,4]triazolo[1,5-a]pyridin-7-yl]-(S-2-methoxymethyl-pyrrolidin-1-yl)-methanone;

[5-Amino-2-(5-bromo-furan-2-yl)-[1,2,4]triazolo[1,5-a]pyridin-7-yl]-(R-2-methoxymethyl-pyrrolidin-1-yl)-methanone;

1-[5-Amino-2-(5-bromo-furan-2-yl)-[1,2,4]triazolo[1,5-a]pyridine-7-carbonyl]-L-pyrrolidine-2-carboxylic acid amide;

1-[5-Amino-2-(5-bromo-furan-2-yl)-[1,2,4]triazolo[1,5-a]pyridine-7-carbonyl]-D-pyrrolidine-2-carboxylic acid amide;

N-{1-[5-Amino-2-(5-bromo-furan-2-yl)-[1,2,4]triazolo[1,5-a]pyridine-7-carbonyl]-pyrrolidin-3-yl}-acetamide;

N-{1-[5-Amino-2-(5-bromo-furan-2-yl)-[1,2,4]triazolo[1,5-a]pyridine-7-carbonyl]-pyrrolidin-3-yl}-N-methyl-acetamide;

[5-Amino-2-(5-bromo-furan-2-yl)-[1,2,4]triazolo[1,5-a]pyridin-7-yl]-(5-ethyl-2-methyl-piperidin-1-yl)-methanone; and 1-[5-Amino-2-(5-bromo-furan-2-yl)-[1,2,4]triazolo[1,5-a]pyridine-7-carbonyl]-piperidine-3-carboxylic acid amide.

41. The compound of formula I in accordance with claim 35, wherein R' and R" are together with the N atom to which they are attached form unsubstituted pyrrolidinyl, piperidinyl, octahydroquinolin-1-yl, 2,5-dihydro-pyrrol-1-yl, thiazolidinyl, azepan-1-yl or azocan-1-yl and $R^2$ is thiazolyl.

42. The compound of claim 41 wherein the compound is selected from the group consisting of (5-Amino-2-thiazol-2-yl-[1,2,4]triazolo[1,5-a]pyridin-7-yl)-pyrrolidin-1-yl-methanone;

(5-Amino-2-thiazol-2-yl-[1,2,4]triazolo[1,5-a]pyridin-7-yl)-piperidin-1-yl-methanone;

(5-Amino-2-thiazol-2-yl-[1,2,4]triazolo[1,5-a]pyridin-7-yl)-(2,5-dihydro-pyrrol-1-yl)-methanone;

(5-Amino-2-thiazol-2-yl-[1,2,4]triazolo[1,5-a]pyridin-7-yl)-thiazolidin-3-yl-methanone;

(5-Amino-2-thiazol-2-yl-[1,2,4]triazolo[1,5-a]pyridin-7-yl)-azepan-1-yl-methanone;

(5-Amino-2-thiazol-2-yl-[1,2,4]triazolo[1,5-a]pyridin-7-yl)-azocan-1-yl-methanone; and (5-Amino-2-thiazol-2-yl-[1,2,4]triazolo[1,5-a]pyridin-7-yl)-(octahydro-quinolin-1-yl)-methanone.

43. The compound of formula I in accordance with claim 3, wherein R' and R" are, together with the N atom to which they are attached form substituted pyrrolidinyl, piperidinyl, octahydroquinolin-1-yl, 2,5-dihydro-pyrrol-1-yl, thiazolidinyl, azepan-1-yl or azocan-1-yl, wherein said substituents are lower alkyl, and $R^2$ is thiazolyl.

44. The compound of claim 43 wherein the compound is selected from the group consisting of (5-Amino-2-thiazol-2-yl-[1,2,4]triazolo[1,5-a]pyridin-7-yl)-(2-methyl-pyrrolidin-1-yl)-methanone;

(5-Amino-2-thiazol-2-yl-[1,2,4]triazolo[1,5-a]pyridin-7-yl)-(2,6-dimethyl-piperidin-1-yl)-methanone;

(5-Amino-2-thiazol-2-yl-[1,2,4]triazolo[1,5-a]pyridin-7-yl)-(2-methyl-piperidin-1-yl)-methanone;

(5-Amino-2-thiazol-2-yl-[1,2,4]triazolo[1,5-a]pyridin-7-yl)-(4-methyl-piperidin-1-yl)-methanone;

(5-Amino-2-thiazol-2-yl-[1,2,4] triazolo[1,5-a]pyridin-7-yl)-(3,5-dimethyl-piperidin-1-yl)-methanone;

(5-Amino-2-thiazol-2-yl-[1,2,4]triazolo[1,5-a]pyridin-7-yl)-(2,6-dimethyl-piperidin-1-yl)-methanone; and (5-Amino-2-thiazol-2-yl-[1,2,4]triazolo[1,5-a]pyridin-7-yl)-(cis-2,6-dimethyl-piperidin-1-yl)-methanone.

45. The compound of formula I in accordance with claim 3, wherein R' and R" together with the N atom to which they are attached form unsubstituted pyrrolidin-1-yl, azepan-1-yl, piperidin-1-yl, or azocan-1-yl, or substituted pyrrolidin-1-yl, azepan-1-yl, piperidin-1-yl, or azocan-1-yl, and wherein said substituents are lower alkyl or lower alkoxy, and $R^2$ is pyridyl.

46. The compound of claim 45 wherein R' and R" together with the N atom to which they are attached form unsubstituted pyrrolidin-1-yl, azepan-1-yl, piperidin-1-yl, or azocan-1-yl.

47. The compound of claim 46 wherein the compound is (5-Amino-2-pyridin-2-yl-[1,2,4]triazolo[1,5-a]pyridin-7-yl)-azepan-1-yl-methanone.

48. The compound of formula I in accordance with claim 45, wherein R' and R" together with the N atom to which they are attached form substituted pyrrolidin-1-yl, azepan-1-yl, piperidin-1-yl, or azocan-1-yl, and wherein said substituents are lower alkyl or lower alkoxy.

49. The compound of claim 47 wherein the compound is selected from the group consisting of (5-Amino-2-pyridin-2-yl-[1,2,4]triazolo[1,5-a]pyridin-7-yl)-(2-methyl-pyrrolidin-1-yl)-methanone;

- (5-amino-2-pyridin-2-yl-[1,2,4]triazolo[1,5-a]pyridin-7-yl)-(2-methyl-piperidin-1-yl)-methanone;
- (5-Amino-2-pyridin-2-yl-[1,2,4]triazolo[1,5-a]pyridin-7-yl)-(3-methyl-piperidin-1-yl)-methanone;
- (5-Amino-2-pyridin-2-yl-[1,2,4]triazolo[1,5-a]pyridin-7-yl)-azocan-1-yl-methanone;
- (5-Amino-2-pyridin-2-yl-[1,2,4]triazolo[1,5-a]pyridin-7-yl)-(3,5-dimethyl-piperidin-1-yl)-methanone; or
- (5-Amino-2-pyridin-2-yl-[1,2,4]triazolo[1,5-a]pyridin-7-yl)-(R-2-methoxymethyl-pyrrolidin-1-yl)-methanone.

50. The compound of formula I in accordance with claim 3, wherein R' and R" are independently from each other lower alkenyl, lower alkyl, —(CH$_2$)$_n$-cycloalkyl, —(CH$_2$)$_n$-pyridinyl or —(CH$_2$)$_n$-phenyl and R$^2$ is pyridyl.

51. The compound claim 50 wherein the compound is selected from the group consisting of (5-Amino-2-pyridin-2-yl-[1,2,4]triazolo[1,5-a]pyridin-7-yl)-azepan-1-yl-methanone;

- 5-Amino-2-pyridin-2-yl-[1,2,4]triazolo[1,5-a]pyridine-7-carboxylic acid cyclopropylmethyl-propyl-amide;
- 5-Amino-2-pyridin-2-yl-[1,2,4]triazolo[1,5-a]pyridine-7-carboxylic acid allyl-cyclopentyl-amide;
- 5-Amino-2-pyridin-2-yl-[1,2,4]triazolo[1,5-a]pyridine-7-carboxylic acid ethyl-pyridin-4-ylmethyl-amide;
- 5-Amino-2-pyridin-2-yl-[1,2,4]triazolo[1,5-a]pyridine-7-carboxylic acid benzyl-isopropyl-amide; or
- 5-Amino-2-pyridin-2-yl-[1,2,4]triazolo[1,5-a]pyridine-7-carboxylic acid dibenzylamide.

52. A pharmaceutical composition for the treatment of depressive disorders and Parkinson's disease comprising an effective amount of at least one compound of formula 1 according to claim 1 and at least one pharmaceutically acceptable excipient.

53. A method of treating a disease responsive to modulation of the adenosine receptor in a person having need of such treatment comprising administering to the person a therapeutically effective amount of at least one compound of formula 1 according to claim 1.

* * * * *

UNITED STATES PATENT AND TRADEMARK OFFICE
CERTIFICATE OF CORRECTION

PATENT NO.    : 6,506,772 B1
DATED         : January 14, 2003
INVENTOR(S)   : Brodbeck et al.

It is certified that error appears in the above-identified patent and that said Letters Patent is hereby corrected as shown below:

Column 164,
Line 7, delete "NR'R'" and insert -- NR'R" --

Column 165,
Line 61, delete "$R_2$" and insert -- $R^2$ --

Column 166,
Line 63, delete "pyridin-7-yl]-piperidin-1yl-methanone;" and insert
-- pyridin-7-yl]-piperidin-1-yl-methanone; --

Column 167,
Line 25, delete "furan-2-yl)-[1,2,4]triazolo[1,5-a]pyridin-7-yl]-methyl" and insert
-- furan-2-yl)-[1,2,4]triazolo[1,5-a]pyridin-7-yl]-2-methyl --

Signed and Sealed this

Twelfth Day of August, 2003

JAMES E. ROGAN
*Director of the United States Patent and Trademark Office*